(12) United States Patent
Wang et al.

(10) Patent No.: US 12,152,070 B2
(45) Date of Patent: Nov. 26, 2024

(54) MEDICINAL COMPOSITION CONTAINING MONOCLONAL ANTIBODY OR ANTIBODY FAB FRAGMENT THEREOF, AND USE THEREOF

(71) Applicant: Ohealth Biopharmaceutical (Suzhou) Co., Ltd., Suzhou (CN)

(72) Inventors: Ju-Ming Wang, Tainan (CN); I-Chen Lee, Tainan (CN); Yu-Wei Hsiao, Tainan (CN); Jhih-Ying Chi, New Taipei (CN); Jyun-yi Du, Tainan (CN); Hsin-Yin Liang, Tainan (CN); Chao-chun Cheng, Tainan (CN); Chiung-Yuan Ko, Kaohsiung (CN); Feng-Wei Chen, Kaohsiung (CN); Jhih-Yun Liu, Chiayi County (CN)

(73) Assignee: Ohealth Biopharmaceutical (Suzhou) Co., Ltd., Suzhou (CN)

( * ) Notice: Subject to any disclaimer, the term of this patent is extended or adjusted under 35 U.S.C. 154(b) by 886 days.

(21) Appl. No.: 17/274,960

(22) PCT Filed: Sep. 13, 2019

(86) PCT No.: PCT/CN2019/105824
§ 371 (c)(1),
(2) Date: Mar. 10, 2021

(87) PCT Pub. No.: WO2020/052675
PCT Pub. Date: Mar. 19, 2020

(65) Prior Publication Data
US 2022/0119507 A1 Apr. 21, 2022

Related U.S. Application Data

(60) Provisional application No. 62/867,244, filed on Jun. 27, 2019.

(30) Foreign Application Priority Data

Sep. 14, 2018 (WO) ................ PCT/CN2018/105733
Sep. 18, 2018 (WO) ................ PCT/CN2018/106144

(51) Int. Cl.
| | | |
|---|---|---|
| C07K 16/28 | (2006.01) | |
| A61P 35/00 | (2006.01) | |
| C07K 16/18 | (2006.01) | |
| G01N 33/577 | (2006.01) | |
| A61K 39/00 | (2006.01) | |

(52) U.S. Cl.
CPC ............. *C07K 16/18* (2013.01); *A61P 35/00* (2018.01); *G01N 33/577* (2013.01); *A61K 2039/505* (2013.01); *C07K 2317/24* (2013.01); *C07K 2317/31* (2013.01); *C07K 2317/34* (2013.01); *C07K 2317/76* (2013.01); *C07K 2317/92* (2013.01)

(58) Field of Classification Search
CPC ................ C07K 16/18; C07K 2317/24; C07K 2317/31; C07K 2317/34; C07K 2317/76; C07K 2317/92; A61P 35/00; A61P 35/04; A61P 1/16; A61P 11/00; A61P 13/12; G01N 33/577; A61K 2039/505; A61K 31/337; A61K 39/395
See application file for complete search history.

(56) References Cited

U.S. PATENT DOCUMENTS

| | | | |
|---|---|---|---|
| 2004/0038207 | A1 | 2/2004 | Orntoft |
| 2014/0364374 | A1 | 12/2014 | Wang et al. |
| 2016/0347800 | A1 | 12/2016 | Wang et al. |
| 2016/0376305 | A1 | 12/2016 | Tseng et al. |

FOREIGN PATENT DOCUMENTS

| | | | |
|---|---|---|---|
| CN | 1893975 A | 1/2007 | |
| CN | 1947018 A | 4/2007 | |
| CN | 101606067 A | 12/2009 | |
| CN | 102918063 A | 2/2013 | |
| CN | 103372213 A | 10/2013 | |
| CN | 104231064 A | 12/2014 | |
| CN | 106188244 A | 12/2016 | |
| EP | 1720014 A1 | 11/2006 | |
| EP | 1947460 A1 | 7/2008 | |
| EP | 1 947 460 | * 5/2012 | ............. G01N 33/68 |
| JP | 2007534951 A | 11/2007 | |
| JP | 2009014521 A | 1/2009 | |
| TW | 201446260 A | 12/2014 | |
| TW | 201532611 A | 9/2015 | |
| TW | 201641117 A | 12/2016 | |

(Continued)

OTHER PUBLICATIONS

Mariuzza (Annu. Rev. Biophys. Biophys. Chem., 16: 139-159, 1987).*
Hsiao Y-W, Chi J-Y, Li C-F, et al. Disruption of the pentraxin 3/CD44 interaction as an efficient therapy for triple-negative breast cancers. Clin Transl Med. 2022;12:e724.
Chi J-Y, Hsiao Y-W, Liang H-Y, et al. Blockade of the pentraxin 3/CD44 interaction attenuates lung injury-induced fibrosis. Clin Transl Med. 2022; 12:e1099.
Ramery, E., et al., Characterization of pentraxin 3 in the horse and its expression in airways, Vet Res. Mar.-Apr. 2010;41(2):18.
Japanese Office Action issued in JP 2021-538885 on Aug. 3, 2023.
Xie, J. et al., "The Clinical Significance of Serum Pentraxin-3 in ANCA Associated Vasculitis"; Immunological Journal (2014); vol. 30:5; pp. 436-437.

(Continued)

*Primary Examiner* — Nelson B Moseley, II
(74) *Attorney, Agent, or Firm* — Fox Rothschild LLP

(57) ABSTRACT

The present invention provides a PTX3 monoclonal antibody or antibody Fab fragment thereof and use thereof. The aforementioned monoclonal antibody or antibody Fab fragment thereof specifically inhibit or slow down the binding of PTX3 to the PTX3 receptor, and may be used for a kit and method for detecting PTX3, and a pharmaceutical composition which inhibits or slows down diseases or symptoms associated with PTX3 and PTX3 receptor binding, and a use thereof.

21 Claims, 35 Drawing Sheets

Specification includes a Sequence Listing.

(56) References Cited

FOREIGN PATENT DOCUMENTS

| WO | 92/12176 A1 | 7/1992 |
|---|---|---|
| WO | 2004063334 A2 | 7/2004 |
| WO | 2005/080981 A1 | 9/2005 |
| WO | 2008/012941 A1 | 1/2008 |
| WO | 2008/099608 A1 | 8/2008 |
| WO | 2019056991 A1 | 3/2019 |

OTHER PUBLICATIONS

Camozzi, M. et al., "Identification of an Antiangiogenic FGF2-Binding Site in the N Terminus of the Soluble Pattern Recognition Receptor PTX3"; Journal of Biology Chemistry (2006); vol. 281:32; pp. 22605-22613.

Chan, S. et al., "Oleate-Induced PTX3 Promotes Head and Neck Squamous Cell Carcinoma Metastasis Through the Up-Regulation of Vimentin"; Oncotarget (2017); vol. 8:25; pp. 41364-41378.

Chang, W. et al., "PTX3 Gene Activation in EGF-Induced Head and Neck Cancer Cell Metastasis"; Oncotarget (2015); vol. 6:10; 29 pgs.

Hung, T. et al., "Pentraxin 3 Activates JNK Signaling and Regulates the Epithelial-To-Mesenchymal Transition in Renal Fibrosis"; Cellular Physiology and Biochemistry (2016); vol. 40: pp. 1029-1038.

Jaillon, S. et al., "Endogenous PTX3 Translocates at the Membrane of Late Apoptotic Human Neutrophils and is Involved in their Engulfment by Macrophages"; Cell Death and Differentiation (2009); pp. 465-474.

Chi, J. et al., "Targeting Chemotherapy-Induced PTX3 in Tumor Stroma to Prevent the Progression of Drug-Resistant Cancers"; Oncotarget (2015); vol. 6:7; 15 pgs.

Bassi et al., "IgG anti-pentraxin 3 antibodies in systemic lupus erythematosus," Ann Rheum Dis (2010); 69: 1704-1710.

Bussolati et al., "The Long Pentraxin Ptx3 Is Synthesized in IgA Glomerulonephritis and Activates Mesangial Cells," The Journal of Immunology (2003); 170: 1466-1472.

Hida et al., "Tumor endothelial cells express high pentraxin 3 levels," Pathology International (2016); 66: 687-694.

Tung et al., "Inhibition of pentraxin 3 in glioma cells impairs proliferation and invasion in vitro and in vivo," J Neurooncol (2016); 129: 201-209.

Song et al., "Pentraxin 3 overexpression accelerated tumor metastasis and indicated poor prognosis in hepatocellular carcinoma via driving epithelial-mesenchymal transition," Journal of Cancer (2018); 9: 2650-2658.

Supplementary European Search Report issued on May 6, 2022 for European Patent Application No. 19861063.6.

* cited by examiner

MEDICINAL COMPOSITION CONTAINING MONOCLONAL ANTIBODY OR ANTIBODY FAB FRAGMENT THEREOF, AND USE THEREOF

BACKGROUND

Field of Invention

The present invention relates to an antibody and uses thereof. More specifically, the present invention relates to a monoclonal antibody or antigen-binding fragment for specifically inhibiting or alleviating the binding of C-terminal specific sequence of PTX3 protein to PTX3 receptor, and its applications on detection reagents, medicinal compositions and uses of disease or symptoms related to specific inhibition or alleviation of the binding of C-terminal specific sequence of PTX3 to PTX3 receptor.

Description of Related Art

It is well known that cancer cells can stimulate tumor microenvironment to produce kinds of inflammatory factors, white blood cells, vascular hyperplasia and proteases. Cancer-related chronic inflammation is generally associated with the cancer cell proliferation, metastasis and invasion. However, it is still unclear in how these phenomena occur and detailed mechanism involved therein.

As aforementioned, tumor microenvironment is associated with inflammation; other studies have revealed that tumor microenvironment is deeply associated with metastasis and chemoresistance. Various stromal cells and other different cells types have been found with the tumor microenvironment, which protects and helps tumor cells to evade and resist the immune cells, resulting in chemoresistance of tumor cells.

In the stromal tissue surrounding the tumor, fibroblast and macrophages activated by CEBPD can induce pentraxin-related protein 3 (PTX3), a secreted factor. PTX3 can promote angiogenesis and enhance metastasis and invasion of nasopharyngeal carcinoma (NPC) cell into tissues. In addition, some studies have demonstrated that cells of cancer surrounding tissues activated by CEBPD would facilitate the cancer metastasis and the chemoresistant cancer cells. These chemoresistant cancer cells can grow faster and easier metastasis.

Some small molecule anticancer drugs are commercially available in the market, for example, cis-diammine dichloroplatinum (II) (CDDP; Trade name: Cisplatin); Paclitaxel (Trade name: Taxol); 5-Fluorouracil (5-FU) etc. However, recent studies have found that the aforementioned small molecule anticancer drugs can activate the expression of CEBPD in cancer cells as well as in macrophages and fibroblasts. Instead, small molecule anticancer drugs promote drug resistance and rapid metastasis of cancer cells, resulting in unsatisfactory cancer treatment.

Diseases or symptoms related to PTX3 and its binding to PTX3 receptor are involved in fibrotic diseases and/or fibrotic symptoms in addition to the aforementioned cancers.

Accordingly, there is an urgent need to develop an antibody for specifically binding PTX3, thereby detecting PTX3 amount in a biological specimen and overcoming disadvantages of conventional drugs in insufficient treatments of cancers and fibrosis.

SUMMARY

Therefore, one aspect of the present invention provides a monoclonal antibody or antigen-binding fragment thereof, which specifically recognizes a C-terminal specific sequence of one or more PTX3 proteins.

Another aspect of the present invention provides a monoclonal antibody or antigen-binding fragment thereof comprising a heavy chain variable (VH) domain and a light chain variable (VL) domain, each of which has specific sequences, respectively.

Further aspect of the present invention provides a set for detecting PTX3, comprising a monoclonal antibody or antigen-binding fragment thereof.

Further aspect of the present invention provides a method for in vitro detecting PTX3 using the aforementioned set for detecting PTX3.

Further aspect of the present invention provides a medicinal composition, comprising an effective dose of the aforementioned monoclonal antibody or antigen-binding fragment thereof as an active ingredient and a pharmaceutically acceptable carrier.

Further aspect of the present invention provides a monoclonal antibody or antigen-binding fragment thereof for use as the medicament in specifically inhibiting or alleviating the disease or the symptom related to the PTX3 binding to PTX3 receptor, in which the medicinal composition includes an effective dose of the monoclonal antibody or antigen-binding fragment thereof, thereby inhibiting or alleviating the pentraxin-related protein (PTX3) binding to the PTX3 receptor.

Further aspect of the present invention provides a method of inhibiting or alleviating an activity of a tumor cell in vitro, which includes administering an effective dose of the medicinal composition to the tumor cell, thereby inhibiting or alleviating activities of the tumor cell.

Further aspect of the present invention provides a method for inhibiting or alleviating a disease or a symptom related to fibrosis in vitro, which includes administering an effective dose of the medicinal composition to an organ affected by the disease or the symptom related to the fibrosis, thereby inhibiting or alleviating the disease or the symptom of the organ.

In view of the aforementioned aspect, the present invention provides a monoclonal antibody or antigen-binding fragment thereof. In an embodiment, the monoclonal antibody or the antigen-binding fragment thereof can specifically recognize a non-denatured amino acid sequence selected from the group consisting of amino acid sequences listed as SEQ ID NOs: 1 to 11.

In an embodiment, the non-denatured amino acid sequence is selected from the group consisting of amino acid sequences listed as SEQ ID NOs: 1 to 11. In other embodiments, the non-denatured amino acid sequence can include but be not limited to amino acid sequences listed as SEQ ID NOs: 2 to 4 and SEQ ID NO: 11 or any combination thereof.

According to another aspect, the present invention also provides a monoclonal antibody or antigen-binding fragment thereof, which comprises a heavy chain variable (VH) domain comprising amino acid sequences listed as SEQ ID NO: 18, 19, 20 and/or 21, and a light chain variable (VL) domain comprising amino acid sequences listed as SEQ ID NO: 22, 23, 24 and/or 25.

In some embodiments, the aforementioned monoclonal antibody or antigen-binding fragment thereof includes a VH domain comprising amino acid sequences encoded by nucleic acid sequences listed as SEQ ID NOs: 26, 27, 28 and/or 29, and a VL domain comprising amino acid sequences encoded by nucleic acid sequences listed as SEQ ID NOs: 30, 31, 32 and/or 33.

In other embodiments, the aforementioned monoclonal antibody or antigen-binding fragment thereof includes a VH domain comprising an amino acid sequence listed as SEQ ID NOs: 34 or 35, and a VL domain comprising an amino acid sequence listed as SEQ ID NOs: 36 or 37.

In still other embodiments, the aforementioned monoclonal antibody or antigen-binding fragment thereof includes a VH domain comprising an amino acid sequence encoded by a nucleic acid sequence listed as SEQ ID NOs: 38 or 39, and a VL domain comprising an amino acid sequence encoded by a nucleic acid sequence listed as SEQ ID NOs: 40 or 41.

In an embodiment, the aforementioned monoclonal antibody or antigen-binding fragment thereof is a chimeric antibody or antigen-binding fragment thereof. In an example, the monoclonal antibody or antigen-binding fragment thereof can be a murine antibody, a human-murine chimeric antibody, a humanized antibody or antigen-binding fragment thereof.

In an embodiment, the monoclonal antibody or antigen-binding fragment thereof can be a single-chain variable fragment (scFv), a scFv dimer [(scFv)$_2$], a scFv trimer [(scFv)$_3$], a variable fragment (Fv), a Fab fragment, a Fab' fragment, a dimeric Fab' fragment [F(ab')$_2$], a nanobod or any combination thereof.

In an embodiment, the monoclonal antibody or antigen-binding fragment thereof can be modified by conjugation, coupling, glycosylation, tag attachment or any combination thereof.

In an embodiment, the monoclonal antibody or antigen-binding fragment thereof can be an antibody-drug conjugate (ADC) or antigen-binding fragment thereof.

In an embodiment, the monoclonal antibody or antigen-binding fragment thereof can be a bifunctional monoclonal antibody (BsAb) or antigen-binding fragment thereof.

In an embodiment, the monoclonal antibody or antigen-binding fragment thereof can be a trifunctional monoclonal antibody and/or antigen-binding fragment thereof.

In an embodiment, the monoclonal antibody or antigen-binding fragment thereof can belong to IgG class, IgM class, IgA class, IgD class or IgE class. In another embodiment, the monoclonal antibody or antigen-binding fragment thereof can belong to IgG type and has IgG1 isotype, IgG2 isotype, IgG3 isotype or IgG4 isotype.

In an embodiment, the monoclonal antibody or antigen-binding fragment thereof can belong to an inert antibody or an antagonist antibody.

In an embodiment, the monoclonal antibody or antigen-binding fragment thereof can specifically inhibit or alleviate pentraxin-related protein (PTX3) receptor binding to a C-terminal specific sequence of one or more PTX3 proteins. In some examples, the monoclonal antibody or antigen-binding fragment thereof can specifically inhibit or alleviate activities of one or more PTX3 proteins. In some examples, the monoclonal antibody or antigen-binding fragment thereof can specifically inhibit or alleviate an interaction of PTX3 receptor and one or more PTX3 proteins, PTX3-mediated signal transduction or any combination thereof.

According to other aspects, the present invention also provides a set for in vitro detecting PTX3, which includes any one of the aforementioned monoclonal antibody or antigen-binding fragment thereof, the aforementioned monoclonal antibody or antigen-binding fragment thereof can specifically bind to a non-denatured amino acid sequence, and the non-denatured amino acid sequence can include but be not limited to any amino acid sequence listed as SEQ ID NOs: 1 to 11.

According to yet a further aspect, the invention provides a method for in vitro detecting PTX3 using the aforementioned set for detecting PTX3, in which an analytical sensitivity of the monoclonal antibody or the antigen-binding fragment thereof in the set for detecting PTX3 can be no less than 0.0016 pM.

According to yet a further aspect, the invention provides a medicinal composition, comprising an effective dose of the aforementioned monoclonal antibody or the antigen-binding fragment thereof as an active ingredient and a pharmaceutically acceptable carrier.

In an embodiment, the medicinal composition further includes an active pharmaceutical ingredient.

According to yet a further aspect, the invention provides a monoclonal antibody or antigen-binding fragment thereof for use as a medicament in the treatment of a disease or a symptom related to PTX3 receptor recognizing PTX3. In an embodiment, the medicament comprises an effective dose of a monoclonal antibody or antigen-binding fragment thereof, thereby inhibiting or alleviating a disease or a symptom related to the PTX3 receptor recognizing the PTX3.

In an embodiment, the aforementioned disease or the symptom can include carcinoma, adenocarcinoma, glioblastoma multiforme (GBM) and fibrosis. In some examples, the carcinoma comprises lung cancer, breast cancer and nasopharyngeal cancer. The aforementioned adenocarcinoma comprises colorectal cancer.

In an embodiment, an organ influenced by the disease or the symptom of the fibrosis can include but be not limited to lung, liver, kidney and skin.

In an embodiment, the medicament can be administered via subcutaneous (s.c.) injection, intramuscular injection, intravenous injection, intraperitoneal (i.p.) injection, orthotopic injection, oral administration or nasal inhalation.

According to yet a further aspect, the invention provides a method of inhibiting or alleviating an activity of a tumor cell in vitro, which includes administering an effective dose of the aforementioned medicinal composition to the tumor cell, thereby inhibiting or alleviating activities of the tumor cell.

According to yet a further aspect, the invention provides a monoclonal antibody or antigen-binding fragment thereof for use as a medicament in the treatment of a disease or a symptom related to fibrosis, which includes administering an effective dose of the aforementioned medicinal composition to an organ affected by the disease or the symptom related to the fibrosis, thereby inhibiting or alleviating the disease or the symptom of the organ.

With application to the monoclonal antibody or antigen-binding fragment thereof, in which the specific PTX3 monoclonal antibody or the antigen-binding fragment thereof can specifically inhibit or alleviate PTX3 receptor binding to PTX3, for applications on the set for in vitro detecting PTX3 and the method for in vitro diagnosing PTX3, as well as the medicinal compositions and uses as a medicament in the treatment of the disease or the symptom related to PTX3 receptor recognizing PTX3 protein.

DETAILED DESCRIPTION

Figure 1:
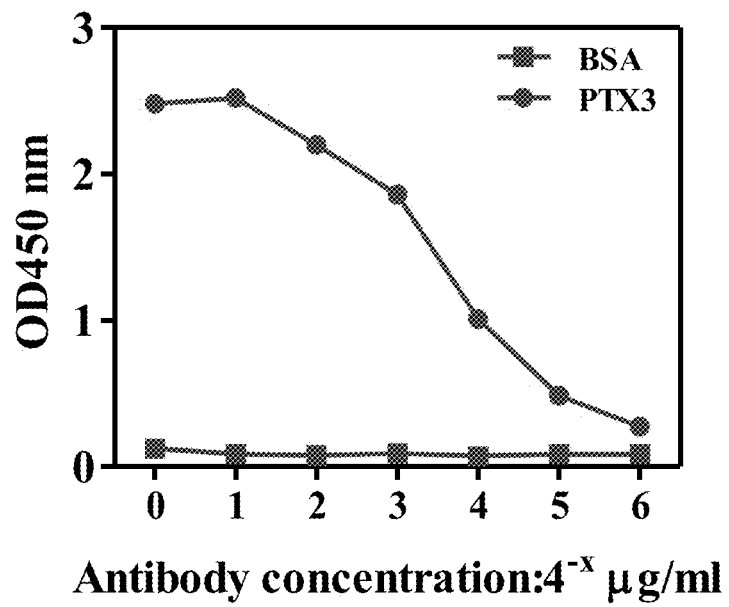
FIG. 1 illustrates an affinity curve diagram of PTX3 monoclonal antibody to PTX3 recombinant protein according to an embodiment of the present invention.

Reference will now be made in detail to the present embodiments of the invention, examples of which are illustrated in the accompanying drawings.

As aforementioned, the present invention provides a medicinal composition including monoclonal antibody or antigen-binding fragment thereof, in which the monoclonal antibody or antigen-binding fragment thereof specifically inhibit the binding of PTX3 and PTX3 receptor, for being applied on a set and a method for in vitro detecting PTX3, as well as a medicinal composition and its use in the inhibition or alleviation of a disease or a symptom related to PTX3 receptor recognizing PTX3.

Specifically, in an embodiment, the monoclonal antibody or antigen-binding fragment thereof can specifically bind to C-terminal amino acid sequence of human PTX3. The range of the C-terminal amino acid sequence of human PTX3 has no limitation, and the C-terminal amino acid sequence of human PTX3 can be a undenatured amino acid sequence from one of SEQ ID NOs:1 to 17, for example, preferably a undenatured amino acid sequence of SEQ ID NOs:1 to 11, more preferably a undenatured amino acid sequence of SEQ ID NOs:1 to 5 and SEQ ID NO:11, and much more preferably a undenatured amino acid sequence of SEQ ID NOs:2 to 4 and SEQ ID NO:11. In the aforementioned embodiment, the undenatured amino acid sequences of SEQ ID NOs:1 to 11 correspond to the $200^{th}$ to $236^{th}$ amino acid residues of the C-terminal amino acid sequence of human PTX3. In another embodiment, the undenatured amino acid sequence of SEQ ID NOs:1 to 5 and SEQ ID NO:11 correspond to the $200^{th}$ to $220^{th}$ amino acid residues of the C-terminal amino acid sequence of human PTX3. In a still another embodiment, the undenatured amino acid sequence of SEQ ID NOs: 2 to 4 and SEQ ID NO:11 correspond to the $203^{rd}$ to $217^{th}$ amino acid residues of the C-terminal amino acid sequence of human PTX3.

In an embodiment, the aforementioned monoclonal antibody or antigen-binding fragment thereof comprises a heavy chain variable (VH) domain sequence and a light chain variable (VL) domain sequence, in which complementarity-determining region (CDR) 1 sequence of the VH domain sequence has an amino acid sequences listed as SEQ ID NO: 1. CDR2 sequence of the VH domain sequence has an amino acid sequences as RIDPANX$_1$X$_2$TKYDPX$_3$FQG, in which X$_1$ represents Gly (G) or Asp (D), X$_2$ represents Asp (D) or Asn (N), X$_3$ represents Lys (K) or Met (M), and the examples of the CDR2 sequence of the VH domain sequence can be listed as SEQ ID NOs:19 or 20. CDR 3 sequence of the VH domain sequence has an amino acid sequences listed as SEQ ID NO: 21. CDR 1 sequence of the VL domain sequence has an amino acid sequences listed as SEQ ID NO: 22. CDR 2 sequence of the VL domain sequence has an amino acid sequences listed as SEQ ID NO: 23. CDR3 sequence of the VL domain sequence has an amino acid sequences as HQX$_4$QRSPLT, in which X$_4$ represents Phe (F) or Tyr (Y), and the examples of the CDR3 sequence of the VL domain sequence can be listed as SEQ ID NOs:24 or 25.

In other embodiments, the aforementioned VH domain sequence of the monoclonal antibody or antigen-binding fragment thereof can have an amino acid sequence encoded by nucleic acid sequence listed as SEQ ID NO:26, SEQ ID NO:27, SEQ ID NO:28 and/or SEQ ID NO:29, and the VL domain sequence of the monoclonal antibody or antigen-binding fragment thereof can have an amino acid sequence encoded by nucleic acid sequence listed as SEQ ID NO:30, SEQ ID NO:31, SEQ ID NO:32 and/or SEQ ID NO:33.

In certain other embodiments, the aforementioned monoclonal antibody or antigen-binding fragment thereof comprises a VH domain sequence with an amino acid sequence listed as SEQ ID NOs:34 or 35, and a VL domain sequence with an amino acid sequence listed as SEQ ID NOs:36 or 37.

In other embodiments, the aforementioned monoclonal antibody or antigen-binding fragment thereof comprises a VH domain sequence with an amino acid sequence encoded by a nucleic acid sequence listed as SEQ ID NOs:38 or 39, and a VL domain sequence with an amino acid sequence encoded by a nucleic acid sequence listed as SEQ ID NOs:40 or 41.

In other embodiments, the aforementioned monoclonal antibody or antigen-binding fragment thereof also encompasses alternative protein structures such as stapled peptides, antibody-like binding peptidomimetics, antibody like binding scaffold proteins, monobodies, and other known non-antibody scaffold proteins. In other embodiments, the aforementioned monoclonal antibody or antigen-binding fragment thereof optionally comprises alternative protein structure, for example, stapled peptides, antibody-like binding peptidomimetics, antibody-like binding scaffold proteins, monobodies and other known non-antibody scaffold proteins.

In some embodiments, there is no limitation to the kinds of the monoclonal antibody or antigen-binding fragment thereof, for example, a chimeric antibody or antigen-binding fragment thereof. In other examples, the monoclonal antibody or antigen-binding fragment thereof can be murine antibody, human-murine antibody, humanized antibody or antibody-binding fragment thereof, for example.

In some embodiment, there is no limitation to the structure of the monoclonal antibody or antigen-binding fragment thereof. In consideration of the premise of the structural stability of complementarity-determining region (CDR), the monoclonal antibody or antigen-binding fragment thereof can be an antibody structure in intact or simplified form, for example, a single-chain variable fragment (scFv), a dimer of scFv (scFv)$_2$, a trimer of scFv (scFv)$_3$, a variable fragment; Fv), an antigen-binding fragment (Fab fragment), a Fab' fragment, a F(ab')$_2$ fragment, a nanobody (also known as a single domain antibody, sdAb), a heavy-chain antibody or any combination thereof, so as to simplify the process of recombinant antibody. The aforementioned monoclonal antibody or antigen-binding fragment thereof can be produced by conventional methods such as hybridoma cells or recombinant gene expression rather than being recited repeatedly.

In some embodiments, the aforementioned monoclonal antibody or antigen-binding fragment thereof can be optionally modified by means of conjugation or coupling, glycosylation, tag attachment or any combination thereof. For example, the aforementioned monoclonal antibody or antigen-binding fragment thereof can be further formed into antibody-drug conjugate (ADC) or antigen-binding fragment thereof. In other examples, the aforementioned monoclonal antibody or antigen-binding fragment thereof can be bound to specific signal peptide for entering specific sites, for example, crossing the blood-brain barrier (BBB).

In some embodiments, the aforementioned monoclonal antibody or antigen-binding fragment thereof can be a bispecific monoclonal antibody (BsAb), a trifunctional monoclonal antibody or antigen-binding fragment thereof.

In an embodiment, the aforementioned monoclonal antibody or antigen-binding fragment thereof can be of any isotype, including IgG, IgM, IgA, IgD or IgE. In an example, the aforementioned monoclonal antibody or antigen-binding fragment thereof can be of IgG isotype including IgG1, IgG2, IgG3 and IgG4 subtypes. In an example, the aforementioned monoclonal antibody or antigen-binding fragment thereof can be an IgG1 subtype such as IgG1k. In some examples, the aforementioned monoclonal antibody or antigen-binding fragment thereof can be an inert antibody or antagonistic antibody. In some examples, the aforementioned monoclonal antibody or to antigen-binding fragment thereof can specifically inhibit or alleviate the activities of one or more kinds of PTX3 proteins. In some other examples, the aforementioned monoclonal antibody or antigen-binding fragment thereof can specifically inhibit or alleviate the interaction of PTX3 receptor with one or more kinds of PTX3 proteins, PTX3-mediated signal transduction or any combination thereof.

In practice, the aforementioned monoclonal antibody or antigen-binding fragment thereof can specifically bind to a undenatured amino acid sequence of SEQ ID NOs:1 to 11, so that it can be applied to a set and a method for detecting PTX3 with higher analytical sensitivity of PTX3 in a biological specimen. The biological specimen can be any form without limitation, including but being not limited to cells, tissues, blood, urine, lymph fluid, tissue fluid, body fluid, etc. The aforementioned set for detecting PTX3 can utilize conventional detection devices/equipments, for example, flow cytometry, enzyme-linked immunosorbent assay (ELISA) detection reagents and kits, biochips, etc.; or conventional detection methods, for example, direct ELISA, indirect ELISA, sandwich ELISA, competitive ELISA), immunohistochemistry (IHC) and Western blotting analysis, etc. In an example, and analytical sensitivity (or called as lower limit of detection, LLOD) of the aforementioned monoclonal antibody or antigen-binding fragment thereof may be no less than 0.0016 pM.

The aforementioned monoclonal antibody or antigen-binding fragment thereof can be active Ingredient in a medicament. In an embodiment, the medicament can optionally include a medically acceptable carrier. The "medically acceptable carrier" hereinafter is defined itself as a nonactive ingredient, for example, a carrier, a diluent, an adjuvant and/or a vehicle for delivering the active ingredient to an individual; or an additive for being added into the aforementioned composition to improve its properties of treatment or storage; or an excipient or any substance for allowing or assisting the dose of the composition adapted for the formation and easy administration of the medicament. The aforementioned medically acceptable carrier should not be harmful to the pharmacological activity of the active ingredient and have no toxicity while delivering an enough on-treatment dose of the active ingredient.

The suitable medically acceptable carrier can be the one commonly known in the prior art and produced by a person skilled in the art to produce a medical composition, and the examples of the carrier can include but be not limited to a buffering agent, a diluent, a disintegrant, a binder, an adhesive, a wetting agent, a polymer, a lubricant, a slip agent, a substance for shielding or eliminating disagreeable taste or odors, a dye, a fragrance and a substance for improving the appearance of the composition. Examples of the medically acceptable carrier can include but be not limited to citrate buffering agent, phosphate buffering agent, acetate buffering agent, bicarbonate buffering agent, stearic acid, magnesium stearate, talc, gelatin, Arabic gum, sodium alginate, pectin, dextrin, mannitol, sorbitol, lactose, sucrose, starch, cellulose derived material (for example, alkanoic acid ester of cellulose, alkyl ester of cellulose), low-melting-point wax, cocoa butter, amino acids, urea, alcohols, ascorbic acid, phospholipids, protein (for example, serum albumin), ethylenediaminetetraacetic acid (EDTA), dimethyl sulfoxide (DMSO), sodium chloride or other salts, liposomes, glycerol or powdered glycerol, polymer (for example, polyvinylpyrrolidone, polyvinyl alcohol and polyethylene glycol) and other medically acceptable substances.

The "inhibition or alleviation of the "disease or symptom" related to PTX3 receptor recognizing PTX3 can include carcinoma, glioblastoma multiforme (GBM), adenoma and fibrosis. The aforementioned carcinoma can be exemplified as lung cancer, breast cancer and nasopharyngeal cancer. The adenocarcinoma can include colorectal cancer. An organ influenced by the disease or the symptom of the fibrosis can include but not be limited to lung, liver (for example, acute hepatic fibrosis, chronic hepatic fibrosis), kidney, skin and the like.

In practice, a medicament can be added with an effective dose of the aforementioned monoclonal antibody or antigen-binding fragment thereof for administering to a target cell or a subject, so as to inhibit or alleviate a disease or a symptom related to PTX3 receptor recognizing PTX3. In a case of mice, the aforementioned "effective dose" refers to the monoclonal antibody or antigen-binding fragment thereof in 2 mg to 10 mg per kg body weight once per a week. In another example, the effective dose of the monoclonal antibody or antigen-binding fragment thereof can be preferably 5 mg to 10 mg per kg body weight, and more preferably 6 mg to 9 mg per kg body weight. As to the application to other subjects, the aforementioned effective dose can be converted to suitable dose depending on bioequivalence. It should be clarified that, if the effective dose of the monoclonal antibody or antigen-binding fragment thereof was less than 2 mg/kg body weight, such dose could not effectively diminish, inhibit or alleviate the PTX3 receptor recognizing PTX3 in a desired period.

As for a tumor, the monoclonal antibody or antigen-binding fragment thereof can inhibit or alleviate activities of tumor cells, such as proliferation, cancer stemness, migration, invasion, metastasis, or drug resistance.

The "fibrosis" discussed herein is defined as the formation of excess fibrous connective tissue in an organ or tissue in a reparative or reactive process. This can be a reactive, benign, or pathological state. Physiologically, fibrosis can be used to describe the pathological state of excess deposition of fibrous tissue, as well as the process of connective tissue deposition in healing, for example, a scar formed in response to injury, a fibroma arisen from a single cell line, or a pathological state of excess deposition of fibrous tissue. As for the organ influenced by the disease or symptom of fibrosis, the monoclonal antibody or antigen-binding fragment thereof can inhibit or alleviate the disease or symptom related to fibrosis, for example, acute hepatic fibrosis, chronic hepatic fibrosis and the like, for acting as broad-spectrum drugs to treat various diseases.

The aforementioned medicament can be administered via subcutaneous injection, intramuscular injection, intravenous injection, intraperitoneal injection, orthotopic injection, oral administration or nasal inhalation, for inhibiting activities of endogenous PTX3, as well as inhibiting or alleviating activities of tumor cells. More specifically, in vitro cell experimentations provide evidences that, activities of tumor cells can be inhibited or alleviated after administration of the monoclonal antibody or antigen-binding fragment thereof of the present invention, or the medicament comprising thereof for a given period, for example, 4 weeks to 11 weeks.

Thereinafter, it will be understood that particular configurations, aspects, examples, clauses and embodiments described hereinafter are shown by way of illustration and not as limitations of the invention. The principal features of this invention can be employed in various embodiments without departing from the scope of the invention. Thus, one skilled in the art can easily ascertain the essential characteristics of the present invention and, without departing from the spirit and scope thereof, can make various changes and modifications of the invention to adapt it to various usages and conditions.

Example 1. Preparation of PTX3 Monoclonal Antibodies

In this EXAMPLE, the PTX3 monoclonal antibody (mAb) recognizing C-terminal amino acid sequence of PTX3 recombinant protein was prepared by conventional hybridoma-based technology or recombinant antibody expression.

In brief, an immunogen of PTX3 recombinant protein listed as a undenatured amino acid sequence of SEQ ID NO:13 was intraperitoneally (i.p.) injected into the abdominal cavity of Balb/C mice in a dose of 50 μg per mouse. After 2 weeks of the primary immunization, each mouse was boosted four times in two-week intervals using a dose of 50 μg of the same immunogen for each injection. Next, the activating splenocytes were fused with myeloma cells to generate hybridoma cell lines.

A hybridoma cell line having higher affinity to the recombinant protein listed as the undenatured amino acid sequence of SEQ ID NO:13 was screened from the aforementioned hybridoma cell lines. The screened hybridoma cell line could specifically recognize the undenatured amino acid sequences of SEQ ID NO:1 to SEQ ID NO:13.

The PTX3 mAb was purified from the culture medium of the screened hybridoma cell line via commercially available column. The amino acid sequences and their corresponding nucleic acid sequences of complementarity-determining regions (CDRs) of the heavy chain variable (VH) domain and the light chain variable (VL) domain of the PTX3 mAb were analyzed by Leadgene Biomedical, Inc. Taiwan. The VH domain had the amino acid sequences listed as SEQ ID NO:18, SEQ ID NO:19 and/or SEQ ID NO:21. The VL domain had the amino acid sequences listed as SEQ ID NO:22, SEQ ID NO:23 and/or SEQ ID NO:24. The amino acid sequence of the VH domain was the one listed as SEQ ID NO:34 or encoded by a nucleic acid sequence listed as SEQ ID NO:38. The amino acid sequence of the VL domain was the one listed as SEQ ID NO:36 or encoded by a nucleic acid sequence listed as SEQ ID NO:40.

In addition, the aforementioned PTX3 mAb was analyzed by commercially available mAb isotyping kit and confirmed that its isotype was IgG1k.

Example 2. Assessment of Affinity of PTX3 mAb

In this EXAMPLE, the affinity of PTX3 mAb of EXAMPLE 1 recognizing PTX3 recombinant protein was evaluated by conventional enzyme-linked immunosorbent assay (ELISA) kit.

Firstly, 5 μg/mL of PTX3 recombinant protein (representing a undenatured amino acid sequence listed as SEQ ID NO:14) or bovine serum albumin (BSA, as a control) was coated onto each well of a 96-well cell culture plate (Product No. 9018, Corning Costar), and reacted at 4° C. overnight. Next, the blocking solution [containing 3% non-fat milk in phosphate-buffered saline (PBS)] was added into wells, and blocked for 1 hour under room temperature (i.e. 4° C. to 40° C.). After removing the blocking solution, each well was rinsed with PBS, and then reacted with a primary antibody for 1 hour under room temperature (i.e. 4° C. to 40° C.), in which the primary antibody was PTX3 mAb of EXAMPLE 1 serially diluted in a concentration range of $2.44\times10^{-4}$ μg/mL to 1.00 μg/mL. And then, each well was washed by PBS for removing unconjugated PTX3 mAb, and reacted with secondary antibody under room temperature (i.e. 4° C. to 40° C.), in which the secondary antibody was anti-mouse IgG conjugated to horse peroxidase (HRP) (anti-mouse IgG-HRP). Afterward, tetramethylbenzidine (TMB) was added into each well for reaction over a time period, and then 0.1 M of sulfuric acid ($H_2SO_4$) solution for 10 minutes to stop the reaction. Subsequently, the absorbance at 450 nm of each well was measured by commercially available ELISA reader, and the results were shown in FIG. 1. Each value was obtained in triplicate. The reaction time of the secondary antibody could be carried out according to the manual of the manufacturer, which was well known by a person of ordinary skill in this art and unnecessary to recite in detail.

Reference was made to FIG. 1, which illustrated an affinity curve diagram of PTX3 mAb of Example 1 binding to PTX3 recombinant protein according to an embodiment of the present invention, in which a curve labeled by the symbol "●" denoted an affinity curve of PTX3 mAb to PTX3 recombinant protein, and a curve labeled by the symbol "■" denoted an affinity curve of PTX3 mAb to BSA.

As shown in FIG. 1, the PTX3 mAb of Example 1 exhibited a good affinity to PTX3 recombinant protein at a significantly low concentration of six 4-fold serial dilutions (i.e. $4^6$-fold serial dilution, and the final concentration of the antibody was equivalent to 0.244 ng/mL or 0.0016 pM).

In addition, the aforementioned ELISA kit also proved that the PTX3 mAb of Example 1 had high affinity to the PTX3 recombinant protein. Firstly, 10 µg/mL of PTX3 recombinant protein (representing a undenatured amino acid sequence listed as SEQ ID NO:14, dissolved in pH 7.2 PBS) was coated onto each well of a 96-well cell culture plate (Product No. 9018, Corning Costar), and reacted at 4° C. overnight. Next, the blocking solution (containing 3% BSA in PBS) was added into wells, and blocked for 1 hour under room temperature (i.e. 4° C. to 40° C.). After removing the blocking solution, each well was rinsed with PBS, and then reacted with a primary antibody for 1 hour under room temperature (i.e. 4° C. to 40° C.), in which the primary antibody was PTX3 mAb of EXAMPLE 1 serially diluted in a concentration range of 0.01 ng/mL to 1000 ng/mL. And then, each well was rinsed several times with PBST (i.e. PBS with Tween 20) for removing unconjugated PTX3 mAb, and reacted with secondary antibody under room temperature (i.e. 4° C. to 40° C.), in which the secondary antibody was anti-mouse IgG-HRP. Afterward, TMB was added into each well for reaction over a time period, and then added with 0.1 M of $H_2SO_4$ solution for 10 minutes to stop the reaction. Subsequently, the absorbance at 450 nm of each well was measured by commercially available ELISA reader, and the results were shown in FIG. 2. Each value was obtained in quadruplicate. The reaction time of the secondary antibody could be carried out according to the manual of the manufacturer, which was well known by a person of ordinary skill in this art and unnecessary to recite in detail.

Figure 2:
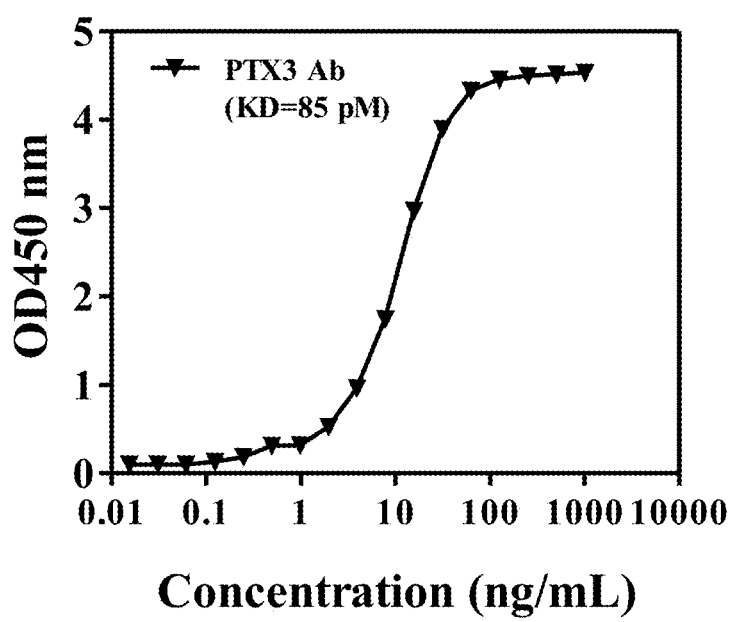
FIG. 2 illustrates an affinity curve diagram of PTX3 monoclonal antibody binding to PTX3 recombinant protein according to another embodiment of the present invention.

Reference was made to FIG. 2, which illustrated an affinity curve diagram of PTX3 mAb to PTX3 recombinant protein according to another embodiment of the present invention. As shown in FIG. 2, the PTX3 mAb of Example 1 exhibited a higher affinity to PTX3 recombinant protein (i.e. antigen) with a dissociation constant (KD) of 85 pM, for being applied to PTX3 detection kit.

Figure 3:
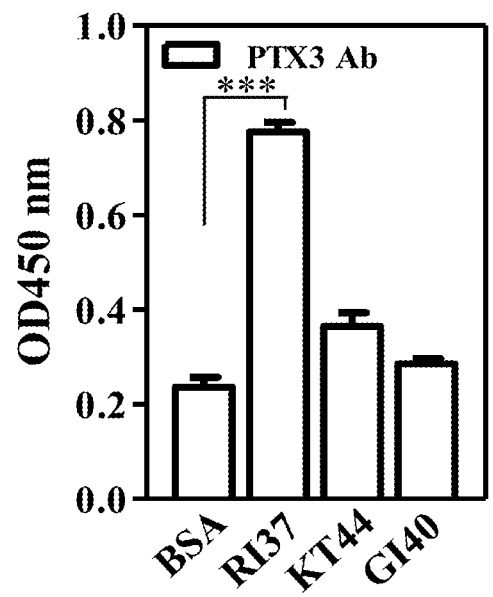
FIGS. 3 and 4 illustrate epitope mapping diagrams of PTX3 monoclonal antibody binding to various fragments of PTX3 recombinant protein according to an embodiment of the present invention.

In addition, in other experiments, the PTX3 mAb could specifically bind to the $200^{th}$ to $359^{th}$ amino acid residues (such as the undenatured amino acid sequence of SEQ ID NO:13; the result not shown) or the $200^{th}$ to $236^{th}$ amino acid residues (such as the undenatured amino acid sequence of SEQ ID NO:12; the result shown in FIG. 3) of PTX3 recombinant protein.

Example 3. Assessment of Binding Region of PTX3 and PTX3 Monoclonal Antibody

1. Analysis of Epitope Mapping Region of PTX3 Recognized by PTX3 Monoclonal Antibody of Example 1

In this EXAMPLE, the epitope mapping region of PTX3 recognized by PTX3 mAb was evaluated by conventional ELISA kit.

In this EXAMPLE, the same method as EXAMPLE 1 was used to map a narrower region of PTX3 binding to PTX3 mAb, except that 200 µg/mL of PTX3 recombinant protein (representing a undenatured amino acid sequence listed as SEQ ID NOs:12, 16 or 17, dissolved in 0.1 M sodium bicarbonate solution, pH 8) or BSA (as a control) was coated onto each well of a 96-well cell culture plate, and reacted at 4° C. overnight. Next, the blocking solution (containing 1% BSA in PBS) was added into wells, and blocked for 1 hour under room temperature (i.e. 4° C. to 40° C.). After removing the blocking solution, each well was rinsed with PBS, and then reacted with PTX3 mAb of EXAMPLE 1 (a concentration of 125 ng/mL) for 2 hours under room temperature (i.e. 4° C. to 40° C.). And then, each well was rinsed several times with PBS for removing unconjugated PTX3 mAb, and reacted with secondary antibody (anti-mouse IgG-HRP at a dilution of 1:5000) under room temperature (i.e. 4° C. to 40° C.) for 1 hour. Afterward, TMB was added into each well for reaction over a time period, and then added with 0.1 M of $H_2SO_4$ solution for 10 minutes to stop the reaction. Subsequently, the absorbance at 450 nm of each well was measured by commercially available ELISA reader, and the results were shown in FIG. 3. Each value was obtained in triplicate.

Reference was made to FIG. 3, which illustrated an epitope mapping diagram of PTX3 mAb binding to various fragments of PTX3 recombinant protein according to an embodiment of the present invention, in which RI37 referred to a fragment of PTX3 recombinant protein listed as SEQ ID NO:12, KT44 referred to a fragment of PTX3 recombinant protein listed as SEQ ID NO:16, GI40 referred to a fragment of PTX3 recombinant protein listed as SEQ ID NO:17, and asterisks (***) indicated a statistically significant difference compared to the control group (i.e. BSA group) ($p<0.001$).

The result of FIG. 3 was shown that the PTX3 mAb of Example 1 binding to the fragment of PTX3 recombinant protein listed as SEQ ID NO:12 exhibited a higher affinity to other fragments of PTX3 recombinant protein, and it had a statistical significance.

Figure 4:
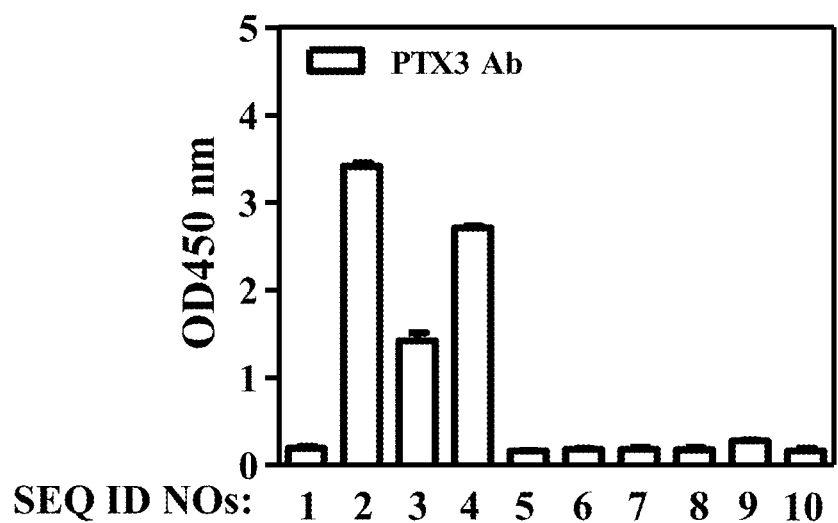

Reference was made to FIG. 4, which illustrated an epitope mapping diagram of PTX3 mAb binding to various fragments of PTX3 recombinant protein according to an embodiment of the present invention, in which the horizontal axis showed the groups using various fragments of PTX3 recombinant protein listed as SEQ ID NOs:1 to 10.

The result of FIG. 4 was shown that the PTX3 mAb of Example 1 binding to the fragment of PTX3 recombinant protein listed as SEQ ID NOs:1 to 5 or SEQ ID NOs:2 to 4 exhibited a relatively higher affinity to other fragments of PTX3 recombinant protein, in which PTX3 recombinant proteins listed as SEQ ID NOs:2 to 4 corresponded to the $203^{th}$ to $217^{th}$ amino acid residues of PTX3 recombinant protein, or to the amino acid sequence listed as SEQ ID NO:11, indicating that the epitope mapping region of PTX3 recognized by PTX3 mAb was located in a region including the amino acid sequence of SEQ ID NOs:2 to 4 or SEQ ID NO:11.

2. Differences of Epitope Mapping Regions of PTX3 between PTX3 Monoclonal Antibody of Example 1 and Commercial PTX3 Monoclonal Antibody In this EXAMPLE, the same method as EXAMPLE 3 was used to evaluate epitope mapping regions of PTX3 between PTX3 mAb of EXAMPLE 1 and commercial PTX3 mAb (ab90806, abcam plc., U.K.), and the results were shown in FIG. 5. Each value was obtained in triplicate.

Figure 5:
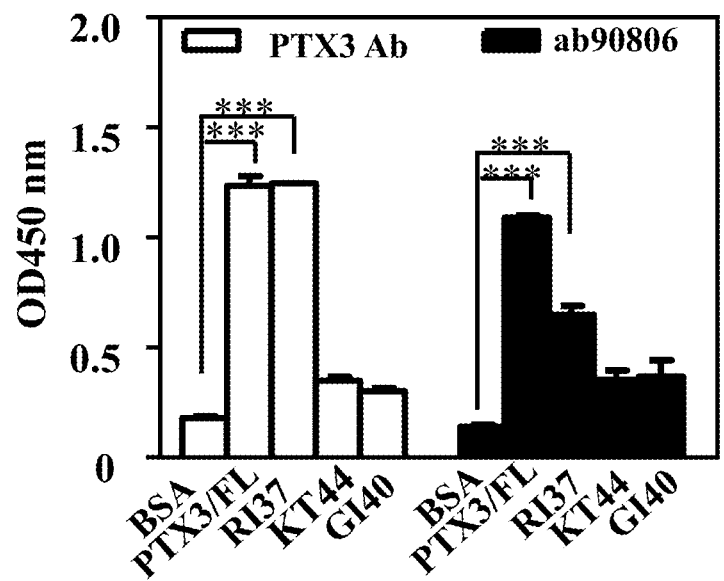
FIG. 5 illustrates an epitope mapping diagram of PTX3 monoclonal antibody binding to various fragments of PTX3 recombinant protein according to an embodiment of the present invention compared to commercial PTX3 monoclonal antibody.

Reference was made to FIG. 5, which illustrated an epitope mapping diagram of PTX3 mAb binding to various fragments of PTX3 recombinant protein according to an embodiment of the present invention compared to commercial PTX3 mAb, in which PTX3/FL referred to a full-length fragment of PTX3 recombinant protein listed as SEQ ID NO:15, RI37 referred to a fragment of PTX3 recombinant protein listed as SEQ ID NO:12, KT44 referred to a fragment of PTX3 recombinant protein listed as SEQ ID NO:16, GI40 referred to a fragment of PTX3 recombinant protein listed as SEQ ID NO:17, and asterisks (***) indicated a statistically significant difference compared to the control group (i.e. BSA group) ($p<0.001$)

The result of FIG. 5 was shown that both of the PTX3 mAb of Example 1 and the commercial PTX3 mAb (ab90806) binding to PTX3/FL (SEQ ID NO:15) exhibited a comparably high affinity; however, the PTX3 mAb of Example 1 binding to the fragment RI37 of PTX3 recombinant protein (SEQ ID NO:12) exhibited a relatively higher affinity to the commercial PTX3 mAb (ab90806). It had a statistical significance on the epitope mapping regions of PTX3 between the PTX3 mAb of Example 1 and the commercial PTX3 mAb (ab90806).

Example 4. In Vitro Evaluation of PTX3 Binding to its Receptor Affected by PTX3 Monoclonal Antibody PTX3 mAb could competitively bind to PTX3 receptor binding region or its surrounding region of PTX3, so as to specifically inhibit or alleviate the opportunity of PTX3 binding to PTX3 receptor. In this EXAMPLE, CD44 served as an example of the PTX3 receptor, and a competitive binding assay was used to evaluate the effect of inhibition of PTX3 binding to PTX3 receptor.

This EXAMPLE demonstrated that the PTX3 mAb of EXAMPLE 1 could neutralize PTX3 and prevent PTX3 from binding to the PTX3 receptor binding region or its surrounding region of PTX3 receptor (such as CD44).

More particularly, in this EXAMPLE, the competitive binding assay was the same as EXAMPLE 1 except that 10 μg/mL of PTX3 receptor [for example, N-terminal recombinant protein of CD44 (N-terminal the first to $220^{th}$ amino acid residues of CD44, dissolved in PBS, pH 7.2; Sino Biological Inc., Beijing, China)] was coated onto each well of a 96-well cell culture plate, and reacted at 4° C. overnight. Next, the blocking solution (containing 3% non-fat milk in PBS) was added into wells, and blocked for 1 hour under room temperature (i.e. 4° C. to 40° C.).

During performing the competitive binding assay, the HRP-conjugated PTX3 (such as the undenatured amino acid sequence of SEQ ID NO:14, HRP-PTX3 in a concentration of 5 μg/mL) prereacted with various concentrations (1 μg/mL or 2 μg/mL) of PTX3 mAb of EXAMPLE 1 for 1 hour under room temperature (i.e. 4° C. to 40° C.), thereby forming a pre-reactant.

After removing the blocking solution, each well was rinsed with PBS, and then reacted with the aforementioned pre-reactant for 2 hours under room temperature (i.e. 4° C. to 40° C.). And then, each well was rinsed with PBS for removing the unconjugated pre-reactant, and TMB was added into each well for reaction over a time period, and then added with 0.1 M of $H_2SO_4$ solution for 10 minutes to stop the reaction. Subsequently, the absorbance at 450 nm of each well was measured by commercially available ELISA reader, and the results were shown in FIG. 6. Each value was obtained in quadruplicate.

Figure 6:
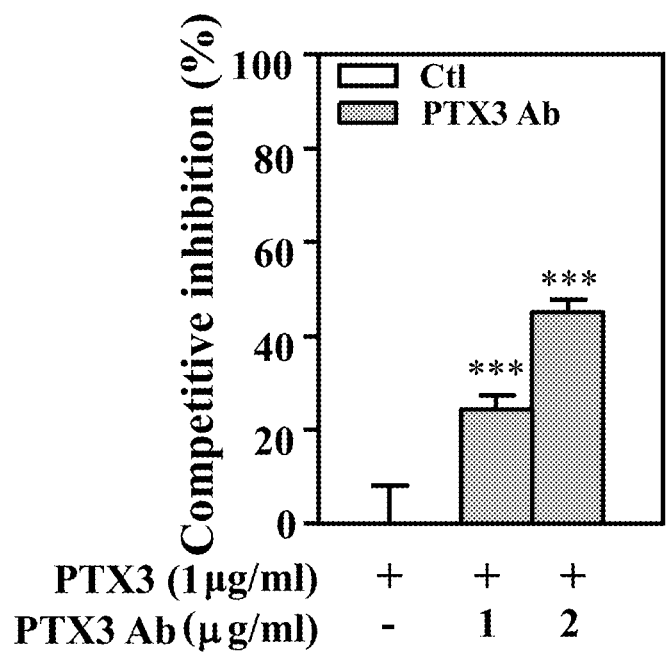
FIG. 6 illustrates a competitive inhibition diagram of the binding of PTX3 recombinant protein and PTX3 receptor hindered by PTX3 monoclonal antibody of EXAMPLE 1 according to an embodiment of the present invention.
Figure 7A:
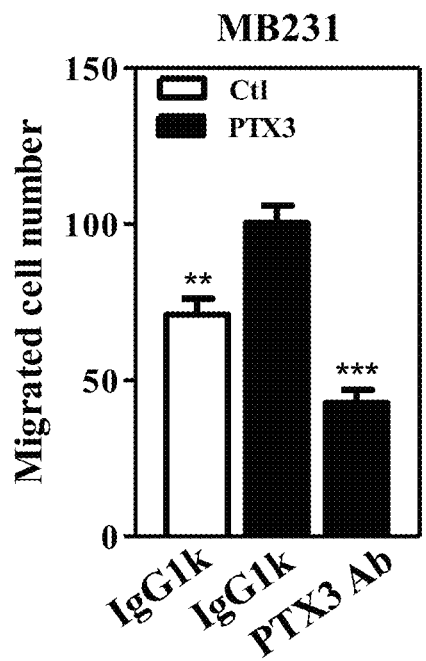
FIGS. 7A to 7C illustrate bar diagrams of migrated cell numbers (FIG. 7A), invasive cell numbers (FIG. 7B) and cell sphere numbers (FIG. 7C) of the breast cancer cell line MDA-MB231 inhibited by PTX3 monoclonal antibody of EXAMPLE 1 according to an embodiment of the present invention.
Figure 7B:
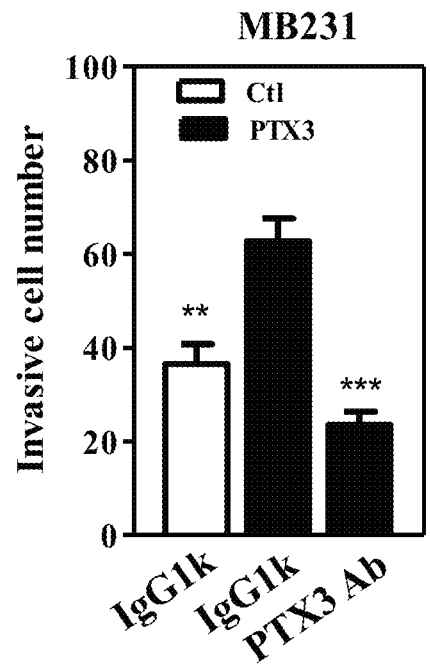
Figure 7C:
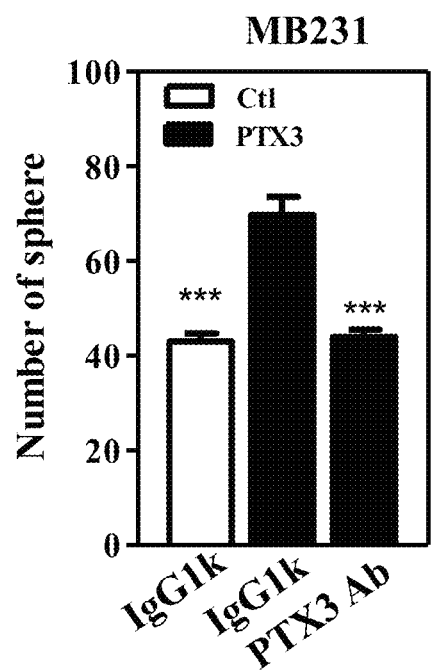
Figure 8A:
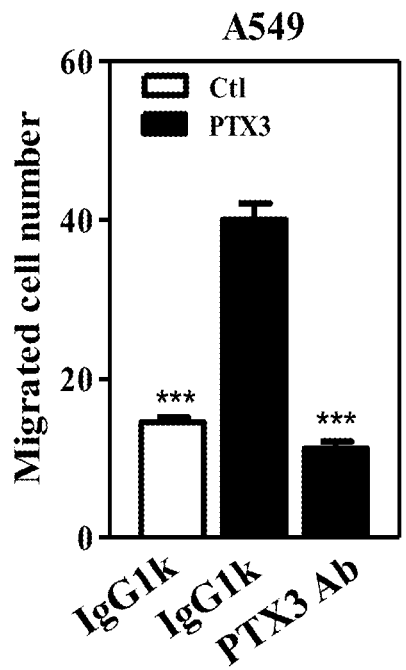
FIGS. 8A to 8C illustrate bar diagrams of migrated cell numbers (FIG. 8A), invasive cell numbers (FIG. 8B) and cell sphere numbers (FIG. 8C) of the lung cancer cell line A549 inhibited by PTX3 monoclonal antibody of EXAMPLE 1 according to an embodiment of the present invention.
Figure 8B:
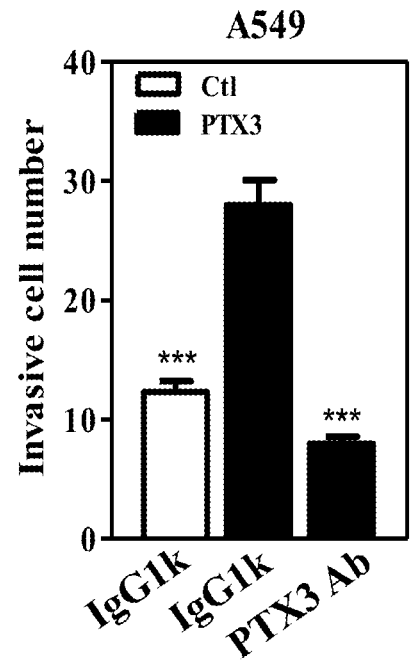
Figure 8C:
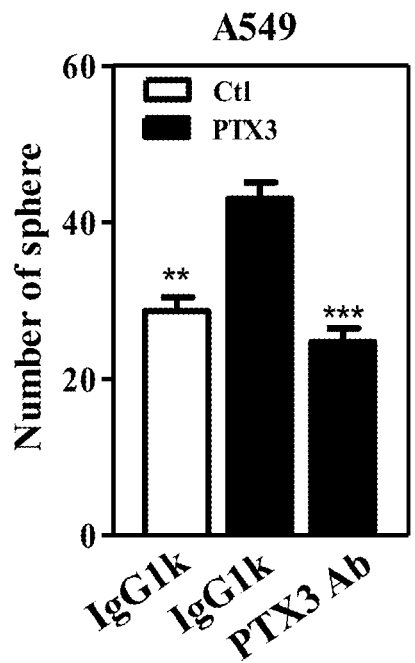
Figure 9A:
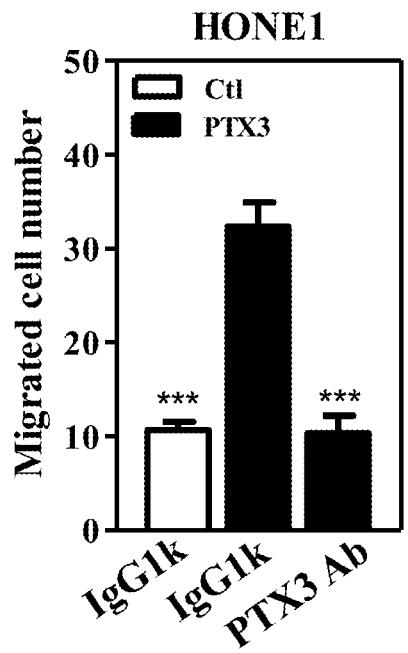
FIGS. 9A to 9C illustrate bar diagrams of migrated cell numbers (FIG. 9A), invasive cell numbers (FIG. 9B) and cell sphere numbers (FIG. 9C) of the NPC cell line HONE1 inhibited by PTX3 monoclonal antibody of EXAMPLE 1 according to an embodiment of the present invention.
Figure 9B:
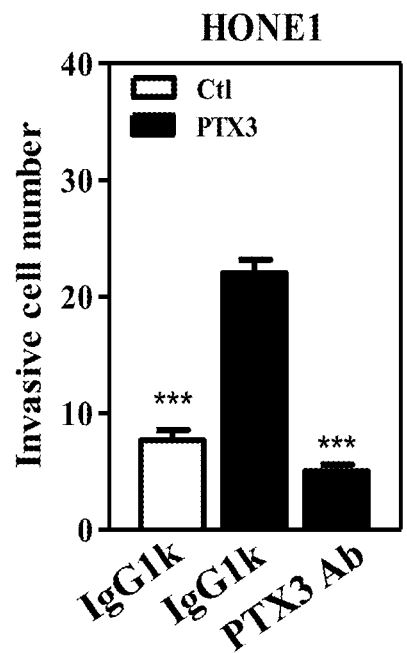
Figure 9C:
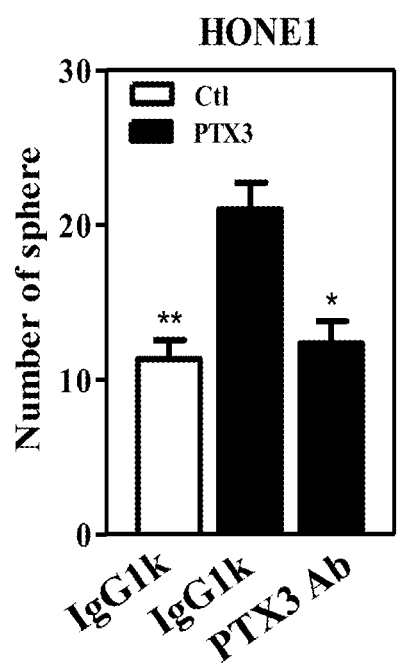
Figure 10A:
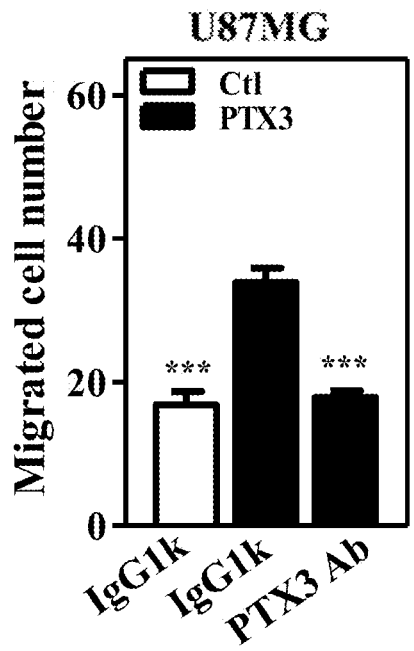
FIGS. 10A to 10C illustrate bar diagrams of migrated cell numbers (FIG. 10A), invasive cell numbers (FIG. 10B) and cell sphere numbers (FIG. 10C) of the GBM cell line U87MG inhibited by PTX3 monoclonal antibody of EXAMPLE 1 according to an embodiment of the present invention.
Figure 10B:
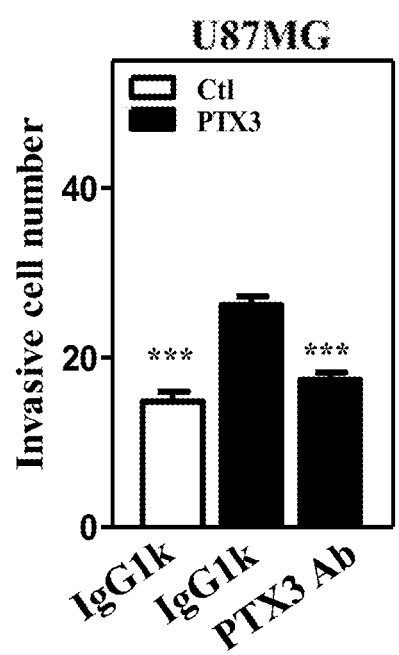
Figure 10C:
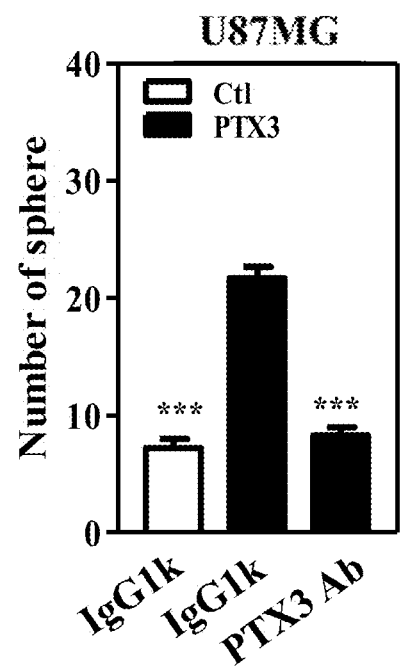

Reference was made to FIG. 6, which illustrated a competitive inhibition diagram of the binding of PTX3 recombinant protein and PTX3 receptor hindered by PTX3 mAb of EXAMPLE 1 according to an embodiment of the present invention, in which the vertical axis referred to a competitive inhibition rate (%), and the symbol "+" or "−" below the horizontal axis referred to addition of specific ingredient or not during the binding reaction. The first bar from the left side of the FIG. 6 referred to the control group (only PTX3 recombinant protein without PTX3 mAb), and three asterisks (***) indicated a statistically significant difference compared to the control group ($p<0.001$).

The result of FIG. 6 was shown that, based on the data of the first bar from the left side of the FIG. 6 (the control group) as 0% of competitive inhibition rate, the competitive inhibition rate (%) that was resulted from the PTX3 mAb of Example 1 pre-reacted with the PTX3 recombinant protein and reacted with CD44 receptor could exhibit a dose-dependent relation to a concentration of the PTX3 mAb, other fragments of PTX3 recombinant protein, and it had a statistical significance, indicating that the PTX3 mAb of EXAMPLE 1 could neutralize PTX3 and prevent PTX3 from binding to the binding region or its surrounding region of CD44.

Example 5. Assessment of Activities of Cancer Cells Influenced by PTX3 Monoclonal Antibody Breast cancer, lung cancer, nasopharyngeal cancer and glioblastoma multiforme (GBM) belonged to malignant tumors, and these cancer cells had activities of migration, invasion, cancer stemness and the like. In this Example, the influence of the PTX3 mAb of EXAMPLE 1 on the activities of the cancer cells was evaluated in a human breast cancer cell line [MDA-MB231, Deposit Accession Number: BCRC 60425 deposited in Bioresource Collection and Research Center (BCRC), Taiwan of the Food Industry Research and Development Institute, P.O. Box 246, Hsinchu, Taiwan 300, Republic of China, or Deposit Accession Number: ATCC HTB-26; abbreviated hereinafter as MB231], a human lung cancer cell line A549 (Deposit Accession Number: BCRC 60074 deposited in BCRC; or ATCC CCL-185), a human nasopharyngeal cancer (NPC) cell line HONE1 (*Int. J. Cancer.* 1990 Jan. 15; 45(1):83-9; *Proc. Natl. Acad. Sci. USA*, Vol. 86, pp. 9524-9528, December 1989), human glioblastoma multiforme (GBM) cell line U87MG (ATCC HTB-14 or BCRC 60360) and so on.

1. Evaluation of Influence of PTX3 mAb on Migration of Cancer Cells

In the migration test, a cell density $1\times10^5$ cells/well of the aforementioned cancer cells were seeded into each upper insert (with 8 μm pores in the bottom) of 24-well Boyden chamber for 3 hours of cultivation. And then, the medium in each upper insert was replaced by serum-free medium, and the medium in each lower well was added with serum-free medium containing 0.2 μg/mL of PTX3 recombinant protein (such as the undenatured amino acid sequence listed as SEQ ID NO:14), as well as 0.4 μg/mL of PTX3 mAb or the control antibody (IgG1k).

The cells inside each upper insert were wiped with cotton swabs and removed after 16 hours of cultivation. Remaining cells that had migrated to the bottom of the insert membrane were stained by 4',6-diamidino-2-phenylindole (DAPI; Invitrogen) and calculated in cell numbers under fluorescence microscopy with 200-fold magnification. The results were shown in FIGS. 7A, 8A, 9A and 10A.

Reference was made to FIGS. 7A, 8A, 9A and 10A, which illustrated respectively bar diagrams of migrated cell numbers of the breast cancer cell line MB231 (FIG. 7A), the lung cancer cell line A549 (FIG. 8A), the NPC cell line HONE1 (FIG. 9A) and the GBM cell line U87MG (FIG. 10A) inhibited by PTX3 mAb of EXAMPLE 1 according to an embodiment of the present invention. All data of these examples were obtained from triplicates at each time point and each sample as mean plus or minus the averaged standard deviation. All data were analyzed in one way ANOVA. In this example, two asterisks () indicated the data having a statistically significant difference ($p<0.01$), and three asterisks (*) indicated the data having a statistically significant difference ($p<0.001$).

The results of FIGS. 7A, 8A, 9A and 10A were shown that, compared to the data of the control antibody IgG1k, the PTX3 mAb of Example 1 could significantly inhibit the migrated cell numbers of the breast cancer cell line MB231, the lung cancer cell line A549, the NPC cell line HONE1 and the GBM cell line U87MG, and their differences had statistical significances.

2. Evaluation of Influence of PTX3 mAb on Invasion of Cancer Cells

In the invasion test, the bottom (with 8 μm pores) of the upper insert was pre-coated with the basement membrane matrix (product name: matrigel, purchased from BD Bioscience), and a cell density $1\times10^5$ cells/well of the aforementioned cancer cells were seeded into each upper insert of 24-well Boyden chamber for 3 hours of cultivation. And then, the medium in each upper insert was replaced by serum-free medium, and the medium in each lower well was added with serum-free medium containing 0.2 μg/mL of PTX3 recombinant protein (such as the undenatured amino acid sequence listed as SEQ ID NO:14), as well as 0.4 μg/mL of PTX3 mAb or the control antibody (IgG1k).

The cells inside each upper insert were wiped with cotton swabs and removed after 16 hours of cultivation. Remaining cells that had migrated to the bottom of the insert membrane were stained by DAPI (Invitrogen) and calculated in cell numbers under fluorescence microscopy with 200-fold magnification. The results were shown in FIGS. 7B, 8B, 9B and 10B.

Reference was made to FIGS. 7B, 8B, 9B and 10B, which illustrated respectively bar diagrams of invasive cell numbers of the breast cancer cell line MB231 (FIG. 7B), the lung cancer cell line A549 (FIG. 8B), the NPC cell line HONE1 (FIG. 9B) and the GBM cell line U87MG (FIG. 10B) inhibited by PTX3 mAb of EXAMPLE 1 according to an embodiment of the present invention. In this example, two asterisks () indicated the data having a statistically significant difference ($p<0.01$), and three asterisks (*) indicated the data having a statistically significant difference ($p<0.001$).

The results of FIGS. 7B, 8B, 9B and 10B were shown that, compared to the data of the control antibody IgG1k, the PTX3 mAb of Example 1 could significantly inhibit the invasive cell numbers of the breast cancer cell line MB231, the lung cancer cell line A549, the NPC cell line HONE1 and the GBM cell line U87MG, and their differences had statistical significances.

3. Evaluation of Influence of PTX3 mAb on Cancer Stemness of Cancer Cells

The aforementioned cancer cells had cancer stemness, and they could form spheres co-cultured with the PTX3 recombinant protein.

In the cell sphere test, the aforementioned cancer cells were cultured in RPMI-1640 cell medium [(supplemented with 10% Fetal Bovine Serum (FBS), 50-100 μg/mL of streptomycin and 50-100 U/mL of penicillin] added with 0.2 μg/mL of PTX3 recombinant protein (such as the undenatured amino acid sequence listed as SEQ ID NO:14), as well as 0.4 μg/mL of PTX3 mAb or the control antibody (IgG1k). Those cells were incubated at 37° C. in humidified 5% $CO_2$, the conditions of which were well known by one skilled in the art rather than being recited in detail herein.

Next, the cell density $5\times10^3$ cells/well of the aforementioned cancer cells were inoculated into multi-well plates with ultra-low attachment surface (Corning Inc.), cultured in serum-free medium DMEM/F12 (Gibco) [containing B27 (Invitrogen), 20 ng/mL of epidermal growth factor (EGF; Abcam) and 10 ng/mL of basic Fibroblast Growth Factor (bFGF; Peprotech)]. After 2 weeks of cultivation, the cell sphere numbers were observed by optical microscopy. The results were shown in FIGS. 7C, 8C, 9C and 10C.

Reference was made to FIGS. 7C, 8C, 9C and 10C, which illustrated respectively bar diagrams of cell sphere numbers of the breast cancer cell line MB231 (FIG. 7C), the lung cancer cell line A549 (FIG. 8C), the NPC cell line HONE1 (FIG. 9C) and the GBM cell line U87MG (FIG. 10C) inhibited by PTX3 mAb of EXAMPLE 1 according to an embodiment of the present invention. In this example, two asterisks () indicated the data having a statistically significant difference ($p<0.01$), and three asterisks (*) indicated the data having a statistically significant difference ($p<0.001$).

The results of FIGS. 7C, 8C, 9C and 10C were shown that, compared to the data of the control antibody IgG1k, the PTX3 mAb of Example 1 could significantly inhibit the cell sphere numbers of the breast cancer cell line MB231, the lung cancer cell line A549, the NPC cell line HONE1 and the GBM cell line U87MG, and their differences had statistical significances.

4. Evaluation of Influence of PTX3 mAb of Example 1 on Cancer Activities of Cancer Cells In this EXAMPLE, the same method as EXAMPLE 2 was used to evaluate the effect of activities of cancer cells inhibited by the PTX3 mAb of EXAMPLE 1 or commercial PTX3 mAb (ab90806, abcam plc., U.K.), and the results were shown in FIGS. 11A to 14C.

Figure 11A:
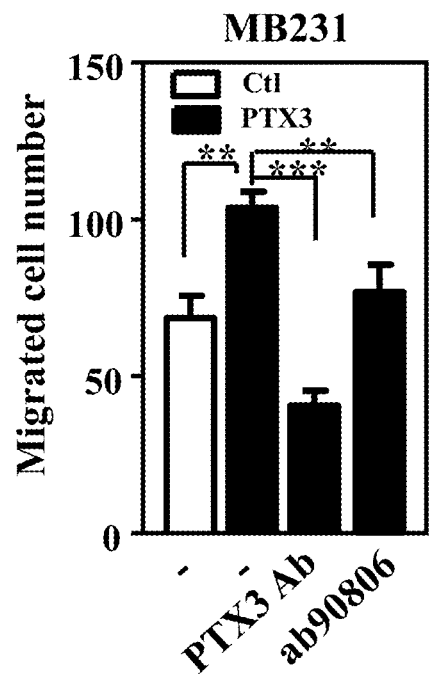
FIGS. 11A to 11B illustrate respectively bar diagrams of migrated cell numbers (FIG. 11A) and invasive cell numbers (FIG. 11B) of the breast cancer cell line MDA-MB231 inhibited by PTX3 monoclonal antibody of EXAMPLE 1 according to an embodiment of the present invention.
Figure 12A:
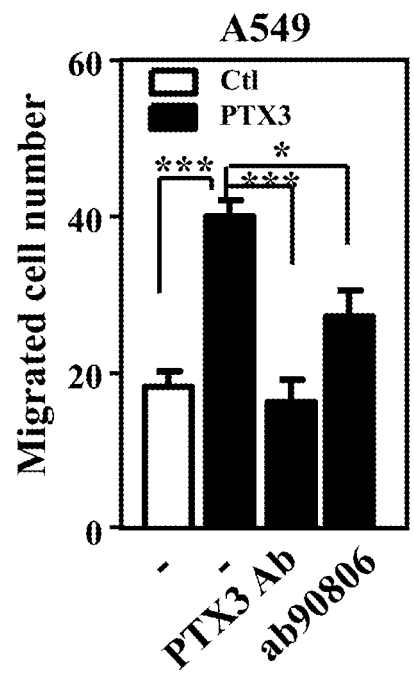
FIGS. 12A to 12B illustrate respectively bar diagrams of migrated cell numbers (FIG. 12A) and invasive cell numbers (FIG. 12B) of the lung cancer cell line A549 inhibited by PTX3 monoclonal antibody of EXAMPLE 1 according to an embodiment of the present invention.
Figure 13A:
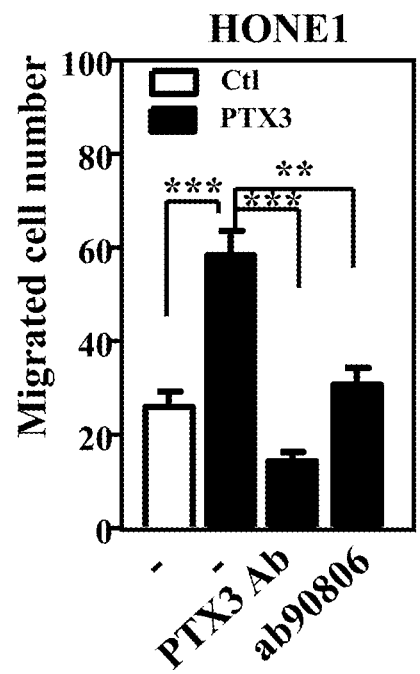
FIGS. 13A to 13B illustrate respectively bar diagrams of cell sphere numbers of the NPC cell line HONE1 inhibited by PTX3 monoclonal antibody of EXAMPLE 1 according to an embodiment of the present invention.

Reference was made to FIGS. 11A, 12A and 13A, which illustrated respectively bar diagrams of migrated cell numbers of the breast cancer cell line MB231 (FIG. 11A), the lung cancer cell line A549 (FIG. 12A) and the NPC cell line HONE1 (FIG. 13A) inhibited by PTX3 mAb of EXAMPLE 1 or the commercial PTX3 mAb according to an embodiment of the present invention. In this example, one asterisk (*) indicated the data having a statistically significant difference ($p<0.05$), two asterisks () indicated the data having a statistically significant difference ($p<0.01$), and three asterisks (*) indicated the data having a statistically significant difference ($p<0.001$).

The results of FIGS. 11A, 12A and 13A were shown that, compared to the data of the control antibody IgG1k, the PTX3 mAb of Example 1 and the commercial PTX3 mAb (ab90806) could significantly inhibit the migrated cell numbers of the breast cancer cell line MB231, the lung cancer cell line A549 and the NPC cell line HONE1; however, the PTX3 mAb of Example 1 could more significantly inhibit cancer cell migration than the commercial PTX3 mAb (ab90806), and their differences had statistical significances.

Figure 11B:
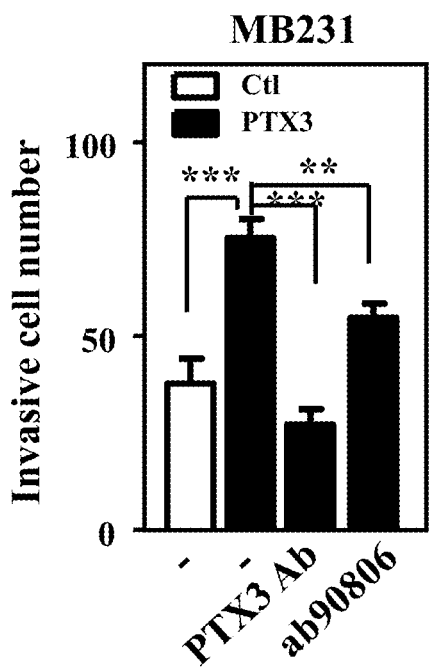
Figure 12B:
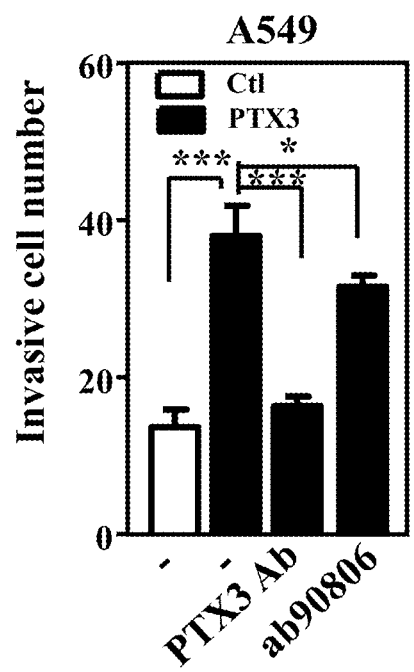
Figure 13B:
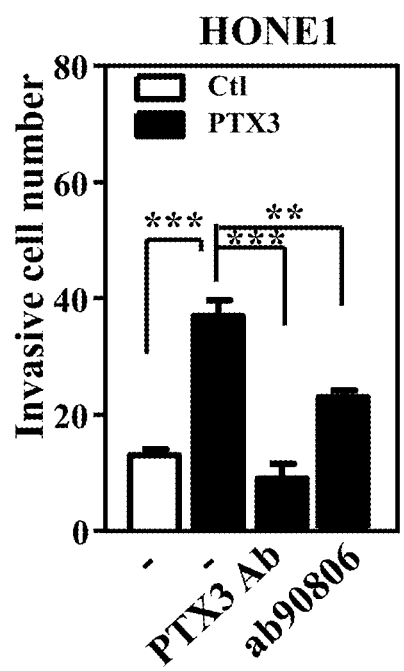

Reference was made to FIGS. 11B, 12B and 13B, which illustrated respectively bar diagrams of invasive cell numbers of the breast cancer cell line MB231 (FIG. 11B), the lung cancer cell line A549 (FIG. 12B) and the NPC cell line HONE1 (FIG. 13B) inhibited by PTX3 mAb of EXAMPLE 1 or the commercial PTX3 mAb according to an embodiment of the present invention. In this example, one asterisk (*) indicated the data having a statistically significant difference ($p<0.05$), two asterisks () indicated the data having a statistically significant difference ($p<0.01$), and three asterisks (*) indicated the data having a statistically significant difference ($p<0.001$).

The results of FIGS. 11B, 12B and 13B were shown that, compared to the data of the control antibody IgG1k, the PTX3 mAb of Example 1 and the commercial PTX3 mAb (ab90806) could significantly inhibit the invasive cell numbers of the breast cancer cell line MB231, the lung cancer cell line A549 and the NPC cell line HONE1; however, the PTX3 mAb of Example 1 could more significantly inhibit cancer cell invasion than the commercial PTX3 mAb (ab90806), and their differences had statistical significances.

Figure 14A:
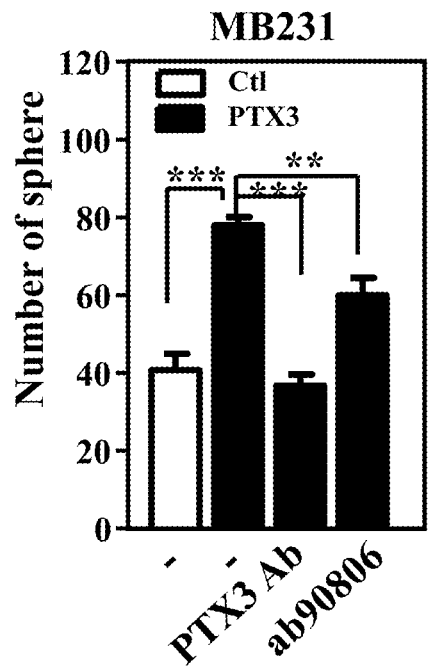
FIGS. 14A to 14C illustrate respectively bar diagrams of cell sphere numbers of the breast cancer cell line MDA-MB231 (FIG. 14A), the lung cancer cell line A549 (FIG. 14B), the NPC cell line HONE1 (FIG. 14C) inhibited by PTX3 monoclonal antibody of EXAMPLE 1 according to an embodiment of the present invention.
Figure 14B:
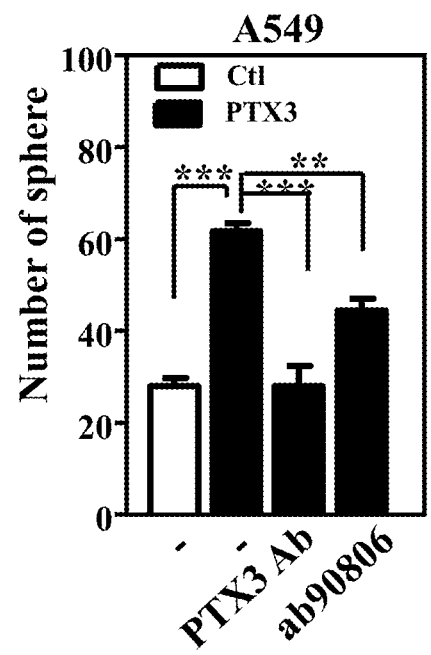
Figure 14C:
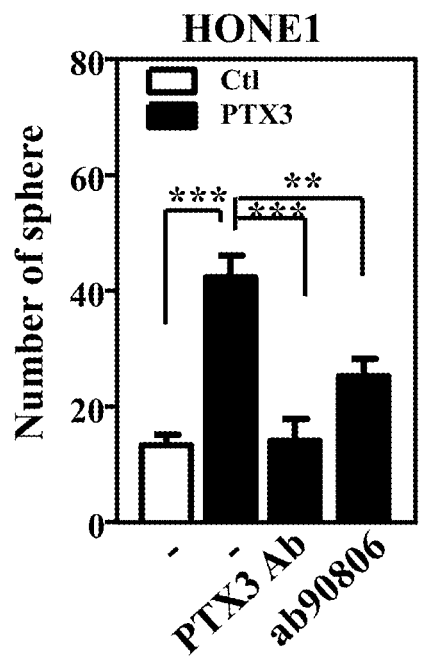

Reference was made to FIGS. 14A, 14B and 14C, which illustrated respectively bar diagrams of cell sphere numbers of the breast cancer cell line MB231 (FIG. 14A), the lung cancer cell line A549 (FIG. 14B) and the NPC cell line HONE1 (FIG. 14C) inhibited by PTX3 mAb of EXAMPLE 1 or the commercial PTX3 mAb according to an embodiment of the present invention. In this example, two asterisks () indicated the data having a statistically significant difference (p<0.01), and three asterisks (*) indicated the data having a statistically significant difference (p<0.001).

The results of FIGS. 14A, 14B and 14C were shown that, compared to the data of the control antibody IgG1k, the PTX3 mAb of Example 1 and the commercial PTX3 mAb (ab90806) could significantly inhibit the cell sphere numbers of the breast cancer cell line MB231, the lung cancer cell line A549 and the NPC cell line HONE1; however, the PTX3 mAb of Example 1 could more significantly inhibit or alleviate cell sphere numbers than the commercial PTX3 mAb (ab90806), and their differences had statistical significances.

Example 6. Evaluation of In Vivo Growth and Metastasis of Tumors Affected by PTX3 Monoclonal Antibody 1. Evaluation of PTX3 Monoclonal Antibody of EXAMPLE 1 Affecting Inhibition of In Vivo Growth and Metastasis of Orthotopically Xenografted Breast Cancers In this Example, human cancer cell line was orthotopically inoculated into the mammary fat pad of immunodeficient mice. After the formation of tumors, PTX3 mAb of EXAMPLE 1 was injected into these mice, thereby evaluating the treating effect of tumors inhibited or alleviated by PTX3 mAb of EXAMPLE 1.

Firstly, MB231-Luc2 cells [MB231 cells were human breast cancer cells without expression of estrogen receptor (ER) α and ERβ; and Luc2 gene expressed luciferase] were orthotopically inoculated into the mammary fat pad of NOD-SCID mice (purchased from BioLASCO Taiwan Co., Ltd.). Once tumors reached an average volume of 80 mm$^3$, PTX3 antibody (8 mg/kg body weight) of EXAMPLE 1 or control antibody (IgG1K, 8 mg/kg body weight) was intraperitoneally injected to the experimental mice once a week. The result was shown in FIGS. 15A to 15B. FIG. 15B was an in vivo imaging photographs on the 11$^{th}$ week after inoculating the breast cancer cells MB231-Luc2 cells, in which the in vivo imaging picture was obtained by commercially in vivo bioluminescent imaging system [for example, non-invasive 3D in vivo imaging system (IVIS system), PerkinElmer] for observing the size of tumors, and the radiance regions referred to the tumors formed from MB231-Luc2 cells in mice. Later, all mice were scarified, the tumor sizes in mice were measured and calculated by the formula (I):

$$V=(w \times l^2) \times 0.52 \quad (I)$$

In the formula (I), "l" was the length and "w" was the width of the tumor.

Figure 15A:
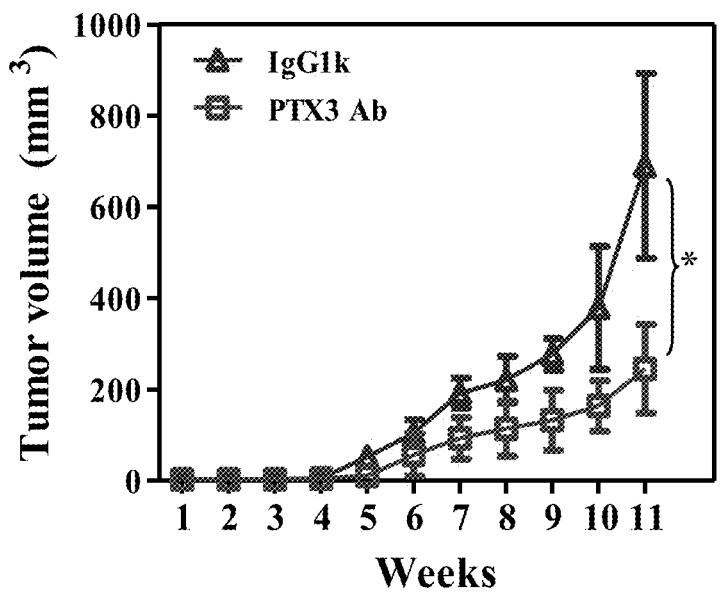
FIGS. 15A to 15B illustrate results of tumor size (FIG. 15A) and tumor metastasis (FIG. 15B) of orthotopically xenografted breast cancer cells MDA-MB231 of mice inhibited by PTX3 monoclonal antibody of EXAMPLE 1 according to an embodiment of the present invention.
Figure 15B:
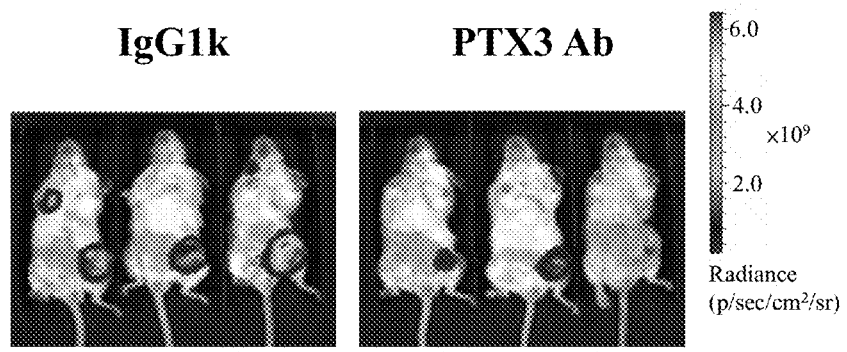

Reference was made to FIGS. 15A and 15B, which illustrated respectively the results of tumor size (FIG. 15A) and tumor metastasis (FIG. 15B) of orthotopically xenografted breast cancer cells MDA-MB231 of mice inhibited by PTX3 mAb of the control antibody according to an embodiment of the present invention. All data of FIG. 15A were obtained from hexaplicates at each time point and each sample as mean plus or minus the averaged standard deviation. In this example, one asterisk (*) indicated the data having a statistically significant difference (p<0.05).

The results of FIGS. 15A and 15B were shown that, compared to the data of the control antibody IgG1k, the PTX3 mAb of Example 1 could significantly inhibit the tumor size and tumor metastasis of the breast cancer cell line MB231 orthotopical xenograft, and the differences had statistical significances.

2. Evaluation of PTX3 Monoclonal Antibody of Example 1 Affecting Inhibition of In Vivo Growth and Metastasis of Orthotopically Allografted Breast Cancers In this Example, mouse cancer cell line was orthotopically inoculated into the mammary fat pad of immunocompetent mice. After the formation of tumors and establishment of tri-negative breast cancer (TNBC) model, PTX3 mAb of EXAMPLE 1 was adminstered into these mice, thereby evaluating the treating effect of tumors inhibited or alleviated by PTX3 mAb of EXAMPLE 1.

Firstly, 1×10$^6$ breast cancer cells 4T1 (ATCC®CRL-2539™), which were mouse breast cancer cell line transfected with plasmid containing Luc2 gene and expressing ERβ but not ERα, were orthotopically inoculated as orthotopical allograft into the mammary fat pad of wild-type BALB/c female mice (six to eight weeks old, purchased from BioLASCO Taiwan Co., Ltd.). Once tumors reached an average volume of 50 mm$^3$, PTX3 antibody (10 mg/kg body weight) of EXAMPLE 1 or control antibody (IgG1K, 10 mg/kg body weight) was administered to the mice once a week. The tumor sizes and metastasis in mice were observed by in vivo bioluminescent imaging system. And then, all mice were scarified, the tumor sizes in mice were measured and calculated by the above formula (I).

Figure 16A:
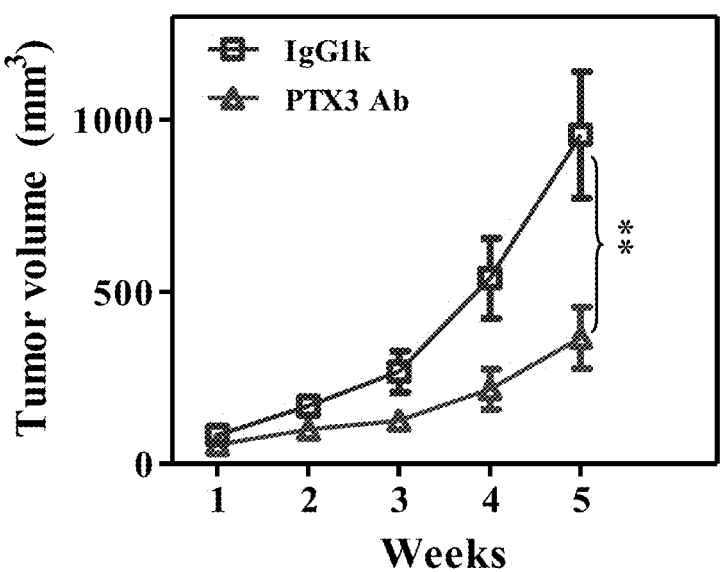
FIGS. 16A and 16B illustrate respectively results of tumor size (FIG. 16A) and tumor metastasis (FIG. 16B) of orthotopically allografted breast cancer cells 4T1 of mice inhibited by PTX3 monoclonal antibody of the control antibody or a control antibody with the same isotype according to an embodiment of the present invention.
Figure 16B:
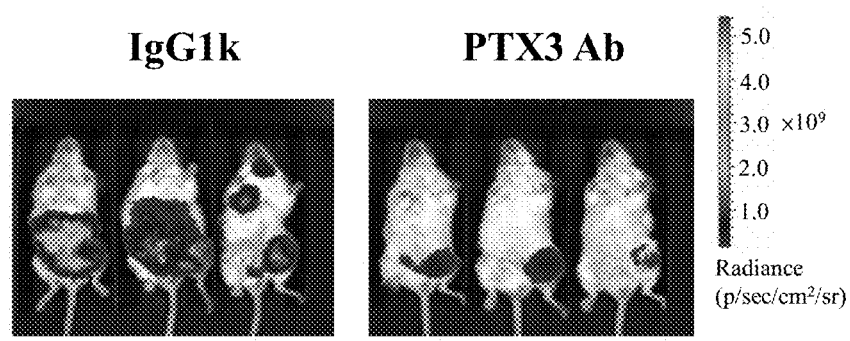

Reference was made to FIGS. 16A and 16B, which illustrated respectively the results of tumor size (FIG. 16A) and tumor metastasis (FIG. 16B) of orthotopically allografted breast cancer cells 4T1 of mice inhibited by PTX3 mAb of the control antibody according to an embodiment of the present invention. FIG. 16B was the in vivo imaging picture at the fifth week after inoculation of breast cancer cell 4T1, in which the radiance regions referred to the tumors formed from the breast cancer cells 4T1 in mice. All data of FIG. 16A were obtained from hexaplicates at each time point and each sample as mean plus or minus the averaged standard deviation. In this example, two asterisks (**) indicated the data having a statistically significant difference (p<0.01) compared to the control antibody (IgG1k).

The results of FIGS. 16A and 16B were shown that, compared to the data of the control antibody IgG1k, the PTX3 mAb of Example 1 could significantly inhibit the tumor size and tumor metastasis of the breast cancer cell line 4T1 orthotopical allograft, and the differences had statistical significances.

3. Evaluation of PTX3 Monoclonal Antibody of Example 1 and Anti-Cancer Drug Affecting Inhibition of In Vivo Growth and Metastasis of Orthotopically Allografted Breast Cancers (I)

In this EXAMPLE, the same method as the 2$^{nd}$ part of EXAMPLE 6 was used in the evaluation except that mouse cancer cell line 4T1 was orthotopically inoculated into the mammary fat pad of BALB/c female mice (six to eight weeks old, purchased from BioLASCO Taiwan Co., Ltd.) in this EXAMPLE. Once tumors reached an average volume of 50 mm$^3$, mice were i.p. injected with PTX3 antibody (2.5, 5.0 or 10 mg/kg body weight, JustWin Biotech Co., Ltd.) of EXAMPLE 1 or control antibody (IgG1K, 10 mg/kg body weight, Product No. 10101, Leadgene Biomedical, Inc., Taiwan), or in combination with Taxol (Paclitaxel, 30.0 mg/kg body weight), once a week for six weeks. All mice were sacrificed at the sixth week, the size and metastasis of tumors were observed by the in vivo bioluminescent imaging system.

Figure 17A:
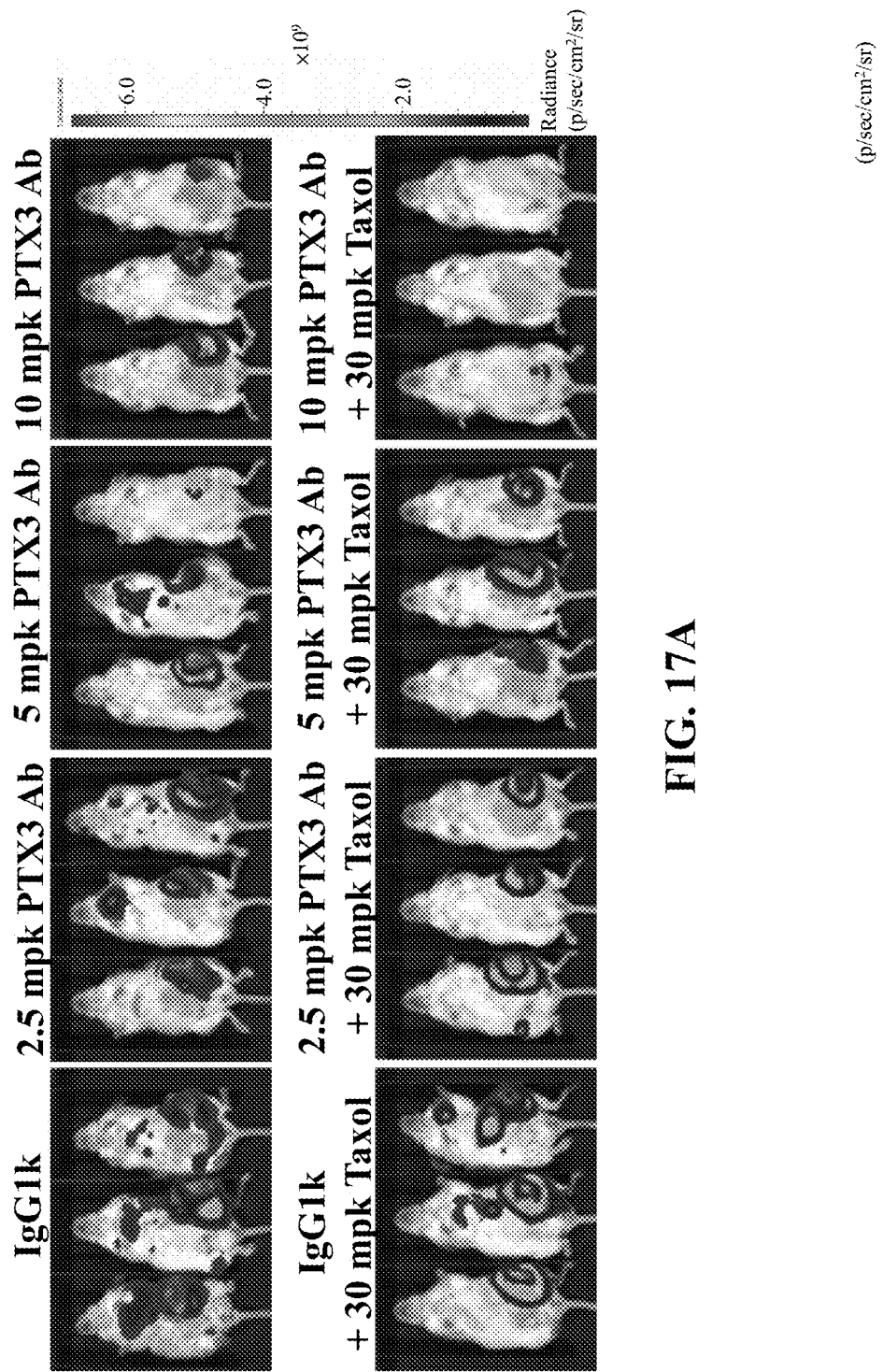
FIGS. 17A to 17C illustrate respectively in vivo imaging picture of tumor volume and metastasis (FIG. 17A) and line graphs (FIGS. 17B and 17C) of changes in tumor volume of orthotopically allografted breast cancer cells 4T1 of mice inhibited by PTX3 monoclonal antibody (FIG. 17B) or in combination with Taxol (FIG. 17C) according to an embodiment of the present invention.

After six weeks, the size of tumors was observed by the in vivo bioluminescent imaging system [for example, non-invasive 3D in vivo imaging system (IVIS system), PerkinElmer], the result was shown in FIG. 17A, and the radiance regions referred to the tumors formed from 4T1 cells in mice. The system could measure the tumor sizes and metastasis in mice, the tumor volume was calculated by the formula (I), and the result was shown in FIGS. 17B and 17C.

Figure 17B:
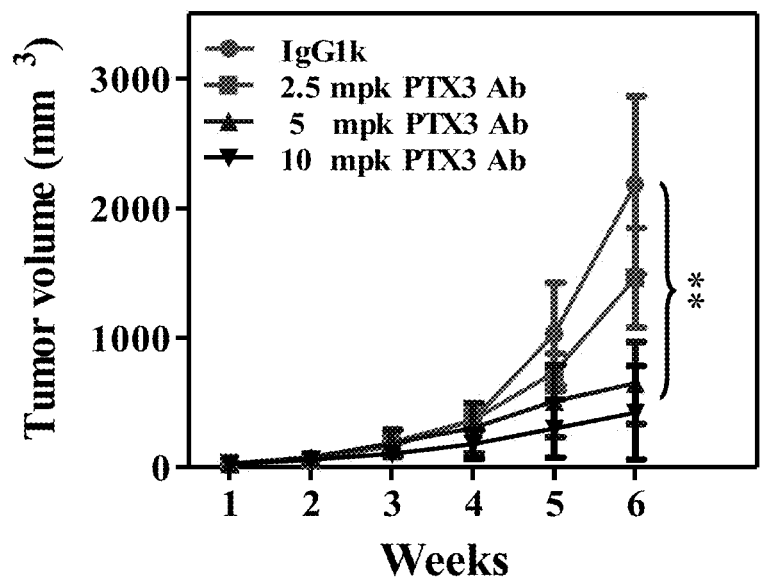
Figure 17C:
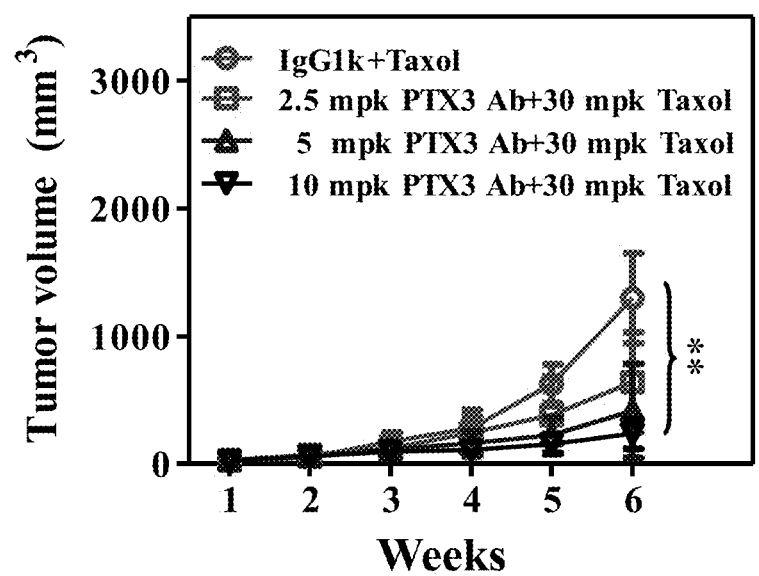

Reference was made to FIGS. 17A to 17C, which illustrated respectively in vivo imaging picture of tumor volume and metastasis (FIG. 17A) and line graphs (FIGS. 17B and 17C) of changes in tumor volume of orthotopically allografted breast cancer cells 4T1 of mice inhibited by PTX3 mAb (FIG. 17B) or in combination with Taxol (FIG. 17C) according to an embodiment of the present invention. All data of FIGS. 17B and 17C were obtained from hexaplicates at each time point and each sample as mean plus or minus the averaged standard deviation. In this example, two asterisks (**) indicated the data having a statistically significant difference ($p<0.01$) compared to the control antibody (IgG1k).

The results of FIGS. 17A to 17C were shown that, compared to the data of the control antibody IgG1k, the PTX3 mAb of Example 1 or Taxol could inhibit or alleviate the tumor volume and metastasis of the breast cancer cell line 4T1 orthotopical allograft, as shown in FIGS. 17A and 17B. However, combined administration of the PTX3 mAb of Example 1 and Taxol could significantly inhibit or alleviate the tumor volume and metastasis of the breast cancer cell line 4T1 orthotopical allograft, indicating that the synergic effect of the combined administration was much more than the individual administration, as shown in FIGS. 17A and 17C, and the differences had statistical significances.

4. Evaluation of PTX3 Monoclonal Antibody of Example 1 and Anti-Cancer Drug in Combination with Anti-Cancer Drug Affecting Inhibition of In Vivo Growth of Orthotopically Allografted Breast Cancers (II)

Figure 18A:
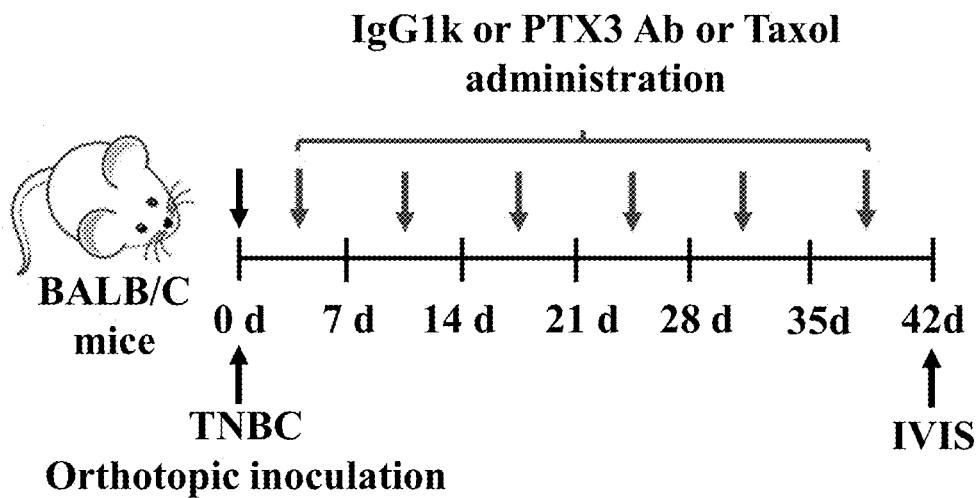
FIG. 18A illustrates an experimental scheme for evaluation of orthotopically allografted breast cancer cells 4T1 of mice treated with PTX3 monoclonal antibody or in combination with Taxol according to an embodiment of the present invention.
Figure 18B:
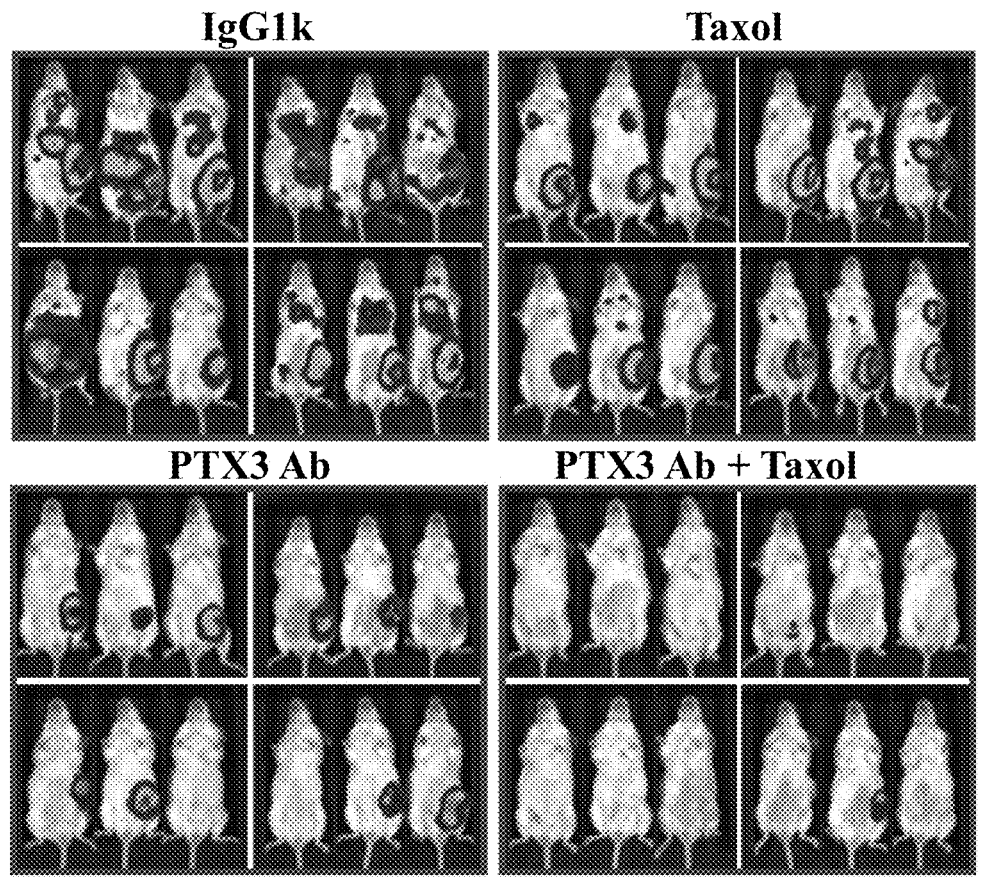
FIGS. 18B to 18D illustrate respectively in vivo imaging picture of tumor volume and metastasis (FIG. 18B), a line graph (FIG. 18C) of changes in tumor volume and survival rate of mice (FIG. 18D) of orthotopically allografted breast cancer cells 4T1 of mice inhibited by PTX3 mAb or in combination with Taxol according to another embodiment of the present invention.
Figure 18C:
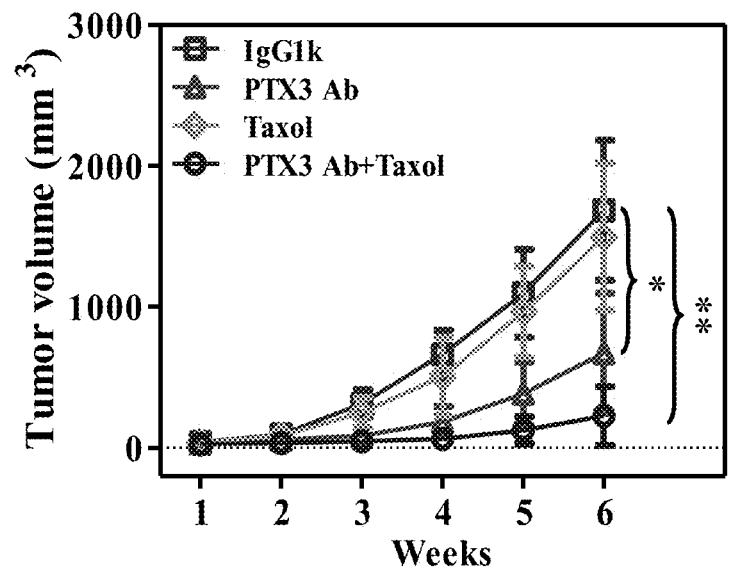
Figure 18D:
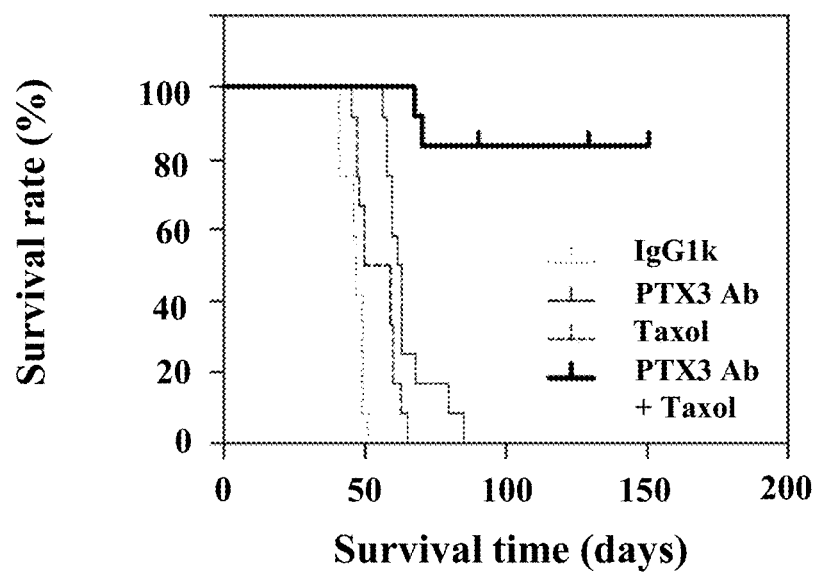

In this EXAMPLE, the experimental scheme of FIG. 18A and the same method as the $3^{nd}$ part of EXAMPLE 6 were used in the evaluation, and the results were shown in FIGS. 18B to 18D.

Reference was made to FIGS. 18B to 18D, which illustrated respectively in vivo imaging picture of tumor volume and metastasis (FIG. 18B), a line graph (FIG. 18C) of changes in tumor volume and survival rate of mice (FIG. 18D) of orthotopically allografted breast cancer cells 4T1 of mice inhibited by PTX3 mAb or in combination with Taxol according to another embodiment of the present invention. All data of FIGS. 18C to 18D were obtained from hexaplicates at each time point and each sample as mean plus or minus the averaged standard deviation. In this example, one asterisk (*) indicated the data having a statistically significant difference ($p<0.05$), and two asterisks (**) indicated the data having a statistically significant difference ($p<0.01$) compared to the control antibody (IgG1k).

The results of FIGS. 18B to 18D were shown that, compared to the data of the control antibody IgG1k, the PTX3 mAb of Example 1 or Taxol could inhibit or alleviate the tumor volume and metastasis of the breast cancer cell line 4T1 orthotopical allograft, as shown in FIGS. 18B and 18C. However, combined administration of the PTX3 mAb of Example 1 and Taxol could significantly inhibit or alleviate the tumor volume and metastasis of the breast cancer cell line 4T1 orthotopical allograft, and the mice could have an increased survival rate of 80% or more, indicating that the synergic effect of the combined administration was much more than the individual administration, as shown in FIG. 18D, and the differences had statistical significances.

Figure 19A:
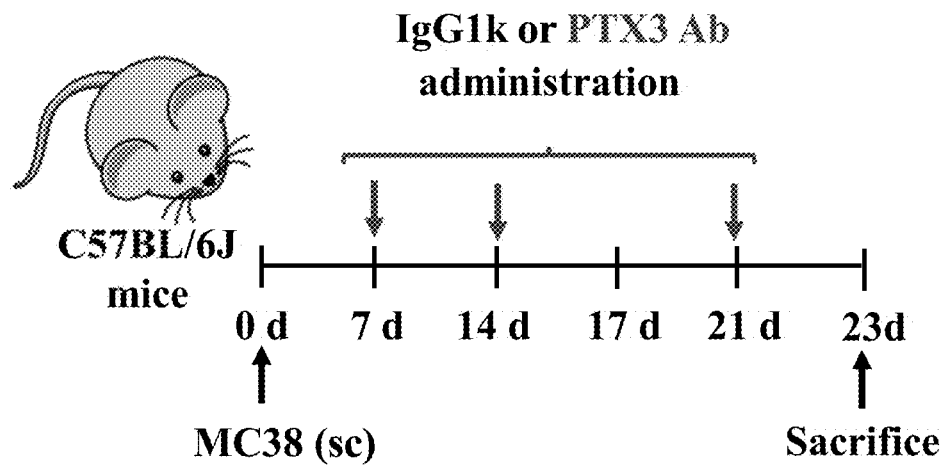
FIG. 19A illustrates an experimental scheme for evaluation of allografted colon adenocarcinoma cell line MC38 of mice inhibited by PTX3 monoclonal antibody or the control antibody according to an embodiment of the present invention.

5. Evaluation of PTX3 Monoclonal Antibody of Example 1 and Anti-Cancer Drug Affecting Inhibition of In Vivo Growth of Orthotopically Allografted Colorectal Cancers In this EXAMPLE, the experimental scheme of FIG. 19A and the same method as the $3^{nd}$ part of EXAMPLE 6 was used in the evaluation except that mouse colon adenocarcinoma cell line MC38 was subcutaneously (s.c.) injected into C57BL/6J male mice (six to eight weeks old, purchased from BioLASCO Taiwan Co., Ltd.) in this EXAMPLE. Seven days after the injection of the MC38 cells, mice were i.p. injected with PTX3 antibody (10 mg/kg body weight, JustWin Biotech Co., Ltd.) of EXAMPLE 1 or control antibody (IgG1K, 10 mg/kg body weight, Product No. 10101, Leadgene Biomedical, Inc., Taiwan), once a week in triplicates. The tumor size of all mice was observed weekly by the in vivo bioluminescent imaging system. All mice were sacrificed on the 23th day, the tumor size was measured, and the tumor volume was calculated by the formula (I).

Figure 19B:
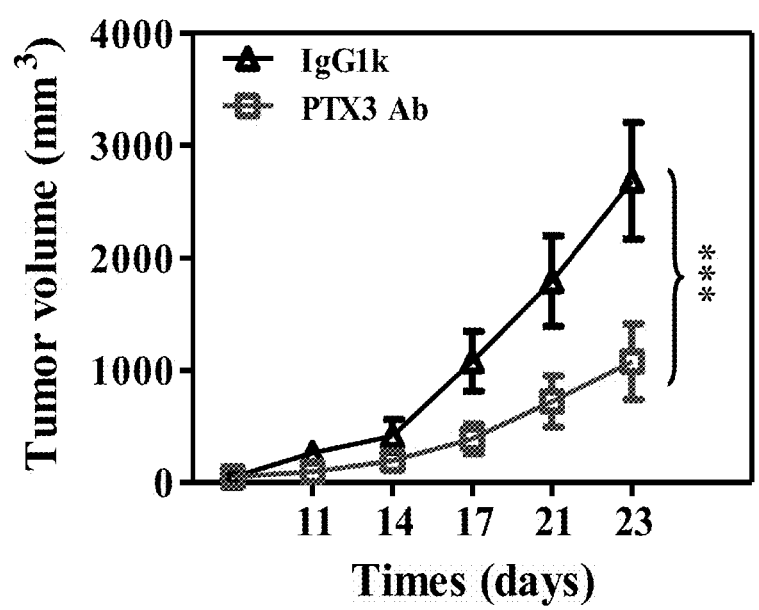
FIG. 19B illustrates a line graph of tumor volume in the mice allografted colon adenocarcinoma cell line MC38 inhibited by PTX3 monoclonal antibody or the control antibody according to an embodiment of the present invention.

Reference was made to FIG. 19B, which illustrated a line graph of tumor volume in the mice allografted colon adenocarcinoma cell line MC38 inhibited by PTX3 mAb or the control antibody according to an embodiment of the present invention. All data of FIG. 19B were obtained from quadruplicates at each time point and each sample as mean plus or minus the averaged standard deviation. In this example, one asterisk (*) indicated the data having a statistically significant difference ($p<0.05$), and three asterisks (***) indicated a statistically significant difference compared to the control group ($p<0.001$).

The result of FIG. 19B was shown that, compared to the data of the control antibody IgG1k, the PTX3 mAb of Example 1 could inhibit or alleviate the tumor volume of the colon adenocarcinoma cell line MC38 orthotopical allograft, and the differences had statistical significances.

6. Evaluation of PTX3 Monoclonal Antibody of EXAMPLE 1 and Anti-Cancer Drug Affecting Inhibition of In Vivo Growth of Xenografted Glioblastoma Multiforme In this EXAMPLE, the same method as the $3^{nd}$ part of EXAMPLE 6 was used in the evaluation except that human glioblastoma multiforme (GBM) cell line U87MG was subcutaneously (s.c.) injected into NOD-SCID male mice (six to eight weeks old, purchased from BioLASCO Taiwan Co., Ltd.) in this EXAMPLE. Twenty days after the injection of the U87MG cells, mice were i.p. injected with PTX3 antibody (10 mg/kg body weight, JustWin Biotech Co., Ltd.) of EXAMPLE 1 or control antibody (IgG1K, 10 mg/kg body weight, Product No. 10101, is Leadgene Biomedical, Inc., Taiwan), once a week for four weeks. After twenty days, the tumor size was measured, and the tumor volume was calculated by the formula (I).

Figure 20A:
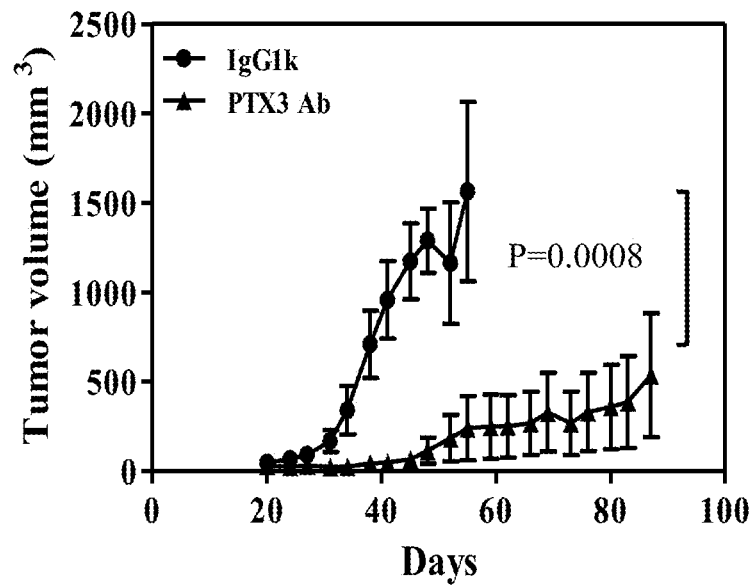
FIGS. 20A and 20B illustrate line graphs of tumor volume (FIG. 20A) and the survival rate (FIG. 20B) of mice xenografted human GBM cell line U87MG inhibited by PTX3 monoclonal antibody or the control antibody according to an embodiment of the present invention.
Figure 20B:
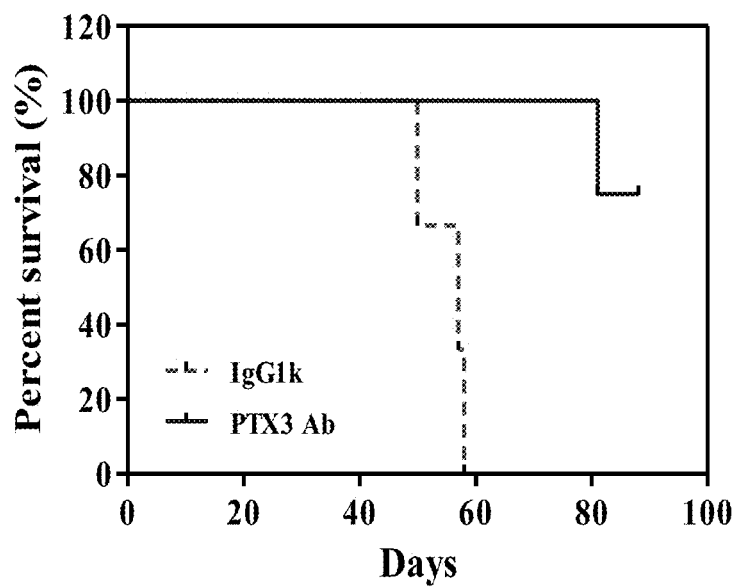

Reference was made to FIGS. 20A and 20B, which illustrated line graphs of tumor volume (FIG. 20A) and the survival rate (FIG. 20B) of mice xenografted human GBM cell line U87MG inhibited by PTX3 mAb or the control antibody according to an embodiment of the present invention. All data of FIG. 20A were obtained from triplicates or quadruplicates at each time point and each sample as mean plus or minus the averaged standard deviation. In this example, "p=0.0008" indicated the data having a statistically significant difference compared to the control group.

The result of FIGS. 20A and 20B was shown that, compared to the data of the control antibody IgG1k, the PTX3 mAb of Example 1 could inhibit or alleviate the tumor volume of the human GBM cell line U87MG xenograft (FIG. 20A) and the survival rate of mice was increased up to 75% (FIG. 20B). Those differences had statistical significances.

Figure 21A:
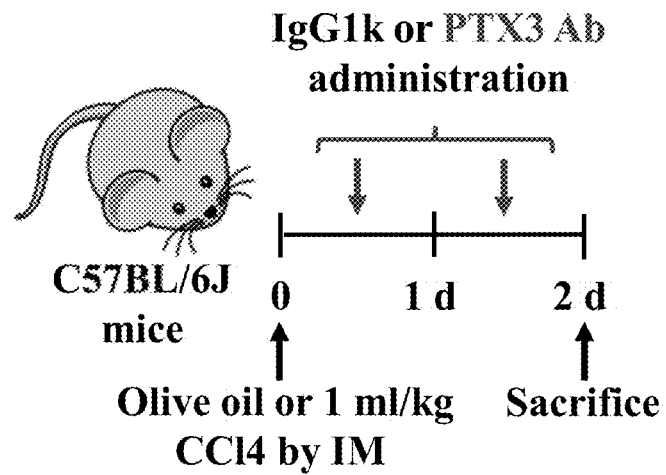
FIG. 21A illustrates an experimental scheme for evaluation of acute liver fibrosis of the mice improved by PTX3 monoclonal antibody according to an embodiment of the present invention.

Example 7. Evaluation of PTX3 Monoclonal Antibody od Example 1 Affecting Alleviation or Reversion of Fibrosis In Vivo 1. Evaluation of PTX3 Monoclonal Antibody of Example 1 Affecting Reversion of Liver Necrosis of Acute Hepatic Fibrosis In this EXAMPLE, the experimental scheme of FIG. 21A was used in the evaluation, which was designed according to the Guideline of Laboratory Animal Center of E-Da Hospital, I-Shou University, Taiwan. Firstly, 1 mL/kg body weight of carbon tetrachloride ($CCl_4$ mixed with olive oil in a volume ratio of 1:1) was intramuscularly injected to C57BL/6J male mice (eight weeks old, purchased from BioLASCO Taiwan Co., Ltd., Taiwan). Carbon tetrachloride induced acute hepatic fibrosis and resulted in apoptosis and necrosis of hepatocytes within twelve hours. Next, mice were i.p. injected with PTX3 antibody (10 mg/kg body weight, JustWin Biotech Co., Ltd.) of EXAMPLE 1 or control antibody (IgG1K, 10 mg/kg body weight, Product No. 10101, Leadgene Biomedical, Inc., Taiwan) at the fourth and twenty-eighth hours after injection of carbon tetrachloride. All mice were sacrificed at the second day after the administration of antibodies, the liver histological sections, the percentage of necrosis area per section and the ratio of liver weight to body weight were observed, as shown in FIGS. 21B to 21D.

Figure 21B:
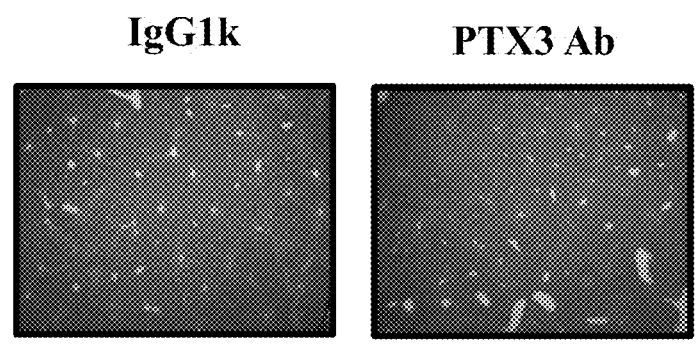
FIGS. 21B to 21D illustrate respectively the images of hematoxylin-eosin (H&E)-stained histological sections of left liver lobe (FIG. 21B, with 20× magnification, for observation of hepatocyte apoptosis), the bar diagrams of the percentage of necrosis area per section (FIG. 21C) and the ratio of liver weight to body weight (FIG. 21D) in acute liver fibrosis of the mice with the PTX3 monoclonal antibody of Example 1 according to an embodiment of the present invention.
Figure 21C:
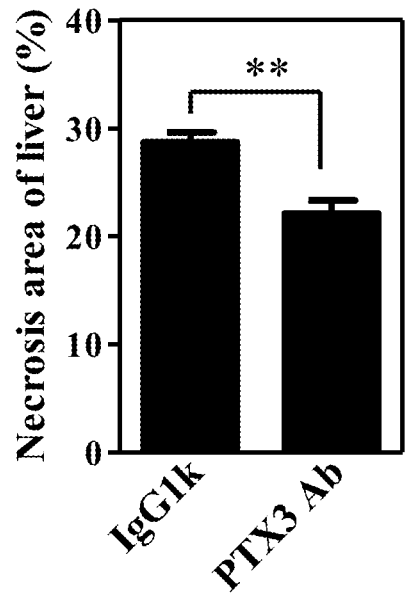
Figure 21D:
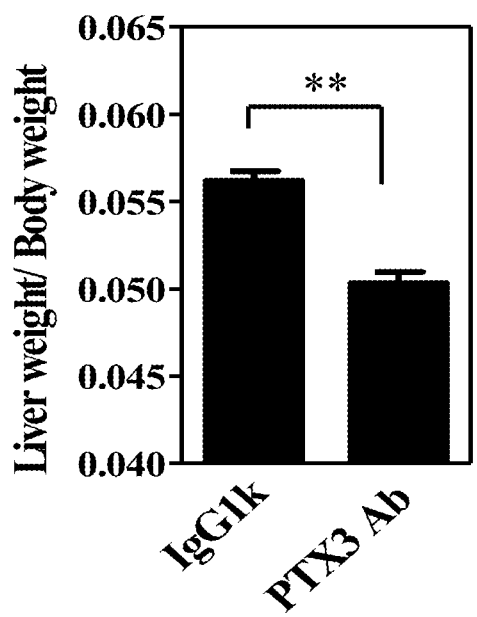

Reference was made to FIGS. 21B to 21D, which illustrated respectively the images of hematoxylin-eosin (H&E)-stained histological sections of left liver lobe (FIG. 21B, with 20× magnification, for observation of hepatocyte apoptosis), the bar diagrams of the percentage of necrosis area per section (FIG. 21C) and the ratio of liver weight to body weight (FIG. 21D) in acute liver fibrosis of the mice with the PTX3 mAb of Example 1 according to an embodiment of the present invention. In FIG. 21C, the percentage of necrosis area in the total scanning area was measured by the automatic thresholding function of the commercially available image analysis soft ImageJ (W.S. Rasband, NIH, Bethesda, Maryland, USA).

The result of FIGS. 21B to 21D was shown that, compared to the data of the control antibody IgG1k, the PTX3 mAb of Example 1 could alleviate apoptosis (FIG. 21B) and necrosis (FIG. 21C) of carbon tetrachloride-induced acute hepatic fibrosis, as well as alleviate the level of increased liver weight (FIG. 21D) of mice caused by acute hepatic fibrosis. Those differences had statistical significances.

Figure 22A:
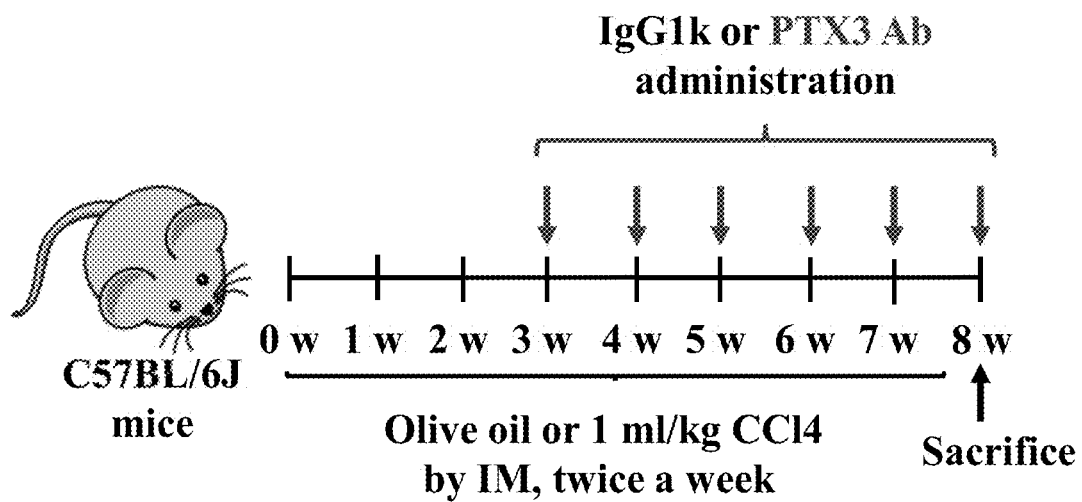
FIG. 22A illustrates the experimental scheme for evaluating the improvement of chronic liver fibrosis of the mice treated with the PTX3 monoclonal antibody of Example 1 according to an embodiment of the present invention.

2. Evaluation of PTX3 Monoclonal Antibody of Example 1 Affecting Reversion of Liver Necrosis of Chronic Hepatic Fibrosis In this EXAMPLE, the experimental scheme of FIG. 22A was used in the evaluation, the same method as the $1^{st}$ part of EXAMPLE 7 was designed in the evaluation except that 1 mL/kg body weight of carbon tetrachloride ($CCl_4$ mixed with olive oil in a volume ratio of 1:1) was intramuscularly injected to C57BL/6J male mice (eight weeks old, purchased from BioLASCO Taiwan Co., Ltd., Taiwan), twice a week for eight weeks. Next, mice were i.p. injected with PTX3 antibody (10 mg/kg body weight, JustWin Biotech Co., Ltd.) of EXAMPLE 1 or control antibody (IgG1K, 10 mg/kg body weight, Product No. 10101, Leadgene Biomedical, Inc., Taiwan) at the third and eighth hours after injection of carbon tetrachloride, once a week. All mice were sacrificed at the end of the eighth week after the administration of antibodies, the liver histological sections, the percentage of necrosis area per section and the ratio of liver weight to body weight were observed, as shown in FIGS. 22B to 22D.

Figure 22B:
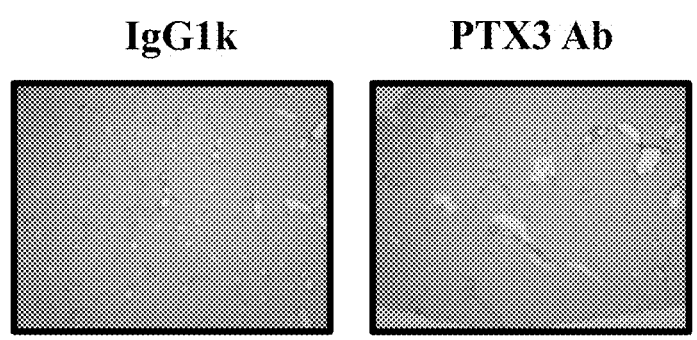
FIGS. 22B to 22D illustrate respectively the images of Picro-Sirius Red-stained histological sections of left liver lobe (FIG. 22B), the bar diagrams of the percentage of liver fibrosis area per section (FIG. 22C) and the ratio of liver weight to body weight (FIG. 22D) in chronic liver fibrosis of the mice treated with the PTX3 monoclonal antibody of Example 1 according to an embodiment of the present invention.
Figure 22C:
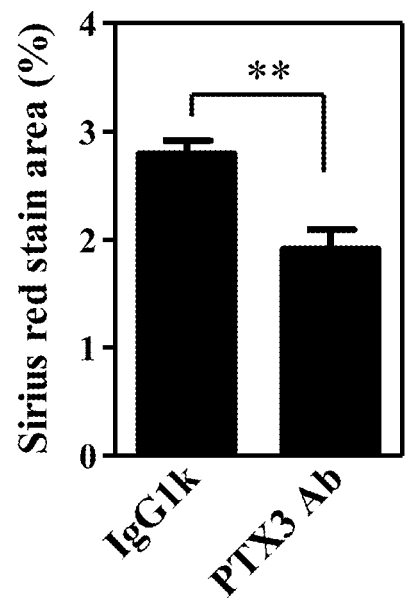
Figure 22D:
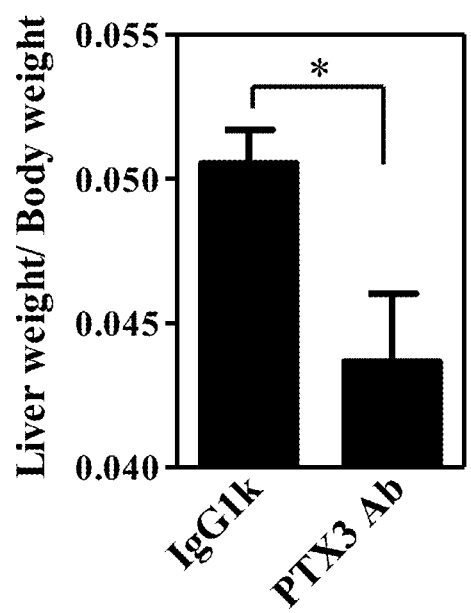

Reference was made to FIGS. 22B to 22D, which illustrated respectively the images of Picro-Sirius Red-stained histological sections of left liver lobe (FIG. 22B, with 20× magnification, for observation of hepatocyte fibrosis), the bar diagrams of the percentage of liver fibrosis area per section (FIG. 22C) and the ratio of liver weight to body weight (FIG. 22D) in chronic liver fibrosis of the mice treated with the PTX3 mAb of Example 1 according to an embodiment of the present invention. In FIG. 22C, the percentage of liver necrotic area in the total scanning area was measured by the automatic thresholding function of the commercially available image analysis soft ImageJ (W.S. Rasband, NIH, Bethesda, Maryland, USA).

The result of FIGS. 22B to 22D was shown that, compared to the data of the control antibody IgG1k, the PTX3 mAb of Example 1 could alleviate chronic liver fibrosis (FIG. 22B) and the percentage of fibrosis area (FIG. 22C) of carbon tetrachloride-induced chronic hepatic fibrosis, as well as alleviate the level of increased liver weight (FIG. 22D) of mice caused by chronic hepatic fibrosis. Those differences had statistical significances.

4. Evaluation of PTX3 Monoclonal Antibody of Example 1 Affecting Fibrosis-Related Protein Expression of Kidney Fibroblasts In this EXAMPLE, rat kidney fibroblast cell line NRK49F (Deposit Accession Number: BCRC 60084 or ATCC® CRL-1570™) was used in following experiments for evaluation of PTX3 monoclonal antibody of EXAMPLE 1 affecting kidney fibrosis.

Firstly, kidney fibroblast cell line NRK49F was cultured in Dulbecco's Modified Eagle Medium (DMEM) (12800-082, Gibco) (supplemented with 10% FBS, 100 μg/mL of streptomycin and 100 U/mL of penicillin).

NRK49F cells were treated with 0.4 μg/mL of the control antibody (IgG1k, Product No. 10101, Leadgene Biomedical, Inc., Taiwan) or 0.4 μg/mL of PTX3 mAb (JustWin Biotech Co., Ltd.), followed by treatment of 200 ng/mL of PTX3 recombinant protein for 6 hours. And then, NRK49F cells were lysed in modified radioimmunoprecipitation assay (RIPA) buffer, which included 50 mM Tris-HCl (pH 7.4), 150 mM NaCl, 1 mM EDTA, 1% NP-40, 0.25% of sodium deoxycholate, 1 mM of dithiothreitol (DTT), 1 mM of phenylmethylsulfonyl fluoride (PMSF), aprotinin (1 mg/ml) and leupeptin (1 mg/ml). Next, Western blotting was used for detecting the expressions of α-tubulin (Product Number: T6199, Sigma) and fibronectin (Product Number: 15613-1-AP, ProteinTech) with specific antibodies, the expression of the α-tubulin served as a loading control group, and the result was shown in FIG. 23A.

In addition, NRK49F cells were seeded into 24-well cell culture plate and treated with 0.4 μg/mL of the control antibody IgG1k (Product No. 10101, Leadgene Biomedical, Inc., Taiwan), 0.4 μg/mL of PTX3 mAb (JustWin Biotech Co., Ltd.) or 200 ng/mL of PTX3 recombinant protein for 24 hours. Next, NRK49F cells were fixed in methanol at −20° C. overnight. On the next day, NRK49F cells were stained by Picro-Sirius Red Solution (Product Number: ab246832, Abcam) under room temperature for 20 minutes, and rinsed twice by acetic acid. Nodule numbers of cells were counted according to images under optical microscope with 200× magnification. Later, the cells were lysed in 0.1N NaOH, and the absorbance of each well at 490 nm was detected by commercially available ELISA reader, and the results were shown in FIGS. 23B and 23C.

Figure 23A:
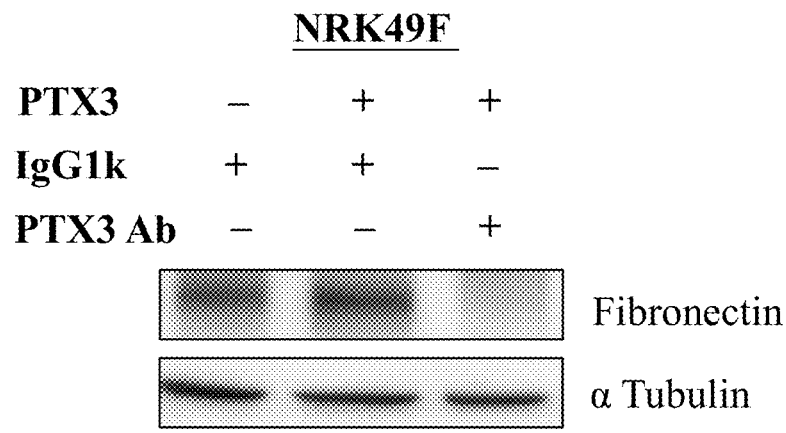
FIGS. 23A to 23C illustrated respectively western blotting images of fibrosis-related protein expression (FIG. 23A), images (FIG. 23B) and a bar diagram (FIG. 23C) of stained cells in nodules of kidney fibroblasts treated with PTX3 monoclonal antibody according to an embodiment of the present invention.
Figure 23B:
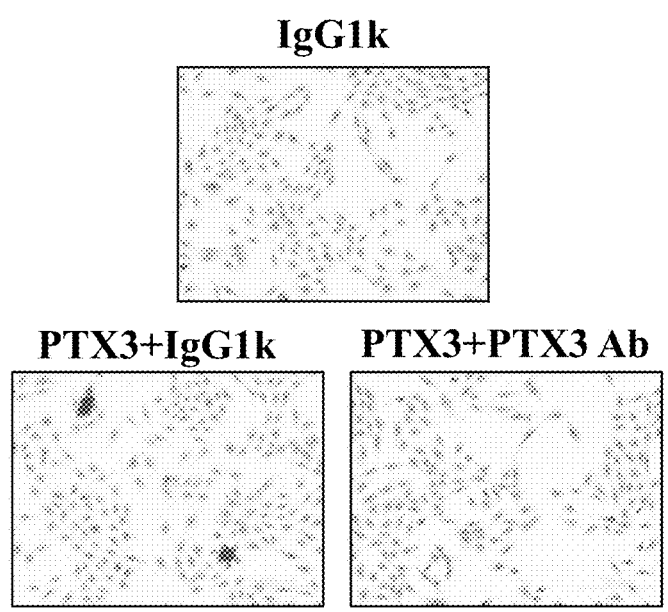
Figure 23C:
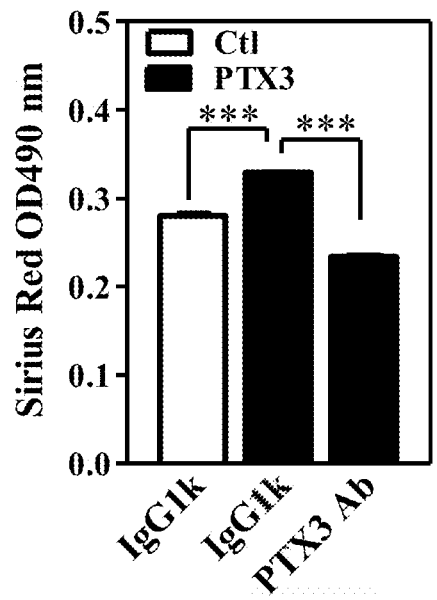

Reference was made to FIGS. 23A to 23C, which illustrated respectively western blotting images of fibrosis-related protein expression (FIG. 23A), images (FIG. 23B) and a bar diagram (FIG. 23C) of stained cells in nodules of kidney fibroblasts treated with PTX3 mAb according to an embodiment of the present invention, and three asterisks (***) indicated the data having a statistically significant difference ($p<0.001$) compared to the control antibody (IgG1k).

The results of FIGS. 23A to 23C were shown that, compared to the data of the control antibody (IgG1k), the PTX3 mAb of Example 1 could reduce the expressions of fibrosis-related proteins of kidney fibroblasts (FIG. 23A) and the nodule numbers of cells (FIGS. 23B and 23C), as well as the differences had statistical significances.

Figure 24A:
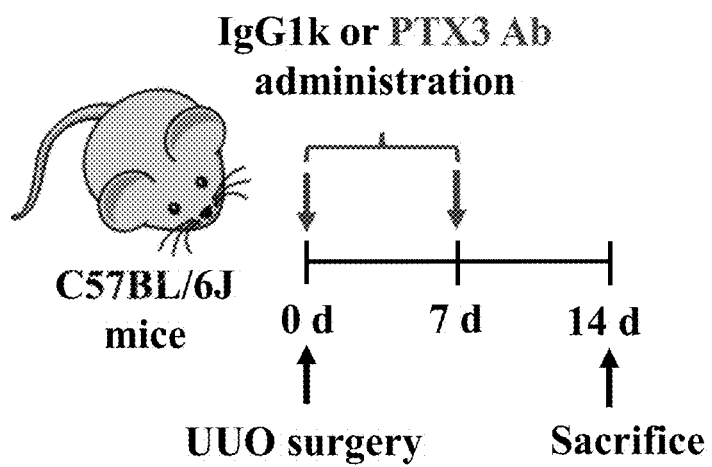
FIGS. 24A to 24D illustrated respectively experimental schemes (FIGS. 24A and 24C) and histological staining images (FIGS. 24B and 24D) of kidney of UUO mice detected by PTX3 monoclonal antibody of EXAMPLE 1 according to an embodiment of the present invention.
Figure 24B:
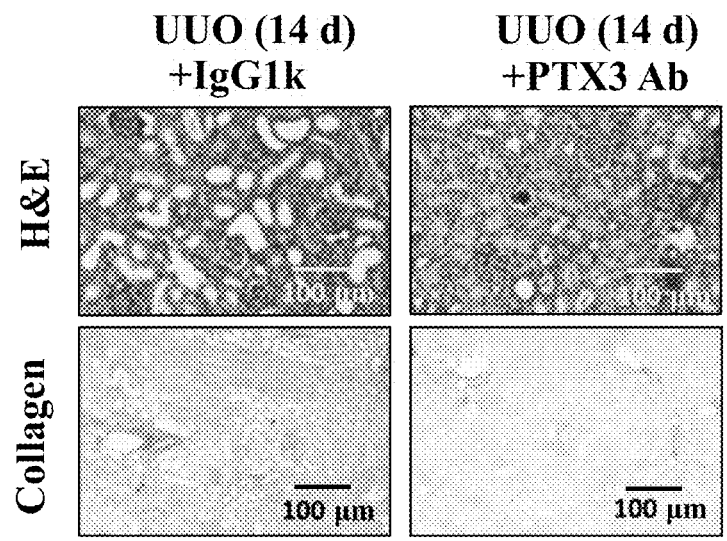
Figure 24C:
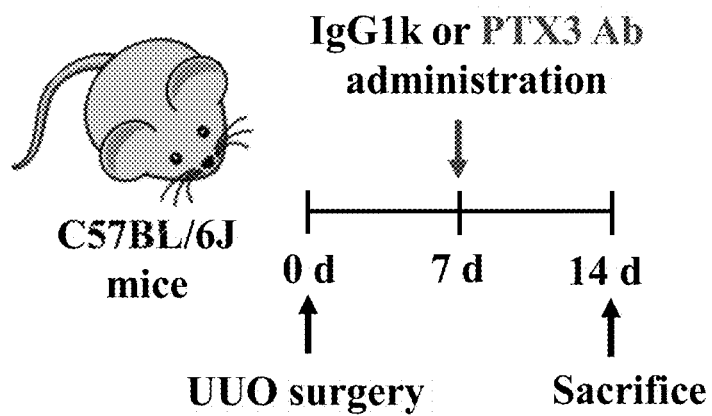
Figure 24D:
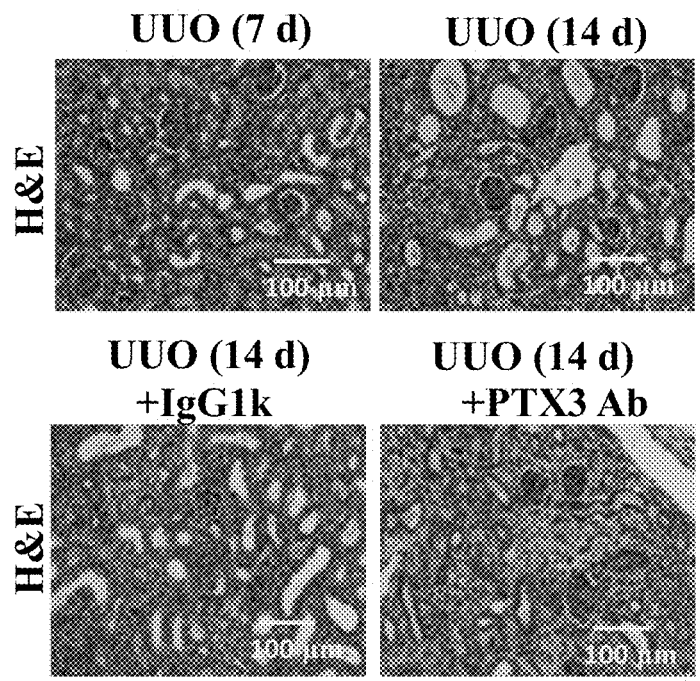

5. Evaluation of PTX3 Monoclonal Antibody of Example 1 Affecting Alleviation of Kidney Fibrosis in Unilateral Ureteral Obstruction (UUO) Animal Model In this EXAMPLE, the experimental schemes of FIGS. 24A and 24C were used in the evaluation. Firstly, C57BL/6J male mice (six to eight weeks old, purchased from Bio-LASCO Taiwan Co., Ltd., Taiwan) were provided. Next, mice were subjected to unilateral ureteral obstruction (UUO) via left flank incision. The left kidney was removed and the left exposed ureter was ligated with silk suture (4-O Silk). Later, the incision was closed by a surgical stapler. Afterward, at the zero and seventh days after UUO surgery (pre-treatment as shown in FIGS. 24A and 24B) or at the seventh day after UUO surgery (post-treatment as shown in FIGS. 24C and 24D), the mice were treated with the control antibody (IgG1K, 10 mg/kg body weight, Product No. 10101, Leadgene Biomedical, Inc., Taiwan) or PTX3 antibody (10 mg/kg body weight, JustWin Biotech Co., Ltd.) of EXAMPLE 1. All mice were euthanized at the 14$^{th}$ day after UUO surgery. The half of the kidney was fixed in formalin and embedded in paraffin. The histological sections were stained by hematoxylin-eosin (H&E) or Picro-Sirius Red Solution (Product Number: ab246832, Abcam), covered with cover slips and sealed. The histological sections were observed with 20× magnification, and all images were shown in FIGS. 24B and 24C with a scale bar in 100 μm.

Reference was made to FIGS. 24B and 24D, which illustrated respectively histological staining images of kidney of UUO mice detected by PTX3 mAb of EXAMPLE 1 according to an embodiment of the present invention.

The results of FIGS. 24B and 24D were shown that, compared to the data of the control antibody (IgG1k), the PTX3 mAb of Example 1 could indeed reduce the kidney fibrosis of UUO animals.

6. Evaluation of PTX3 Monoclonal Antibody of Example 1 Affecting Fibrosis-Related Protein Expression and Migration of Lung Fibroblasts Treated by PTX3

In this EXAMPLE, human lung fibroblast cell line HFL1 (Deposit Accession Number: BCRC 60299 or ATCC® CRL-153™) was used in following experiments for evaluation of PTX3 monoclonal antibody of EXAMPLE 1 affecting pulmonary fibrosis.

Firstly, HFL1 cells were cultured in Han's F12K Medium (F12K) (Kaighn's modification)(21127-022, Gibco) (supplemented with 10% FBS, 100 μg/mL of streptomycin and 100 U/mL of penicillin).

Figure 25A:
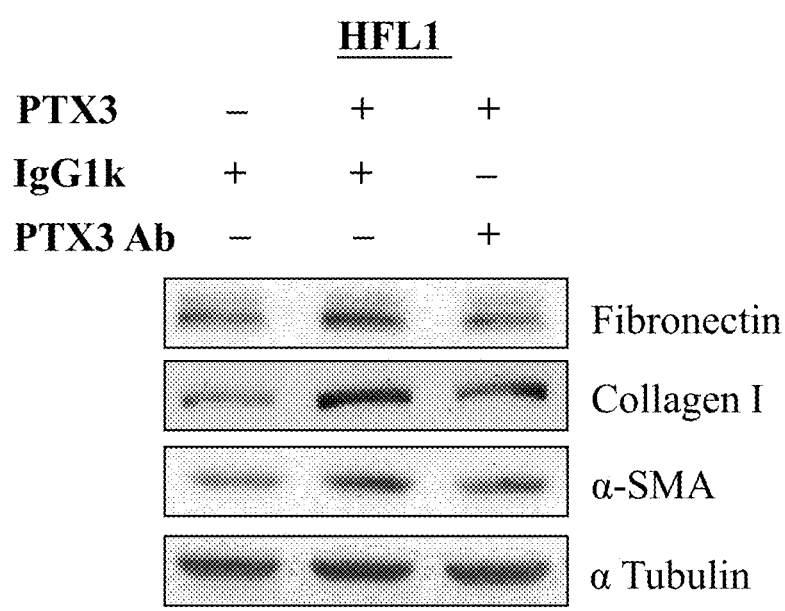
FIGS. 25A to 25D illustrate respectively western blotting images (FIG. 25A), a bar diagram of migration cell numbers (FIG. 25B), images (FIG. 25C) and a bar diagram (FIG. 25D) of stained cells in nodules of lung fibroblasts treated with PTX3 monoclonal antibody according to an embodiment of the present invention.

HFL1 cells were treated with 0.4 μg/mL of the control antibody (IgG1k, Product No. 10101, Leadgene Biomedical, Inc., Taiwan) or 0.4 μg/mL of PTX3 mAb (JustWin Biotech Co., Ltd.), followed by treatment of 200 ng/mL of PTX3 recombinant protein for 6 hours. And then, HFL1 cells were lysed in modified RIPA buffer. Next, Western blotting was used for detecting the expressions of α-tubulin (Product Number: T6199, Sigma), fibronectin (Product Number: 15613-1-AP, ProteinTech), Collagen type I (Product Number: 14695-1-AP, ProteinTech) and α-smooth muscle actin (α-SMA, Product Number: GTX 100904, GeneTex) with specific antibodies, the expression of the α-tubulin served as a loading control group, and the result was shown in FIG. 25A.

Figure 25B:
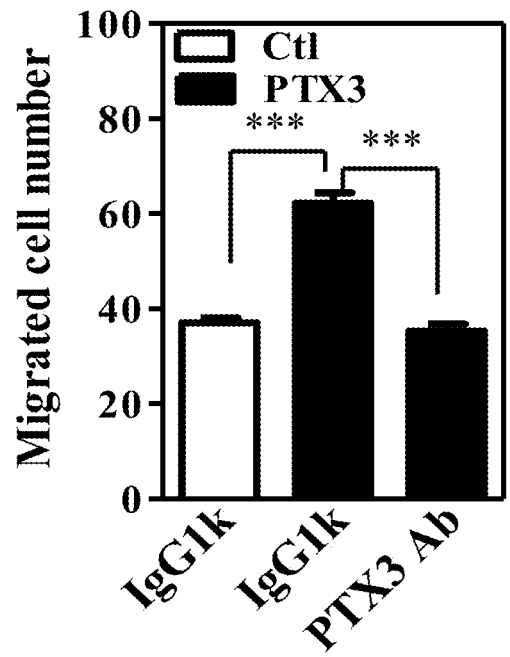

In addition, HFL1 cells were seeded into 24-well cell culture plate (each well having a insert with 8 μm pores in the bottom; Product Number: 353097, BD Biosciences), and the medium in each lower well was added without or with 0.4 μg/mL of the control antibody IgG1k (Product No. 10101, Leadgene Biomedical, Inc., Taiwan), 0.4 μg/mL of PTX3 mAb (JustWin Biotech Co., Ltd.) or 200 ng/mL of PTX3 recombinant protein. After treatment for 16 hours, the cells inside each upper insert were wiped with cotton swabs and removed after 16 hours of cultivation. Remaining cells that adhered on the lower surface of the polycarbonate membrane of the insert migrating out of the bottom of the insert were stained by DAPI and calculated in cell numbers under fluorescence microscopy with 200-fold magnification. The results were shown in FIG. 25B.

Figure 25C:
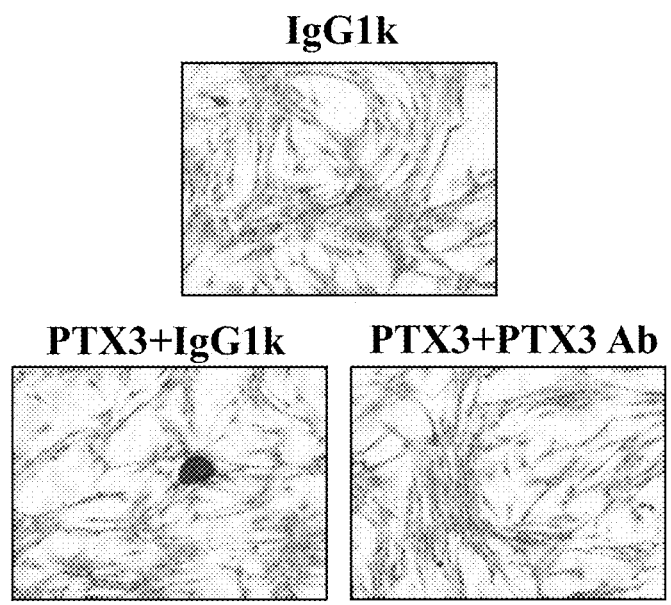
Figure 25D:
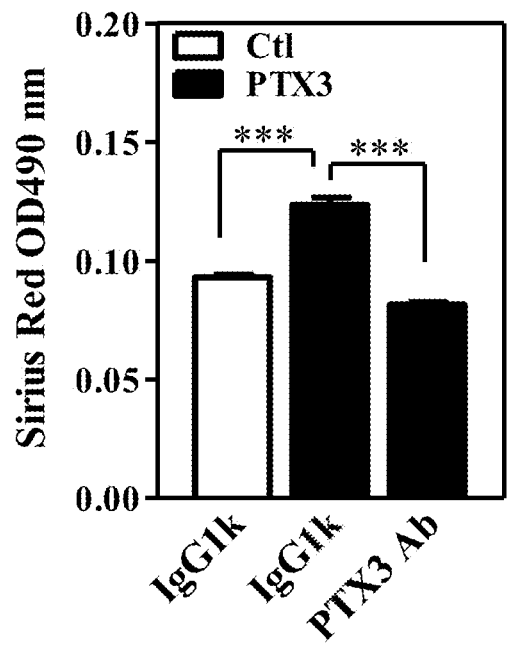

HFL1 cells were seeded into 24-well cell culture plate and treated without or with 0.4 μg/mL of the control antibody IgG1k (Product No. 10101, Leadgene Biomedical, Inc., Taiwan), 0.4 μg/mL of PTX3 mAb (JustWin Biotech Co., Ltd.) or 200 ng/mL of PTX3 recombinant protein for 24 hours. Next, HFL1 cells were fixed in methanol at −20° C. overnight. On the next day, HFL1 cells were stained by Picro-Sirius Red Solution (Product Number: ab246832, Abcam) under room temperature for 20 minutes, and rinsed twice by acetic acid. Nodule numbers of cells were counted according to images under optical microscope with 200× magnification. Later, the cells were lysed in 0.1N NaOH, and the absorbance of each well at 490 nm was detected by commercially available ELISA reader, and the results were shown in FIGS. 25C and 25D.

Reference was made to FIGS. 25A to 25D, which illustrated respectively western blotting images (FIG. 25A), a bar diagram of migration cell numbers (FIG. 25B), images (FIG. 25C) and a bar diagram (FIG. 25D) of stained cells in nodules of lung fibroblasts treated with PTX3 mAb according to an embodiment of the present invention. Three asterisks (***) indicated the data having a statistically significant difference ($p<0.001$) compared to the control antibody (IgG1k).

The results of FIGS. 25A to 25D were shown that, compared to the data of the control antibody (IgG1k), the PTX3 mAb of Example 1 could reduce the expressions of fibrosis-related proteins of lung fibroblasts, as well as the cell numbers of migration and the nodule numbers of cells.

7. Evaluation of PTX3 Monoclonal Antibody of Example 1 Affecting Pulmonary Fibrosis Induced by Bleomycin in IPF Mouse Model (I)

Figure 26A:
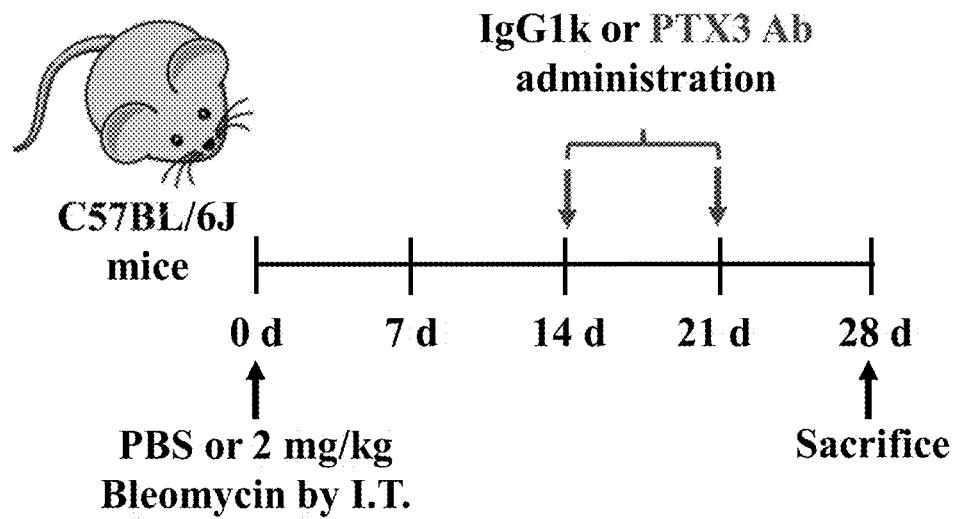
FIGS. 26A to 26D illustrate respectively an experimental scheme (FIG. 26A), a curve diagram of changes in body weight (FIG. 26B), gross examination of lung and histological staining images (FIGS. 26C and 26D) of BLM-induced pulmonary fibrosis of mice treated with PTX3 monoclonal antibody of EXAMPLE 1 according to an embodiment of the present invention.

In this EXAMPLE, the experimental schemes of FIG. 26A was used in the evaluation. Firstly, C57BL/6J male mice (six to eight weeks old, purchased from BioLASCO Taiwan Co., Ltd., Taiwan) were provided. Next, mice were intratracheally instilled (I.T.) with PBS or 2 mg/kg of bleomycin (BLM, Product Number: ap302, Enzo) to induce fibrosis. The $14^{th}$ and $21^{st}$ days after fibrosis induction, the mice were i.p. injected with the control antibody (IgG1K, 10 mg/kg body weight, Product No. 10101, Leadgene Biomedical, Inc., Taiwan) or PTX3 antibody (10 mg/kg body weight, JustWin Biotech Co., Ltd.). All mice were euthanized at the $28^{th}$ day after fibrosis induction.

The body weights of C57BL/6J mice were individually measured on the seventh, $14^{th}$, $21^{st}$ or $28^{th}$ days after intratracheal instillation with BLM, and then these mice were i.p. injected with 10 mg/kg body weight of the control antibody IgG1K (the control group) or PTX3 antibody. All results were shown in FIG. 26B.

After euthanization, the lung tissue of mice were grossly examined on the seventh, $14^{th}$, $21^{st}$ or $28^{th}$ days after intratracheal instillation with PBS (i.e. the healthy control group) or 2 mg/kg of BLM. The left lung lobes were intratracheally instilled, fixed in paraformaldehyde, and embedded in paraffin. The histological sections were stained by H&E, covered with cover slips and sealed. The histological sections were observed with 20× magnification, and all images were shown in FIG. 26C with a scale bar in 100 µm.

After euthanization, the BLM-induced pulmonary fibrosis tissues of mice were grossly examined on the $28^{th}$ day treated with 10 mg/mL of the control antibody (IgG1k) or PTX3 mAb. The left lung lobes were intratracheally instilled, fixed in paraformaldehyde, and embedded in paraffin. The histological sections were stained by H&E, covered with cover slips and sealed. The histological sections were observed with 20× magnification, and all images were shown in FIG. 26D with a scale bar in 100 µm.

Figure 26B:
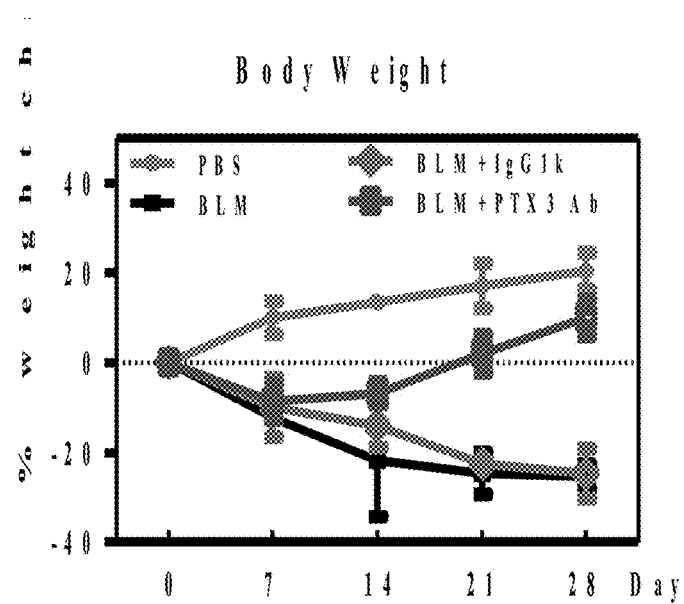
Figure 26C:
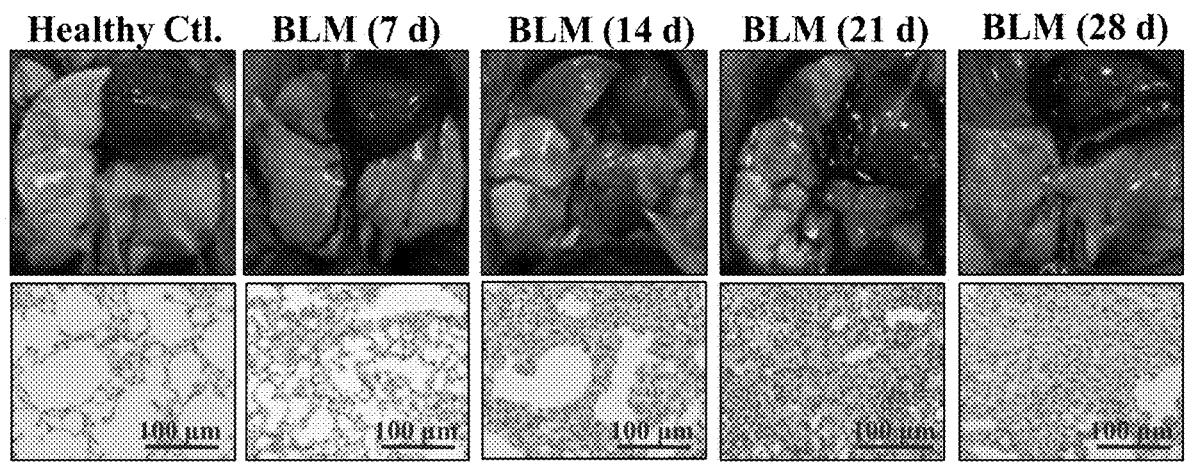
Figure 26D:
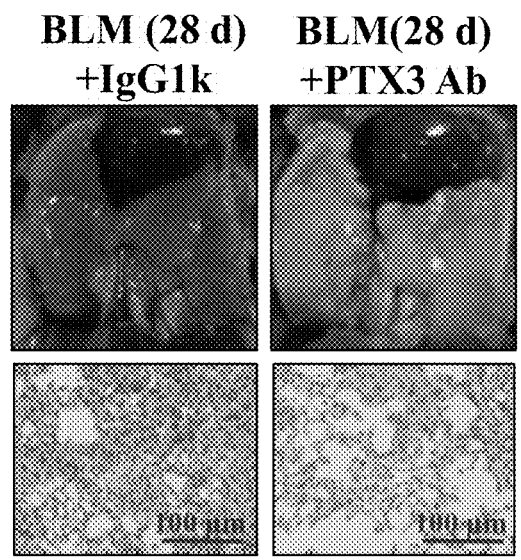

Reference was made to FIGS. 26B to 26D, which illustrated respectively a curve diagram of changes in body weight (FIG. 26B), gross examination of lung and histological staining images (FIGS. 26C and 26D) of BLM-induced pulmonary fibrosis of mice treated with PTX3 mAb of EXAMPLE 1 according to an embodiment of the present invention.

The results of FIGS. 26B to 26D were shown that, compared to the data of the control antibody (IgG1k), the PTX3 mAb of Example 1 could reverse the levels in pulmonary fibrosis and body weight loss caused by pulmonary fibrosis.

8. Evaluation of PTX3 Monoclonal Antibody of Example 1 Affecting Pulmonary Fibrosis Induced by Bleomycin in IPF Mouse Model (II)

Figure 27A:
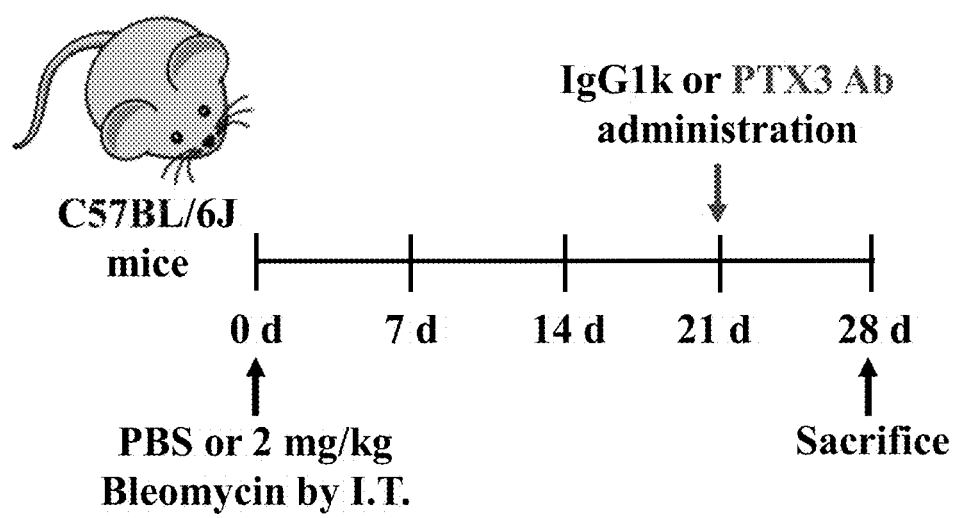
FIGS. 27A to 27D illustrate respectively an experimental scheme (FIG. 27A), a curve diagram of changes in body weight (FIG. 27B), gross examination of lung and histological staining images (FIGS. 27C and 27D) of BLM-induced pulmonary fibrosis of mice treated with PTX3 monoclonal antibody of EXAMPLE 1 according to an embodiment of the present invention.

In this EXAMPLE, the experimental schemes of FIG. 27A was used in the evaluation. Firstly, C57BL/6J male mice (six to eight weeks old, purchased from BioLASCO Taiwan Co., Ltd., Taiwan) were provided. Next, mice were intratracheally instilled (I.T.) with PBS or 2 mg/kg of bleomycin (BLM, Product Number: ap302, Enzo) to induce fibrosis. The $21^{st}$ day after fibrosis induction, the mice were i.p. injected with the control antibody (IgG1K, 10 mg/kg body weight, Product No. 10101, Leadgene Biomedical, Inc., Taiwan) or PTX3 antibody (10 mg/kg body weight, JustWin Biotech Co., Ltd.). All mice were euthanized at the $28^{th}$ day after fibrosis induction.

The body weights of C57BL/6J mice were individually measured on the seventh, $14^{th}$, $21^{st}$ or $28^{th}$ days after intratracheal instillation with BLM, and then these mice were i.p. injected with 10 mg/kg body weight of the control antibody IgG1K (the control group) or PTX3 antibody on the $21^{st}$ day. All results were shown in FIG. 27B.

After euthanization, the lung tissue of mice were grossly examined on the seventh, $14^{th}$, $21^{st}$ or $28^{th}$ days after intratracheal instillation with PBS (i.e. the healthy control group) or 2 mg/kg of BLM. The left lung lobes were intratracheally instilled, fixed in paraformaldehyde, and embedded in paraffin. The histological sections were stained by H&E, covered with cover slips and sealed. The histological sections were observed with 20× magnification, and all images were shown in FIG. 27C with a scale bar in 100 µm.

After euthanization, the BLM-induced pulmonary fibrosis tissues of mice were grossly examined on the $28^{th}$ day treated with 10 mg/mL of the control antibody (IgG1k) or PTX3 mAb. The left lung lobes were intratracheally instilled, fixed in paraformaldehyde, and embedded in paraffin. The histological sections were stained by H&E, covered with cover slips and sealed. The histological sections were observed with 20× magnification, and all images were shown in FIG. 27D with a scale bar in 100 µm.

Figure 27B:
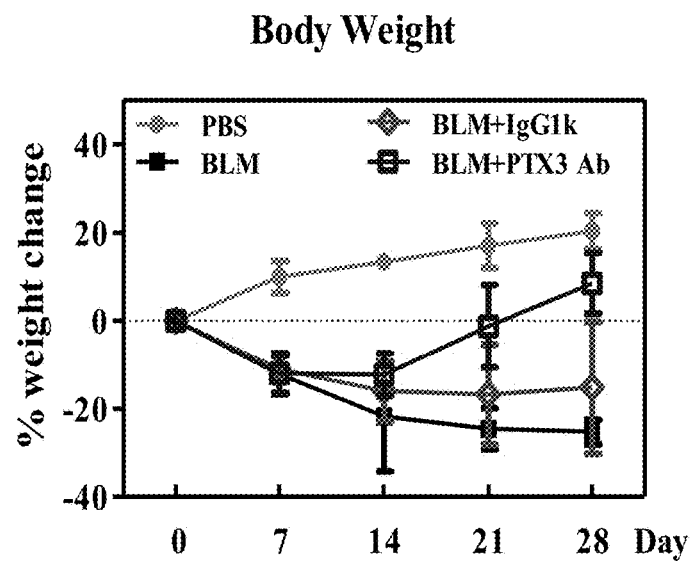
Figure 27C:
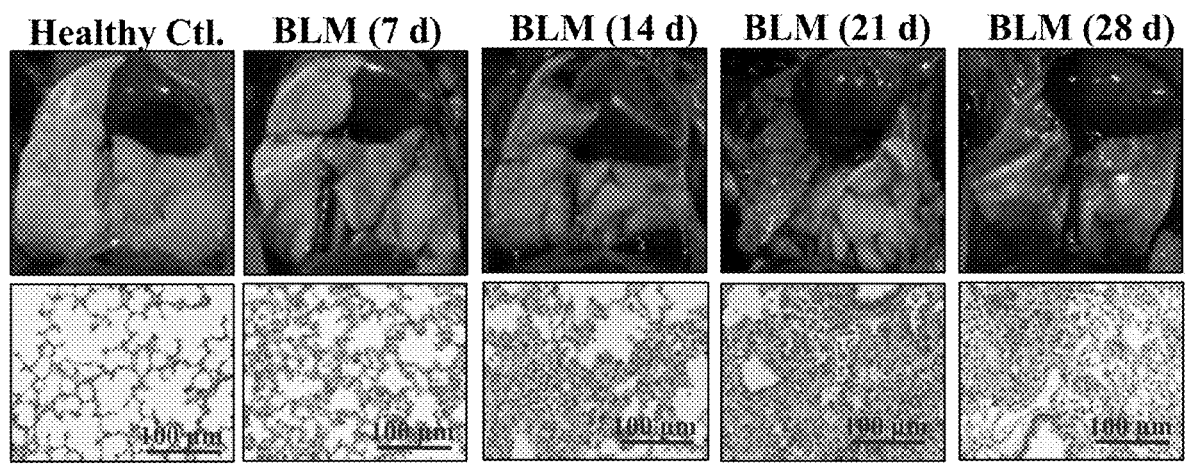
Figure 27D:
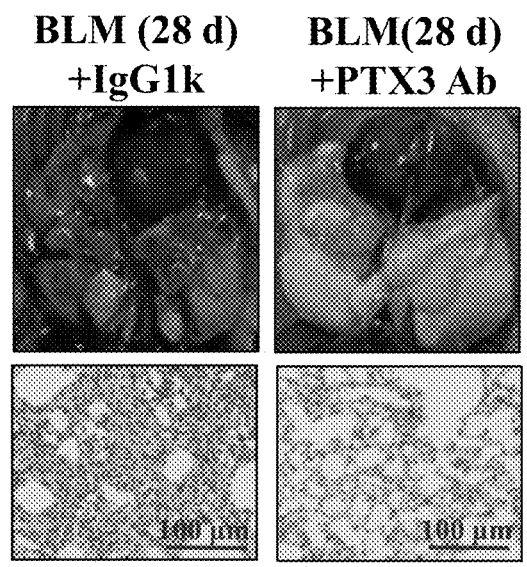

Reference was made to FIGS. 27B to 27D, which illustrated respectively a curve diagram of changes in body weight (FIG. 27B), gross examination of lung and histological staining images (FIGS. 27C and 27D) of BLM-induced pulmonary fibrosis of mice treated with PTX3 mAb of EXAMPLE 1 according to an embodiment of the present invention.

The results of FIGS. 27B to 27D were shown that, compared to the data of the control antibody (IgG1k), the PTX3 mAb of Example 1 could reverse the levels in pulmonary fibrosis and body weight loss caused by pulmonary fibrosis.

9. Evaluation of PTX3 Monoclonal Antibody of Example 1 Affecting Fibrosis-Related Protein Expression of Embryonic Fibroblasts NIH-3T3

In this EXAMPLE, mouse embryonic fibroblast cell line NIH-3T3 (Deposit Accession Number: BCRC 60008 or ATCC® CRL-1653™) was used in following experiments for evaluation of PTX3 monoclonal antibody of EXAMPLE 1 affecting fibrosis.

Firstly, NIH-3T3 cells were cultured in DMEM (12800-082, Gibco) (supplemented with 10% FBS, 100 µg/mL of streptomycin and 100 U/mL of penicillin).

NIH-3T3 cells were treated with 0.4 µg/mL of PTX3 mAb (JustWin Biotech Co., Ltd.), followed by treatment of 200 ng/mL of PTX3 recombinant protein for 6 hours. And then, NIH-3T3 cells were lysed in modified RIPA buffer. Next, Western blotting was used for detecting the expressions of α-tubulin (Product Number: T6199, Sigma), fibronectin (Product Number: 15613-1-AP, ProteinTech), Collagen type I (Product Number: 14695-1-AP, ProteinTech) and α-SMA (Product Number: GTX 100904, GeneTex) with specific antibodies, the expression of the α-tubulin served as a loading control group, and the result was shown in FIG. 28A.

In addition, NIH-3T3 cells were seeded into 24-well cell culture plate, and the medium in each lower well was added without or with 0.4 µg/mL of the control antibody IgG1k (Product No. 10101, Leadgene Biomedical, Inc., Taiwan), 0.4 µg/mL of PTX3 mAb (JustWin Biotech Co., Ltd.) or 200 ng/mL of PTX3 recombinant protein for 24 hours of treatment. Afterward, the NIH-3T3 cells were fixed in methanol at −20° C. overnight. On the next day, NIH-3T3 cells were stained by Picro-Sirius Red Solution (Product Number: ab246832, Abcam) under room temperature for 20 minutes, and rinsed twice by acetic acid. Nodule numbers of cells were counted according to images under optical microscope with 200× magnification. Later, the cells were lysed in 0.1N NaOH, and the absorbance of each well at 490 nm was detected by commercially available ELISA reader, and the results were shown in FIGS. 28B and 28C.

Figure 28A:
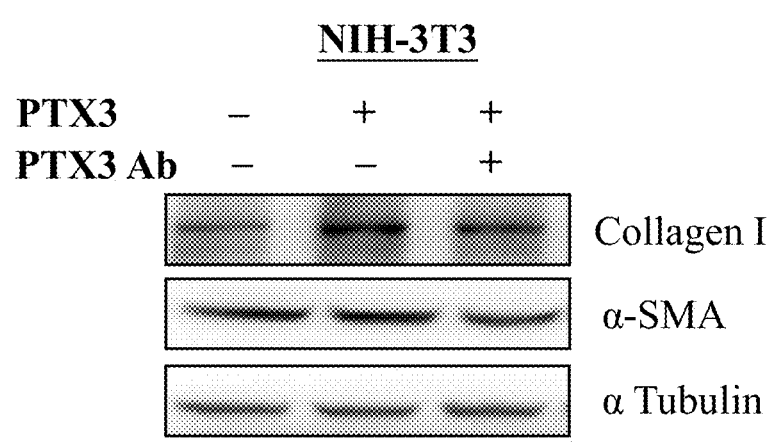
FIGS. 28A to 28C illustrate respectively western blotting images (FIG. 28A), images (FIG. 28B) and a bar diagram (FIG. 28C) of stained cells in nodules of embryonic fibroblasts treated with PTX3 monoclonal antibody according to an embodiment of the present invention.
Figure 28B:
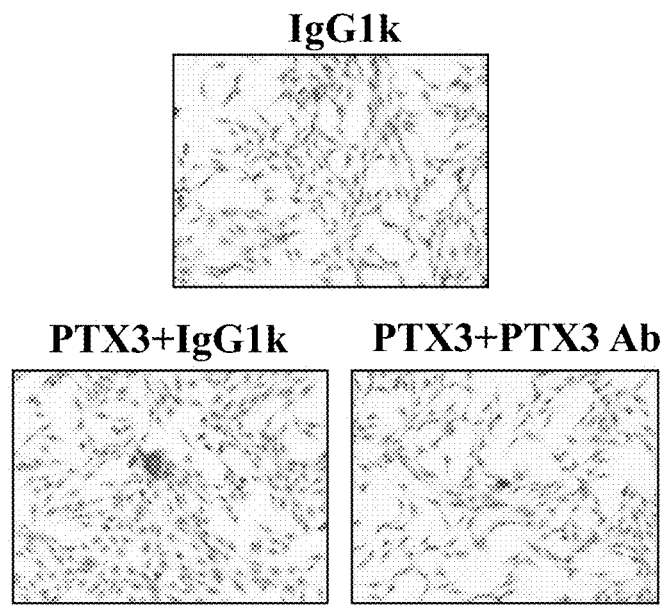
Figure 28C:
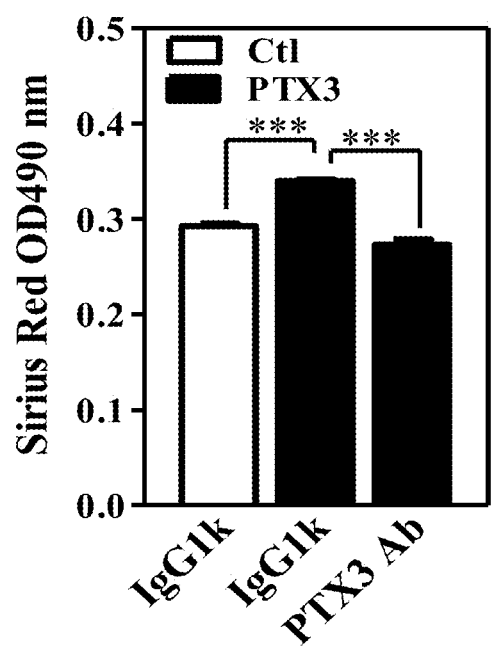

Reference was made to FIGS. 28A to 28C, which illustrated respectively western blotting images (FIG. 28A), images (FIG. 28B) and a bar diagram (FIG. 28C) of stained cells in nodules of embryonic fibroblasts treated with PTX3 mAb according to an embodiment of the present invention. Three asterisks (***) indicated the data having a statistically significant difference (p<0.001) compared to the control antibody (IgG1k).

The results of FIGS. 28A to 28C were shown that, compared to the data of the control antibody (IgG1k), the PTX3 mAb of Example 1 could reduce the expressions of fibrosis-related proteins and the nodule numbers of cells of NIH-3T3 cells.

10. Evaluation of PTX3 Monoclonal Antibody of Example 1 Affecting Fibrosis-Related Protein Expression of F28 Hepatic Fibroblasts In this EXAMPLE, human cancer associated fibroblast/F28 (CAF/F28 cells, or called as F28 hepatic fibroblast) was cultured in DMEM (12800-082, Gibco) (supplemented with 10% FBS, 100 μg/mL of streptomycin and 100 U/mL of penicillin).

CAF/F28 cells were exposed under 8 Gray (Gy) of radiation, followed by treatment of 0.4 μg/mL of PTX3 mAb (JustWin Biotech Co., Ltd.) for 6 hours. And then, CAF/F28 cells were lysed in modified RIPA buffer, which included 50 mM Tris-HCl (pH 7.4), 150 mM NaCl, 1 mM EDTA, 1% NP-40, 0.25% of sodium deoxycholate, 1 mM of dithiothreitol (DTT), 1 mM of phenylmethylsulfonyl fluoride (PMSF), aprotinin (1 mg/ml) and leupeptin (1 mg/ml). Next, Western blotting was used for detecting the expressions of α-tubulin (Product Number: T6199, Sigma), fibronectin (Product Number: 15613-1-AP, ProteinTech), Collagen type I (Product Number: 14695-1-AP, ProteinTech) and α-SMA (Product Number: GTX 100904, GeneTex) with specific antibodies, the expression of the α-tubulin served as a loading control group, and the result was shown in FIG. 29A.

In addition, CAF/F28 cells were treated with 0.4 μg/mL of PTX3 mAb (JustWin Biotech Co., Ltd.), followed by treatment with 200 ng/mL of PTX3 recombinant protein for 6 hours. And then, CAF/F28 cells were lysed in modified RIPA buffer. Next, Western blotting was used for detecting the expressions of α-tubulin (Product Number: T6199, Sigma), fibronectin (Product Number: 15613-1-AP, ProteinTech), Collagen type I (Product Number: 14695-1-AP, ProteinTech) and α-SMA (Product Number: GTX 100904, GeneTex) with specific antibodies, the expression of the α-tubulin served as a loading control group, and the result was shown in FIG. 29B.

Figure 29A:
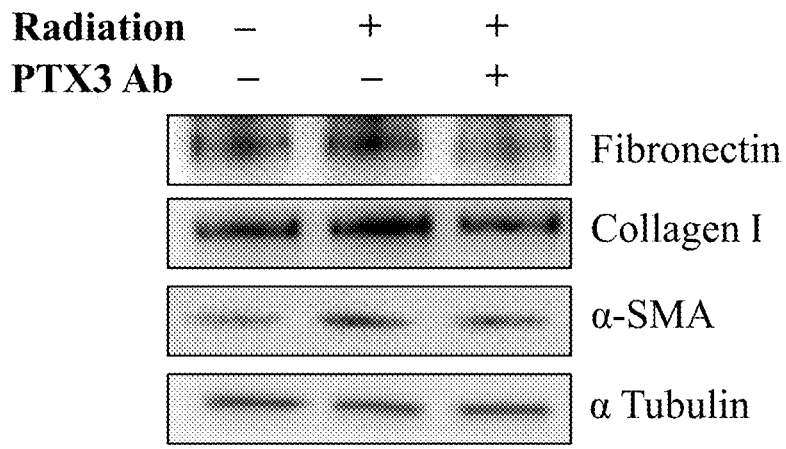
FIGS. 29A to 29B illustrate respectively western blotting images using PTX3 monoclonal antibody against fibrosis-related protein expression of hepatic fibroblasts in various treatments according to an embodiment of the present invention.
Figure 29B:
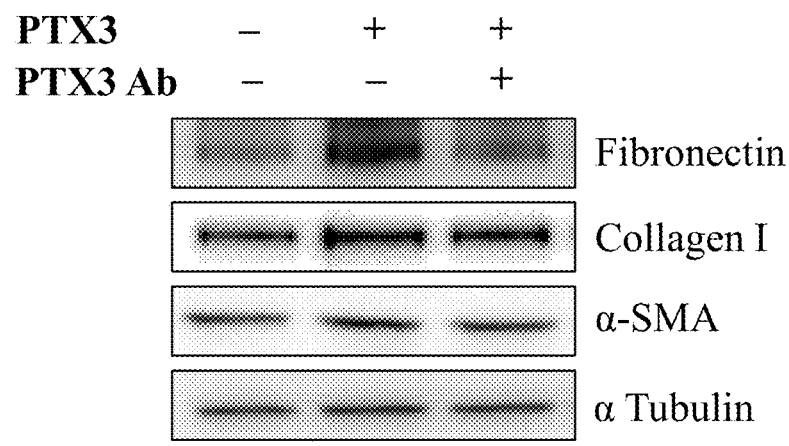

Reference was made to FIGS. 29A to 29B, which illustrated respectively western blotting images using PTX3 mAb against fibrosis-related protein expression of hepatic fibroblasts in various treatments according to an embodiment of the present invention.

The results of FIGS. 29A to 29B were shown that, compared to the data of the control antibody (IgG1k), the PTX3 mAb of Example 1 could alleviate expressions of fibrosis-related proteins of hepatic fibroblasts caused by radiation exposure or PTX3.

AH experiments on mice were performed according to the Guide for Care and Use of Laboratory Animals, National Cheng Kung University, Taiwan. The animal use protocol listed as above had been reviewed and approved by the Institutional Animal Care and Use Committee (IACUC).

It should be supplemented that, the PTX3 mAb of EXAMPLE 1 has excellent affinity and sensitivity to PTX3 recombinant protein, it can be applied in a set and a method for detecting PTX3, for in vitro detection of PTX3 amount in a biological specimen. The suitable biological specimens, methods, sets, devices/equipments have been recited as aforementioned and unnecessary to recite in detail. Moreover, the medicinal compositions and uses comprising the PTX3 monoclonal antibody or the antigen-binding fragment thereof, in which the PTX3 monoclonal antibody or the antigen-binding fragment thereof with higher affinity and sensitivity serves as an effective ingredient, can specifically inhibit or alleviate PTX3 receptor recognizing to PTX3, for specifically inhibiting or alleviating the disease or the symptom related to PTX3 receptor recognizing PTX3 protein, so that it can act as broad-spectrum drugs to treat various diseases.

In summary, the PTX3 monoclonal antibody having specific sequences, specific SNP sites, specific analysis models or specific evaluating methods are exemplified for clarifying the medicinal composition including monoclonal antibody or antigen-binding fragment and use of the same of the present invention. However, as is understood by a person skilled in the art, other analysis models or other evaluating methods can be also adopted in the medicinal composition including monoclonal antibody or antigen-binding fragment and use of the same of the present invention.

According to the embodiments of the present invention, the medicinal composition including the monoclonal antibody or antigen-binding fragment thereof advantageously includes the specific PTX3 monoclonal antibody or antigen-binding fragment thereof as the active ingredient, which can specifically inhibit or alleviate PTX3 receptor recognizing to PTX3, for applications on the set for in vitro detecting PTX3 and the method for in vitro diagnosing PTX3, as well as the medicinal compositions and uses as a medicament in the treatment of the disease or the symptom related to PTX3 receptor recognizing PTX3 protein.

Although the present invention has been described in considerable detail with reference to certain embodiments thereof, other embodiments are possible. Therefore, the spirit and scope of the appended claims should not be limited to the description of the embodiments contained herein.

What is claimed is:

1. An anti-PTX3 monoclonal antibody or antigen-binding fragment thereof comprising
a heavy chain variable (VH) domain comprising a CDR1 having an amino acid sequence listed as SEQ ID NO: 18, a CDR2 having an amino acid sequence listed as SEQ ID NO: 19 and a CDR3 having an amino acid sequence listed as SEQ ID NO: 21, and a light chain variable (VL) domain comprising a CDR1 having an amino acid sequences listed as SEQ ID NO: 22, a CDR2 having an amino acid sequence listed as SEQ ID NO: 23 and a CDR3 having an amino acid sequence listed as SEQ ID NO: 25; or
a heavy chain variable (VH) domain comprising a CDR1 having an amino acid sequence listed as SEQ ID NO: 18, a CDR2 having an amino acid sequence listed as SEQ ID NO: 20 and a CDR3 having an amino acid sequence listed as SEQ ID NO: 21, and a light chain variable (VL) domain comprising a CDR1 having an amino acid sequence listed as SEQ ID NO: 22, a CDR2 having an amino acid sequence listed as SEQ ID NO: 23 and a CDR3 having an amino acid sequence listed as SEQ ID NO: 24; or
a VH domain comprising a CDR1 having an amino acid sequence encoded by a nucleic acid sequence listed as SEQ ID NO: 26, a CDR2 having an amino acid sequence encoded by a nucleic acid sequence listed as SEQ ID NO:27 and a CDR3 having an amino acid sequence encoded by a nucleic acid sequence listed as SEQ ID NO:29, and a VL domain comprising a CDR1 having an amino acid sequence encoded by a nucleic acid sequence listed as SEQ ID NO: 30, a CDR2 having an amino acid sequence encoded by a nucleic acid sequence listed as SEQ ID NO: 31 and a CDR3 having an amino acid sequence encoded by a nucleic acid sequence listed as SEQ ID NO:32; or
a VH domain comprising a CDR1 having an amino acid sequence encoded by a nucleic acid sequence listed as SEQ ID NO: 26, a CDR2 having an amino acid sequence encoded by a nucleic acid sequence listed as SEQ ID NO:28 and a CDR3 having an amino acid sequence encoded by a nucleic acid sequence listed as SEQ ID NO:29, and a VL domain comprising a CDR1 having an amino acid sequence encoded by a nucleic acid sequence listed as SEQ ID NO: 30, a CDR2 having an amino acid sequence encoded by a nucleic acid sequence listed as SEQ ID NO:31 and a CDR3 having an amino acid sequence encoded by a nucleic acid sequence listed as SEQ ID NO:33; or
a VH domain comprising an amino acid sequence listed as SEQ ID NO: 34, and a VL domain comprising an amino acid sequence listed as SEQ ID NO: 36; or
a VH domain comprising an amino acid sequence listed as SEQ ID NO: 35, and a VL domain comprising an amino acid sequence listed as SEQ ID NO: 37; or
a VH domain comprising an amino acid sequence encoded by a nucleic acid sequence listed as SEQ ID NO: 38, and a VL domain comprising an amino acid sequence encoded by a nucleic acid sequence listed as SEQ ID NO: 41; or
a VH domain comprising an amino acid sequence encoded by a nucleic acid sequence listed as SEQ ID NO: 39, and a VL domain comprising an amino acid sequence encoded by a nucleic acid sequence listed as SEQ ID NO: 40.

2. The monoclonal antibody or antigen-binding fragment thereof of claim 1, wherein the monoclonal antibody or antigen-binding fragment thereof is a chimeric antibody, a murine antibody, a humanized antibody, a human-murine chimeric antibody, an antibody-drug conjugate (ADC) or antigen-binding fragment thereof.

3. The monoclonal antibody or antigen-binding fragment thereof of claim 1, wherein the antigen-binding fragment of the monoclonal antibody is a single-chain variable fragment (scFv), a scFv dimer [(scFv)$_2$], a scFv trimer [(scFv)$_3$], a variable fragment (Fv), a Fab fragment, a Fab' fragment, a dimeric Fab' fragment [F(ab')$_2$], or any combination thereof.

4. The monoclonal antibody or antigen-binding fragment thereof of claim 1, wherein the antigen-binding fragment of the monoclonal antibody is modified by conjugation, coupling, glycosylation, tag attachment or any combination thereof.

5. The monoclonal antibody or antigen-binding fragment thereof of claim 1, wherein the monoclonal antibody or antigen-binding fragment thereof is a bifunctional monoclonal antibody (BsAb) or a trifunctional monoclonal antibody or antigen-binding fragment thereof.

6. The monoclonal antibody or antigen-binding fragment thereof of claim 1, wherein the monoclonal antibody or antigen-binding fragment thereof belongs to IgG class IgM class, IgA class, IgD class or IgE class.

7. The monoclonal antibody or antigen-binding fragment thereof of claim 1, wherein the monoclonal antibody or antigen-binding fragment thereof belongs to an inert antibody or an antagonist antibody.

8. The monoclonal antibody or antigen-binding fragment thereof of claim 1, wherein the monoclonal antibody or fragment thereof specifically inhibits or alleviates activities of one or more PTX3 proteins.

9. A kit for detecting PTX3, comprising a monoclonal antibody or antigen-binding fragment thereof of claim 1, wherein the monoclonal antibody or the antigen-binding fragment thereof specifically binds to a non-denatured amino acid sequence, and the non-denatured amino acid sequence is selected from the group consisting of amino acid sequences listed as SEQ ID NOs: 1 to 11.

10. A medicinal composition, comprising an effective dose of a monoclonal antibody or an antigen-binding fragment thereof of claim 1 as an active ingredient and a pharmaceutically acceptable carrier.

11. The medicinal composition of claim 10, further comprising an active pharmaceutical ingredient.

12. The medicinal composition of claim 10, wherein the effective dose is 2 mg/kg body weight (mg/kg BW) to 10 mg/kg BW.

13. A method for specifically inhibiting or alleviating a disease or a symptom related to PTX3 binding to PTX3 receptor, comprising:
  administering a medicinal composition of claim 10 in which and the monoclonal antibody or antigen-binding fragment thereof is present in an effective dose, thereby inhibiting or alleviating binding of PTX3 to PTX3 receptor.

14. The method of claim 13, wherein the disease or the symptom comprises carcinoma, adenocarcinoma, glioblastoma multiforme (GBM) and fibrosis.

15. The method of claim 14, wherein the carcinoma comprises lung cancer, breast cancer and nasopharyngeal cancer, the adenocarcinoma comprises colorectal cancer, and an organ influenced by the disease or the symptom of the fibrosis is selected from the group consisting of lung, liver, kidney and skin.

16. The method of claim 13, wherein the medicament is administered via subcutaneous injection, intramuscular injection, intravenous injection, intraperitoneal injection, orthotopic injection, oral administration or nasal inhalation.

17. A method of inhibiting or alleviating an activity of a tumor cell or a disease or a symptom related to fibrosis in vitro, comprising administering an effective dose of the medicinal composition of claim 10 to the tumor cell or an organ affected by the disease or the symptom related to the fibrosis, thereby inhibiting or alleviating activities of the tumor cell or the disease or the symptom of the organ.

18. The method of claim 17, wherein a source of the tumor cell comprises a glioblastoma multiforme (GBM), carcinoma and adenocarcinoma, and the organ is selected from the group consisting of lung, liver, kidney and skin.

19. The method of claim 18, wherein the carcinoma comprises lung cancer, breast cancer and nasopharyngeal cancer, the adenocarcinoma comprises colorectal cancer.

20. The method of claim 17, wherein the activity comprises proliferation, cancer stemness, migration, invasiveness, metastasis, tumor volume or drug resistance.

21. The monoclonal antibody or antigen-binding fragment thereof of claim 1, wherein the monoclonal antibody or antigen-binding fragment thereof belongs to IgG1 isotype, IgG2 isotype, IgG3 isotype or IgG4 isotype.

* * * * *

SEQUENCE LISTING

```
<160> NUMBER OF SEQ ID NOS: 41

<210> SEQ ID NO 1
<211> LENGTH: 9
<212> TYPE: PRT
<213> ORGANISM: Artificial
<220> FEATURE:
```

<223> OTHER INFORMATION: Synthetic

<400> SEQUENCE: 1

Arg Pro Met Arg Leu Glu Ser Phe Ser
1               5

<210> SEQ ID NO 2
<211> LENGTH: 9
<212> TYPE: PRT
<213> ORGANISM: Artificial
<220> FEATURE:
<223> OTHER INFORMATION: Synthetic

<400> SEQUENCE: 2

Arg Leu Glu Ser Phe Ser Ala Cys Ile
1               5

<210> SEQ ID NO 3
<211> LENGTH: 9
<212> TYPE: PRT
<213> ORGANISM: Artificial
<220> FEATURE:
<223> OTHER INFORMATION: Synthetic

<400> SEQUENCE: 3

Ser Phe Ser Ala Cys Ile Trp Val Lys
1               5

<210> SEQ ID NO 4
<211> LENGTH: 9
<212> TYPE: PRT
<213> ORGANISM: Artificial
<220> FEATURE:
<223> OTHER INFORMATION: Synthetic

<400> SEQUENCE: 4

Ala Cys Ile Trp Val Lys Ala Thr Asp
1               5

<210> SEQ ID NO 5
<211> LENGTH: 9
<212> TYPE: PRT
<213> ORGANISM: Artificial
<220> FEATURE:
<223> OTHER INFORMATION: Synthetic

<400> SEQUENCE: 5

Trp Val Lys Ala Thr Asp Val Leu Asn
1               5

<210> SEQ ID NO 6
<211> LENGTH: 9
<212> TYPE: PRT
<213> ORGANISM: Artificial
<220> FEATURE:
<223> OTHER INFORMATION: Synthetic

<400> SEQUENCE: 6

Ala Thr Asp Val Leu Asn Lys Thr Ile
1               5

<210> SEQ ID NO 7
<211> LENGTH: 9
<212> TYPE: PRT
<213> ORGANISM: Artificial
<220> FEATURE:
<223> OTHER INFORMATION: Synthetic

```
<400> SEQUENCE: 7

Val Leu Asn Lys Thr Ile Leu Phe Ser
1               5

<210> SEQ ID NO 8
<211> LENGTH: 9
<212> TYPE: PRT
<213> ORGANISM: Artificial
<220> FEATURE:
<223> OTHER INFORMATION: Synthetic

<400> SEQUENCE: 8

Lys Thr Ile Leu Phe Ser Tyr Gly Thr
1               5

<210> SEQ ID NO 9
<211> LENGTH: 9
<212> TYPE: PRT
<213> ORGANISM: Artificial
<220> FEATURE:
<223> OTHER INFORMATION: Synthetic

<400> SEQUENCE: 9

Leu Phe Ser Tyr Gly Thr Lys Arg Asn
1               5

<210> SEQ ID NO 10
<211> LENGTH: 10
<212> TYPE: PRT
<213> ORGANISM: Artificial
<220> FEATURE:
<223> OTHER INFORMATION: Synthetic

<400> SEQUENCE: 10

Tyr Gly Thr Lys Arg Asn Pro Tyr Glu Ile
1               5                   10

<210> SEQ ID NO 11
<211> LENGTH: 15
<212> TYPE: PRT
<213> ORGANISM: Artificial
<220> FEATURE:
<223> OTHER INFORMATION: Synthetic

<400> SEQUENCE: 11

Arg Leu Glu Ser Phe Ser Ala Cys Ile Trp Val Lys Ala Thr Asp
1               5                   10                  15

<210> SEQ ID NO 12
<211> LENGTH: 37
<212> TYPE: PRT
<213> ORGANISM: Artificial
<220> FEATURE:
<223> OTHER INFORMATION: Synthetic

<400> SEQUENCE: 12

Arg Pro Met Arg Leu Glu Ser Phe Ser Ala Cys Ile Trp Val Lys Ala
1               5                   10                  15

Thr Asp Val Leu Asn Lys Thr Ile Leu Phe Ser Tyr Gly Thr Lys Arg
            20                  25                  30

Asn Pro Tyr Glu Ile
        35

<210> SEQ ID NO 13
```

<211> LENGTH: 160
<212> TYPE: PRT
<213> ORGANISM: Artificial
<220> FEATURE:
<223> OTHER INFORMATION: Synthetic

<400> SEQUENCE: 13

Arg Pro Met Arg Leu Glu Ser Phe Ser Ala Cys Ile Trp Val Lys Ala
1               5                   10                  15

Thr Asp Val Leu Asn Lys Thr Ile Leu Phe Ser Tyr Gly Thr Lys Arg
            20                  25                  30

Asn Pro Tyr Glu Ile Gln Leu Tyr Leu Ser Tyr Gln Ser Ile Val Phe
        35                  40                  45

Val Val Gly Gly Glu Glu Asn Lys Leu Val Ala Glu Ala Met Val Ser
    50                  55                  60

Leu Gly Arg Trp Thr His Leu Cys Gly Thr Trp Asn Ser Glu Glu Gly
65                  70                  75                  80

Leu Thr Ser Leu Trp Val Asn Gly Glu Leu Ala Ala Thr Thr Val Glu
                85                  90                  95

Met Ala Thr Gly His Ile Val Pro Glu Gly Gly Ile Leu Gln Ile Gly
            100                 105                 110

Gln Glu Lys Asn Gly Cys Cys Val Gly Gly Phe Asp Glu Thr Leu
        115                 120                 125

Ala Phe Ser Gly Arg Leu Thr Gly Phe Asn Ile Trp Asp Ser Val Leu
    130                 135                 140

Ser Asn Glu Glu Ile Arg Glu Thr Gly Gly Ala Glu Ser Cys His Ile
145                 150                 155                 160

<210> SEQ ID NO 14
<211> LENGTH: 363
<212> TYPE: PRT
<213> ORGANISM: Artificial
<220> FEATURE:
<223> OTHER INFORMATION: Synthetic

<400> SEQUENCE: 14

Asn Ser Asp Asp Tyr Asp Leu Met Tyr Val Asn Leu Asp Asn Glu Ile
1               5                   10                  15

Asp Asn Gly Leu His Pro Thr Glu Asp Pro Thr Pro Cys Ala Cys Gly
            20                  25                  30

Gln Glu His Ser Glu Trp Asp Lys Leu Phe Ile Met Leu Glu Asn Ser
        35                  40                  45

Gln Met Arg Glu Arg Met Leu Leu Gln Ala Thr Asp Asp Val Leu Arg
    50                  55                  60

Gly Glu Leu Gln Arg Leu Arg Glu Leu Gly Arg Leu Ala Glu Ser
65                  70                  75                  80

Leu Ala Arg Pro Cys Ala Pro Gly Ala Pro Ala Glu Ala Arg Leu Thr
                85                  90                  95

Ser Ala Leu Asp Glu Leu Leu Gln Ala Thr Arg Asp Ala Gly Arg Arg
            100                 105                 110

Leu Ala Arg Met Glu Gly Ala Glu Ala Gln Arg Pro Glu Glu Ala Gly
        115                 120                 125

Arg Ala Leu Ala Ala Val Leu Glu Glu Leu Arg Gln Thr Arg Ala Asp
    130                 135                 140

Leu His Ala Val Gln Gly Trp Ala Ala Arg Ser Trp Leu Pro Ala Gly
145                 150                 155                 160

```
Cys Glu Thr Ala Ile Leu Phe Pro Met Arg Ser Lys Lys Ile Phe Gly
                165                 170                 175

Ser Val His Pro Val Arg Pro Met Arg Leu Glu Ser Phe Ser Ala Cys
            180                 185                 190

Ile Trp Val Lys Ala Thr Asp Val Leu Asn Lys Thr Ile Leu Phe Ser
        195                 200                 205

Tyr Gly Thr Lys Arg Asn Pro Tyr Glu Ile Gln Leu Tyr Leu Ser Tyr
    210                 215                 220

Gln Ser Ile Val Phe Val Gly Glu Glu Asn Lys Leu Val Ala
225                 230                 235                 240

Glu Ala Met Val Ser Leu Gly Arg Trp Thr His Leu Cys Gly Thr Trp
                245                 250                 255

Asn Ser Glu Glu Gly Leu Thr Ser Leu Trp Val Asn Gly Glu Leu Ala
            260                 265                 270

Ala Thr Thr Val Glu Met Ala Thr Gly His Ile Val Pro Glu Gly Gly
        275                 280                 285

Ile Leu Gln Ile Gly Gln Glu Lys Asn Gly Cys Cys Val Gly Gly Gly
    290                 295                 300

Phe Asp Glu Thr Leu Ala Phe Ser Gly Arg Leu Thr Gly Phe Asn Ile
305                 310                 315                 320

Trp Asp Ser Val Leu Ser Asn Glu Glu Ile Arg Glu Thr Gly Gly Ala
                325                 330                 335

Glu Ser Cys His Ile Arg Gly Asn Ile Val Gly Trp Gly Val Thr Glu
            340                 345                 350

Ile Gln Pro His Gly Gly Ala Gln Tyr Val Ser
        355                 360
```

<210> SEQ ID NO 15
<211> LENGTH: 381
<212> TYPE: PRT
<213> ORGANISM: Artificial
<220> FEATURE:
<223> OTHER INFORMATION: Synthetic

<400> SEQUENCE: 15

```
Met His Leu Leu Ala Ile Leu Phe Cys Ala Leu Trp Ser Ala Val Leu
1               5                   10                  15

Ala Glu Asn Ser Asp Asp Tyr Asp Leu Met Tyr Val Asn Leu Asp Asn
                20                  25                  30

Glu Ile Asp Asn Gly Leu His Pro Thr Glu Asp Pro Thr Pro Cys Ala
            35                  40                  45

Cys Gly Gln Glu His Ser Glu Trp Asp Lys Leu Phe Ile Met Leu Glu
    50                  55                  60

Asn Ser Gln Met Arg Glu Arg Met Leu Leu Gln Ala Thr Asp Asp Val
65                  70                  75                  80

Leu Arg Gly Glu Leu Gln Arg Leu Arg Glu Glu Leu Gly Arg Leu Ala
                85                  90                  95

Glu Ser Leu Ala Arg Pro Cys Ala Pro Gly Ala Pro Ala Glu Ala Arg
            100                 105                 110

Leu Thr Ser Ala Leu Asp Glu Leu Leu Gln Ala Thr Arg Asp Ala Gly
    115                 120                 125

Arg Arg Leu Ala Arg Met Glu Gly Ala Glu Ala Gln Arg Pro Glu Glu
130                 135                 140

Ala Gly Arg Ala Leu Ala Ala Val Leu Glu Glu Leu Arg Gln Thr Arg
                145                 150                 155                 160
```

```
Ala Asp Leu His Ala Val Gln Gly Trp Ala Arg Ser Trp Leu Pro
            165                 170                 175

Ala Gly Cys Glu Thr Ala Ile Leu Phe Pro Met Arg Ser Lys Lys Ile
        180                 185                 190

Phe Gly Ser Val His Pro Val Arg Pro Met Arg Leu Glu Ser Phe Ser
        195                 200                 205

Ala Cys Ile Trp Val Lys Ala Thr Asp Val Leu Asn Lys Thr Ile Leu
        210                 215                 220

Phe Ser Tyr Gly Thr Lys Arg Asn Pro Tyr Glu Ile Gln Leu Tyr Leu
225                 230                 235                 240

Ser Tyr Gln Ser Ile Val Phe Val Val Gly Glu Glu Asn Lys Leu
            245                 250                 255

Val Ala Glu Ala Met Val Ser Leu Gly Arg Trp Thr His Leu Cys Gly
        260                 265                 270

Thr Trp Asn Ser Glu Glu Gly Leu Thr Ser Leu Trp Val Asn Gly Glu
        275                 280                 285

Leu Ala Ala Thr Thr Val Glu Met Ala Thr Gly His Ile Val Pro Glu
        290                 295                 300

Gly Gly Ile Leu Gln Ile Gly Gln Glu Lys Asn Gly Cys Cys Val Gly
305                 310                 315                 320

Gly Gly Phe Asp Glu Thr Leu Ala Phe Ser Gly Arg Leu Thr Gly Phe
                325                 330                 335

Asn Ile Trp Asp Ser Val Leu Ser Asn Glu Glu Ile Arg Glu Thr Gly
            340                 345                 350

Gly Ala Glu Ser Cys His Ile Arg Gly Asn Ile Val Gly Trp Gly Val
        355                 360                 365

Thr Glu Ile Gln Pro His Gly Gly Ala Gln Tyr Val Ser
        370                 375                 380

<210> SEQ ID NO 16
<211> LENGTH: 44
<212> TYPE: PRT
<213> ORGANISM: Artificial
<220> FEATURE:
<223> OTHER INFORMATION: Synthetic

<400> SEQUENCE: 16

Lys Leu Val Ala Glu Ala Met Val Ser Leu Gly Arg Trp Thr His Leu
1               5                   10                  15

Cys Gly Thr Trp Asn Ser Glu Glu Gly Leu Thr Ser Leu Trp Val Asn
            20                  25                  30

Gly Glu Leu Ala Ala Thr Thr Val Glu Met Ala Thr
        35                  40

<210> SEQ ID NO 17
<211> LENGTH: 40
<212> TYPE: PRT
<213> ORGANISM: Artificial
<220> FEATURE:
<223> OTHER INFORMATION: Synthetic

<400> SEQUENCE: 17

Gly Gly Gly Phe Asp Glu Thr Leu Ala Phe Ser Gly Arg Leu Thr Gly
1               5                   10                  15

Phe Asn Ile Trp Asp Ser Val Leu Ser Asn Glu Glu Ile Arg Glu Thr
            20                  25                  30
```

Gly Gly Ala Glu Ser Cys His Ile
        35                  40

<210> SEQ ID NO 18
<211> LENGTH: 10
<212> TYPE: PRT
<213> ORGANISM: Artificial
<220> FEATURE:
<223> OTHER INFORMATION: Synthetic

<400> SEQUENCE: 18

Asp Phe Asn Ile Lys His Thr Tyr Leu His
1               5                   10

<210> SEQ ID NO 19
<211> LENGTH: 17
<212> TYPE: PRT
<213> ORGANISM: Artificial
<220> FEATURE:
<223> OTHER INFORMATION: Synthetic

<400> SEQUENCE: 19

Arg Ile Asp Pro Ala Asn Asp Asn Thr Lys Tyr Asp Pro Met Phe Gln
1               5                   10                  15

Gly

<210> SEQ ID NO 20
<211> LENGTH: 17
<212> TYPE: PRT
<213> ORGANISM: Artificial
<220> FEATURE:
<223> OTHER INFORMATION: Synthetic

<400> SEQUENCE: 20

Arg Ile Asp Pro Ala Asn Gly Asp Thr Lys Tyr Asp Pro Lys Phe Gln
1               5                   10                  15

Gly

<210> SEQ ID NO 21
<211> LENGTH: 11
<212> TYPE: PRT
<213> ORGANISM: Artificial
<220> FEATURE:
<223> OTHER INFORMATION: Synthetic

<400> SEQUENCE: 21

Ala Arg Val Thr Thr Val Val Gly Phe Asp Tyr
1               5                   10

<210> SEQ ID NO 22
<211> LENGTH: 12
<212> TYPE: PRT
<213> ORGANISM: Artificial
<220> FEATURE:
<223> OTHER INFORMATION: Synthetic

<400> SEQUENCE: 22

Thr Ala Ser Ser Ser Val Ile Ser Thr Tyr Leu Asn
1               5                   10

<210> SEQ ID NO 23
<211> LENGTH: 7
<212> TYPE: PRT
<213> ORGANISM: Artificial
<220> FEATURE:

```
<223> OTHER INFORMATION: Synthetic

<400> SEQUENCE: 23

Ser Thr Ser Asn Leu Ala Ser
1               5

<210> SEQ ID NO 24
<211> LENGTH: 9
<212> TYPE: PRT
<213> ORGANISM: Artificial
<220> FEATURE:
<223> OTHER INFORMATION: Synthetic

<400> SEQUENCE: 24

His Gln Phe Gln Arg Ser Pro Leu Thr
1               5

<210> SEQ ID NO 25
<211> LENGTH: 9
<212> TYPE: PRT
<213> ORGANISM: Artificial
<220> FEATURE:
<223> OTHER INFORMATION: Synthetic

<400> SEQUENCE: 25

His Gln Tyr Gln Arg Ser Pro Leu Thr
1               5

<210> SEQ ID NO 26
<211> LENGTH: 30
<212> TYPE: DNA
<213> ORGANISM: Artificial
<220> FEATURE:
<223> OTHER INFORMATION: Synthetic

<400> SEQUENCE: 26
gacttcaaca ttaaacatac ctatctgcac                                     30

<210> SEQ ID NO 27
<211> LENGTH: 51
<212> TYPE: DNA
<213> ORGANISM: Artificial
<220> FEATURE:
<223> OTHER INFORMATION: Synthetic

<400> SEQUENCE: 27
aggattgatc ctgcgaatgg tgatactaaa tatgacccga agttccaggg c              51

<210> SEQ ID NO 28
<211> LENGTH: 51
<212> TYPE: DNA
<213> ORGANISM: Artificial
<220> FEATURE:
<223> OTHER INFORMATION: Synthetic

<400> SEQUENCE: 28
aggattgatc ctgcgaatga taatactaaa tatgacccga tgttccaggg c              51

<210> SEQ ID NO 29
<211> LENGTH: 33
<212> TYPE: DNA
<213> ORGANISM: Artificial
<220> FEATURE:
<223> OTHER INFORMATION: Synthetic
```

<400> SEQUENCE: 29
gctagagtta ctacggttgt aggctttgac tac                      33

<210> SEQ ID NO 30
<211> LENGTH: 27
<212> TYPE: DNA
<213> ORGANISM: Artificial
<220> FEATURE:
<223> OTHER INFORMATION: Synthetic

<400> SEQUENCE: 30
actgccagct caagtgtaat ttccact                             27

<210> SEQ ID NO 31
<211> LENGTH: 21
<212> TYPE: DNA
<213> ORGANISM: Artificial
<220> FEATURE:
<223> OTHER INFORMATION: Synthetic

<400> SEQUENCE: 31
agcacatcca acctggcttc t                                   21

<210> SEQ ID NO 32
<211> LENGTH: 27
<212> TYPE: DNA
<213> ORGANISM: Artificial
<220> FEATURE:
<223> OTHER INFORMATION: Synthetic

<400> SEQUENCE: 32
caccagtttc agcgttcccc gctcacg                             27

<210> SEQ ID NO 33
<211> LENGTH: 27
<212> TYPE: DNA
<213> ORGANISM: Artificial
<220> FEATURE:
<223> OTHER INFORMATION: Synthetic

<400> SEQUENCE: 33
caccagtatc agcgttcccc gctcacg                             27

<210> SEQ ID NO 34
<211> LENGTH: 118
<212> TYPE: PRT
<213> ORGANISM: Artificial
<220> FEATURE:
<223> OTHER INFORMATION: Synthetic

<400> SEQUENCE: 34

Glu Val Gln Leu Gln Gln Ser Gly Ala Glu Leu Val Lys Pro Gly Ala
1               5                   10                  15

Ser Val Lys Leu Ser Cys Thr Ala Ser Asp Phe Asn Ile Lys His Thr
            20                  25                  30

Tyr Leu His Trp Val Leu Gln Arg Pro Glu Gln Gly Leu Glu Trp Ile
        35                  40                  45

Gly Arg Ile Asp Pro Ala Asn Gly Asp Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Arg Val Thr Thr Val Val Gly Phe Asp Tyr Trp Gly Gln Gly Thr
            100                 105                 110

Thr Leu Thr Val Ser Ser
        115

<210> SEQ ID NO 35
<211> LENGTH: 118
<212> TYPE: PRT
<213> ORGANISM: Artificial
<220> FEATURE:
<223> OTHER INFORMATION: Synthetic

<400> SEQUENCE: 35

Glu Val Gln Leu Gln Gln Ser Gly Ala Glu Leu Val Lys Pro Gly Ala
1               5                   10                  15

Ser Val Lys Leu Ser Cys Thr Ala Ser Asp Phe Asn Ile Lys His Thr
            20                  25                  30

Tyr Leu His Trp Val Leu Gln Arg Pro Glu Gln Gly Leu Glu Trp Ile
        35                  40                  45

Gly Arg Ile Asp Pro Ala Asn Asp Asn Thr Lys Tyr Asp Pro Met Phe
    50                  55                  60

Gln Gly Lys Ala Thr Ile Thr Ala Asp Thr Ser Ser Asn Thr Ala Tyr
65                  70                  75                  80

Leu His Leu Ser Ser Leu Thr Ser Glu Asp Thr Ala Val Tyr Tyr Cys
                85                  90                  95

Ala Arg Val Thr Thr Val Val Gly Phe Asp Tyr Trp Gly Gln Gly Thr
            100                 105                 110

Thr Leu Thr Val Ser Ser
        115

<210> SEQ ID NO 36
<211> LENGTH: 109
<212> TYPE: PRT
<213> ORGANISM: Artificial
<220> FEATURE:
<223> OTHER INFORMATION: Synthetic

<400> SEQUENCE: 36

Gln Ile Val Leu Thr Gln Ser Pro Ala Ile Met Ser Thr Ser Leu Gly
1               5                   10                  15

Glu Arg Val Thr Met Thr Cys Thr Ala Ser Ser Ser Val Ile Ser Thr
            20                  25                  30

Tyr Leu Asn Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Phe Cys His Gln Phe Gln Arg Ser Pro
                85                  90                  95

Leu Thr Phe Gly Ala Gly Thr Lys Leu Glu Leu Lys Arg
            100                 105

<210> SEQ ID NO 37
<211> LENGTH: 109
<212> TYPE: PRT

<213> ORGANISM: Artificial
<220> FEATURE:
<223> OTHER INFORMATION: Synthetic

<400> SEQUENCE: 37

```
Gln Ile Val Leu Thr Gln Ser Pro Ala Ile Met Ser Thr Ser Leu Gly
1               5                   10                  15

Glu Arg Val Thr Met Thr Cys Thr Ala Ser Ser Ser Val Ile Ser Thr
            20                  25                  30

Tyr Leu Asn Trp Tyr Gln Gln Lys Pro Gly Ser Ser Pro Lys Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Thr Tyr Phe Cys His Gln Tyr Gln Arg Ser Pro
                85                  90                  95

Leu Thr Phe Gly Ala Gly Thr Lys Leu Glu Leu Lys Arg
            100                 105
```

<210> SEQ ID NO 38
<211> LENGTH: 354
<212> TYPE: DNA
<213> ORGANISM: Artificial
<220> FEATURE:
<223> OTHER INFORMATION: Synthetic

<400> SEQUENCE: 38

```
gaggttcagc tgcagcagtc tggggcagag cttgtgaagc caggggcctc agtcaagttg     60
tcctgcacag cttctgactt caacattaaa catacctatc tgcactgggt gctccagagg    120
cctgaacagg gcctggagtg gattggaagg attgatcctg cgaatgataa tactaaatat    180
gacccgatgt tccagggcaa ggccactata acagcagaca catcctccaa cacagcctac    240
ctgcacctca gcagcctgac atctgaggac actgccgtct attactgtgc tagagttact    300
acggttgtag gctttgacta ctggggccaa ggcaccactc tcacagtctc ctca          354
```

<210> SEQ ID NO 39
<211> LENGTH: 354
<212> TYPE: DNA
<213> ORGANISM: Artificial
<220> FEATURE:
<223> OTHER INFORMATION: Synthetic

<400> SEQUENCE: 39

```
gaggttcagc tgcagcagtc tggggcagag cttgtgaagc caggggcctc agtcaagttg     60
tcctgcacag cttctgactt caacattaaa catacctatc tgcactgggt gctccagagg    120
cctgaacagg gcctggagtg gattggaagg attgatcctg cgaatggtga tactaaatat    180
gacccgaagt tccagggcaa ggccactata acagcagaca catcctccaa cacagcctac    240
ctgcacctca gcagcctgac atctgaggac actgccgtct attactgtgc tagagttact    300
acggttgtag gctttgacta ctggggccaa ggcaccactc tcacagtctc ctca          354
```

<210> SEQ ID NO 40
<211> LENGTH: 327
<212> TYPE: DNA
<213> ORGANISM: Artificial
<220> FEATURE:
<223> OTHER INFORMATION: Synthetic

```
<400> SEQUENCE: 40
caaattgttc tcacccagtc tccagcaatc atgtctacat ctctagggga acgggtcacc      60
atgacctgca ctgccagctc aagtgtaatt tccacttact tgaactggta ccagcagaag     120
ccaggatcct cccccaaact ctggatttat agcacatcca acctggcttc tggagtccca     180
gctcgcttca gtggcagtgg gtctgggacc tcttactctc tcacaatcag tagcatggag     240
gctgaagatg ctgccactta tttctgccac cagtttcagc gttccccgct cacgttcggt     300
gctgggacca agctggagct gaaacgg                                         327

<210> SEQ ID NO 41
<211> LENGTH: 327
<212> TYPE: DNA
<213> ORGANISM: Artificial
<220> FEATURE:
<223> OTHER INFORMATION: Synthetic

<400> SEQUENCE: 41
caaattgttc tcacccagtc tccagcaatc atgtctacat ctctagggga acgggtcacc      60
atgacctgca ctgccagctc aagtgtaatt tccacttact tgaactggta ccagcagaag     120
ccaggatcct cccccaaact ctggatttat agcacatcca acctggcttc tggagtccca     180
gctcgcttca gtggcagtgg gtctgggacc tcttactctc tcacaatcag tagcatggag     240
gctgaagatg ctgccactta tttctgccac cagtatcagc gttccccgct cacgttcggt     300
gctgggacca agctggagct gaaacgg                                         327
```